(12) United States Patent
Choi et al.

(10) Patent No.: US 9,395,473 B2
(45) Date of Patent: Jul. 19, 2016

(54) NANO-OPTIC FILTER ARRAY BASED SENSOR

(75) Inventors: Byung Il Choi, Pittsburgh, PA (US); Byounghee Lee, Pittsburgh, PA (US); Min Kyu Song, Pittsburgh, PA (US)

(73) Assignee: NANOLAMBDA, INC., Pittsburgh, PA (US)

( * ) Notice: Subject to any disclaimer, the term of this patent is extended or adjusted under 35 U.S.C. 154(b) by 438 days.

(21) Appl. No.: 13/257,561

(22) PCT Filed: Mar. 19, 2010

(86) PCT No.: PCT/US2010/027957
§ 371 (c)(1),
(2), (4) Date: Feb. 3, 2012

(87) PCT Pub. No.: WO2010/108086
PCT Pub. Date: Sep. 23, 2010

(65) Prior Publication Data
US 2012/0129269 A1    May 24, 2012

Related U.S. Application Data

(60) Provisional application No. 61/161,892, filed on Mar. 20, 2009.

(51) Int. Cl.
*G01N 21/00* (2006.01)
*G02B 5/20* (2006.01)
(Continued)

(52) U.S. Cl.
CPC .............. *G02B 5/201* (2013.01); *A61B 5/0075* (2013.01); *B82Y 20/00* (2013.01); *G01J 3/02* (2013.01); *G01J 3/0205* (2013.01); *G01J 3/36* (2013.01); *G01N 21/554* (2013.01); *G02B 5/204* (2013.01); *A61B 5/0071* (2013.01); *A61B 5/1455* (2013.01); *A61B 2562/0233* (2013.01); *A61B 2562/0285* (2013.01); *A61B 2562/046* (2013.01); *G01J 2003/1213* (2013.01)

(58) Field of Classification Search
None
See application file for complete search history.

(56) References Cited

U.S. PATENT DOCUMENTS

| | | | |
|---|---|---|---|
| 2006/0209413 A1 | 9/2006 | Kim et al. | |
| 2007/0145236 A1* | 6/2007 | Kiesel | G01J 3/02 250/208.1 |
| 2008/0135739 A1 | 6/2008 | Kim et al. | |

FOREIGN PATENT DOCUMENTS

| | | |
|---|---|---|
| JP | 2000-111851 A | 4/2000 |
| JP | 2007-232456 A | 9/2007 |

(Continued)

OTHER PUBLICATIONS

Chang, Cheng-Chun, et al. "On the estimation of target spectrum for filter-array based spectrometers"; Optics Express, vol. 16, No. 2; pp. 1056-1061; Jan. 21, 2008.

(Continued)

*Primary Examiner* — Robert Xu
(74) *Attorney, Agent, or Firm* — The Marbury Law Group PLLC

(57) ABSTRACT

A device such as a filter or reflector includes a conductive layer including a periodic pattern of elements. The elements have shapes and sizes configured such that a transmittance or reflectance spectrum of the conductive layer has a drop at a long-wavelength end. The elements have a period configured such that the spectrum has a dip at a Plasmon mode resonant wavelength. The spectrum further includes a peal—between the dip and the drop.

15 Claims, 47 Drawing Sheets

(51) Int. Cl.
*B82Y 20/00* (2011.01)
*G01J 3/02* (2006.01)
*G01J 3/36* (2006.01)
*G01N 21/552* (2014.01)
*A61B 5/00* (2006.01)
*A61B 5/1455* (2006.01)
*G01J 3/12* (2006.01)

(56) References Cited

FOREIGN PATENT DOCUMENTS

| WO | 2007100112 | A1 | 9/2007 |
| WO | 2008074019 | A2 | 6/2008 |
| WO | 2009/009077 | A3 | 1/2009 |

OTHER PUBLICATIONS

International Preliminary Report on Patentability issued in PCT Application PCT/US2010/027957, mailed on Sep. 29, 2011.

International Search Report and Written Opinion issued in PCT Application PCT/US2010/027957, mailed on Nov. 15, 2010.

Supplementary European Search Report issued in European application No. EP 10754164.1, issued on Oct. 31, 2012.

* cited by examiner

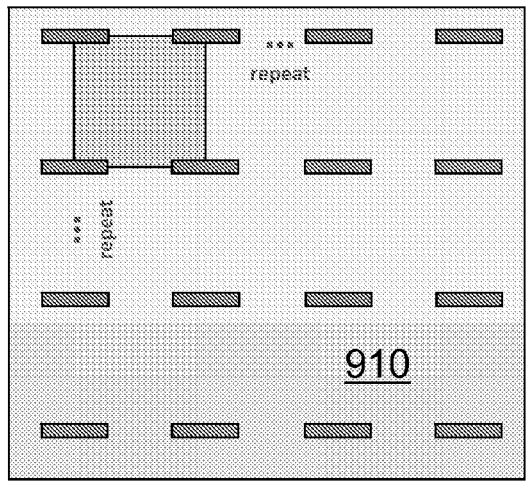
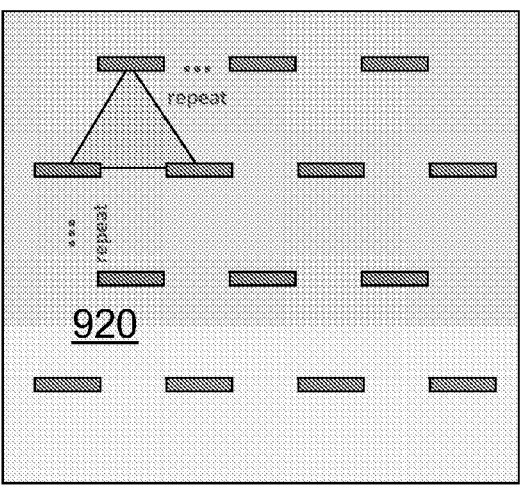
FIG. 9A   FIG. 9B
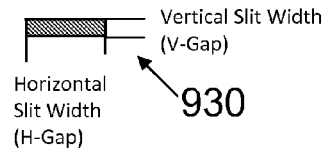
FIG. 9C
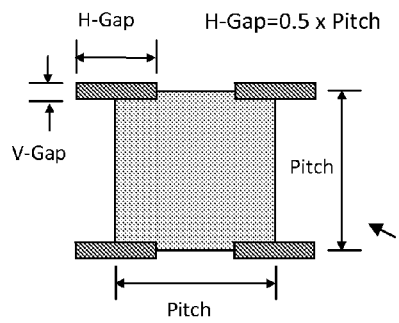
FIG. 9D
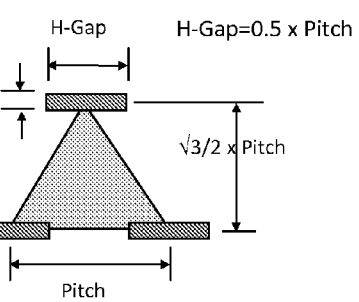
FIG. 9E
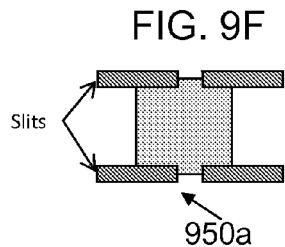
FIG. 9F
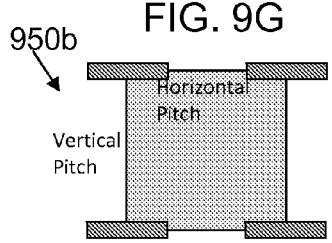
FIG. 9G
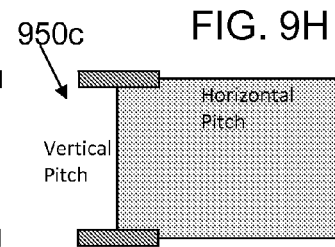
FIG. 9H

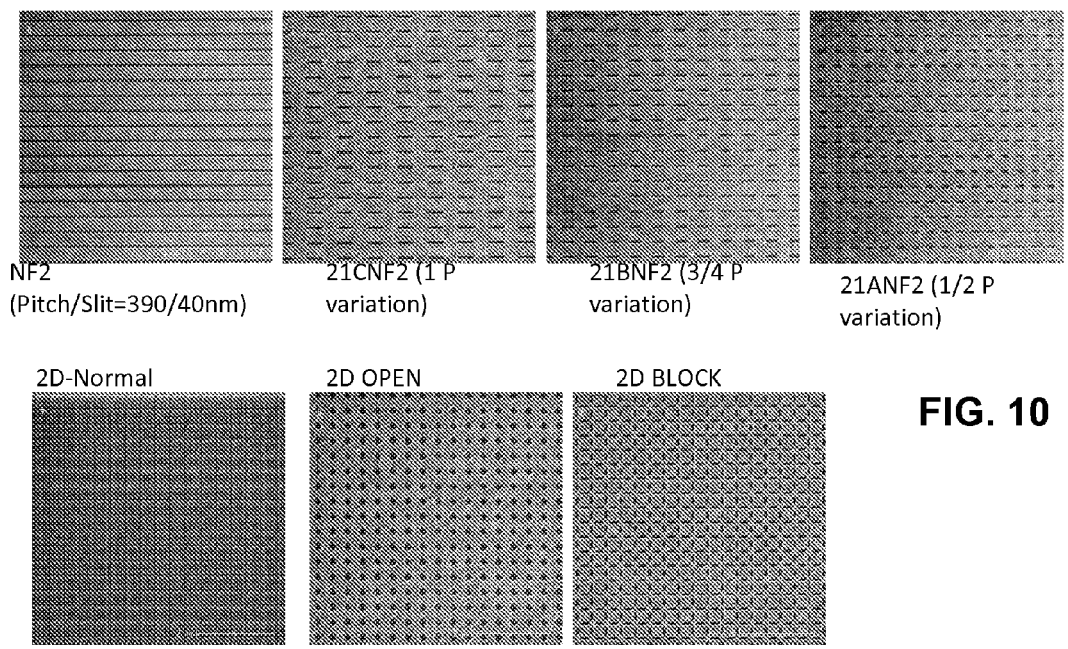
FIG. 10
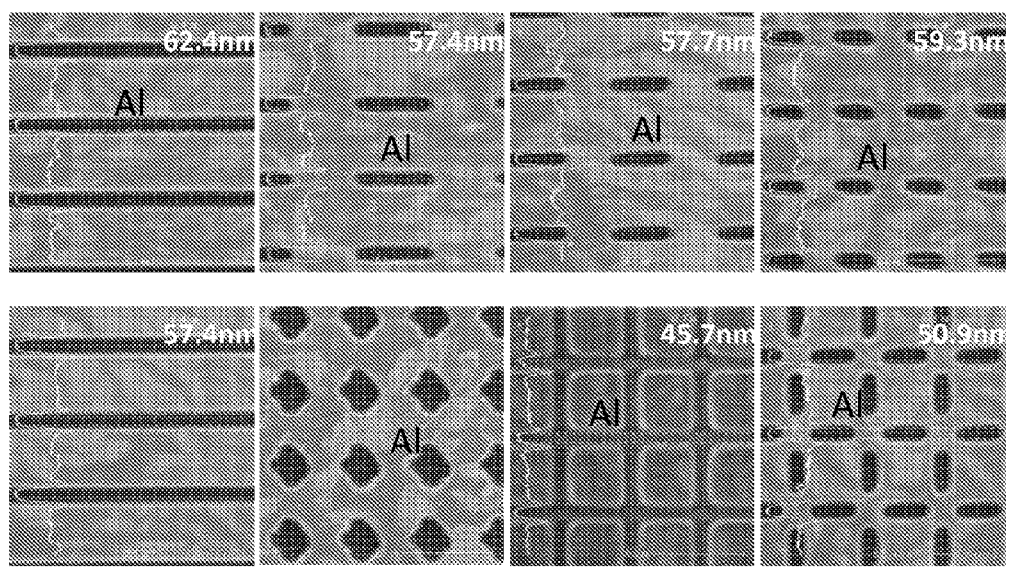

Sample 1-9: H-Pitch vs. $\lambda_p$ $\lambda_{peak}=1.2162x$ (x-Pitch) +72    $\lambda_{peak}=1.72x$ (H. Pitch) +72

- $\lambda$ : 380nm ⇐⇒ 780nm $\Delta\lambda$:400nm
- P: 180nm ⇐⇒ 410nm $\Delta P$:230nm
- ➔23 filter channel of 10nm H.Pitch step ($\Delta\lambda$:17nm)
- ➔46 filter channel of 5nm H.Pitch step ($\Delta\lambda$:8.5nm)

| | Design | | Measured | | X-sec Res | Intensity | SPP$_{(1,0)Al-Qz}$ | dip-1=$n_{Al-Qz}$ x P | Vert Res | Intensity | SPP$_{(1,0)Al-Air}$ | dip-2=$n_{Al-Air}$ x P | a | | b=a/c | |
|---|---|---|---|---|---|---|---|---|---|---|---|---|---|---|---|---|
| V-Pitch | V-Gap | H-Gap | V-Gap | H-Gap | $\lambda_{max(1,1)}$ | $I_{max(1,1)}$ | dip-1 | $n_{Al-Qz}$ | $\lambda_{max(1,0)}$ | $I_{max(1,0)}$ | dip-2 | $n_{Al-air}$ | FWHM | Cut-off(-3d | int of -3dB | C-off/H-G |
| 300 | 40 | 150 | 114.0 | 195.0 | 599 | 0.24 | 470 | 1.57 | 413 | 0.15 | 370? | | 155 | 685 | 0.12 | 3.5 |
| 300 | 40 | 60 | 94.0 | 100.0 | 509 | 0.013 | 430-470 | 1.43 | 400 | | 350? | | 50 | 540 | 0.0065 | 5.4 |
| 300 | 40 | 80 | 100.0 | 122.0 | 519 | 0.047 | 430-480 | 1.43 | 400 | 0.07 | 360? | | 70 | 560 | 0.0235 | 4.6 |
| 300 | 40 | 120 | 110.0 | 170.0 | 562 | 0.166 | 460-490 | 1.53 | 414 | | 360? | | 110 | 620 | 0.083 | 3.6 |
| 300 | 40 | 160 | 106.0 | 206.0 | 616 | 0.247 | 460-500 | 1.53 | 417 | | 360? | | 180 | 715 | 0.1235 | 3.5 |
| | | | average | 158.6 | 561.0 | | | | | | | | | | | |
| | | | stdev | 46.0 | 47.3 | | | | | | | | | | | |

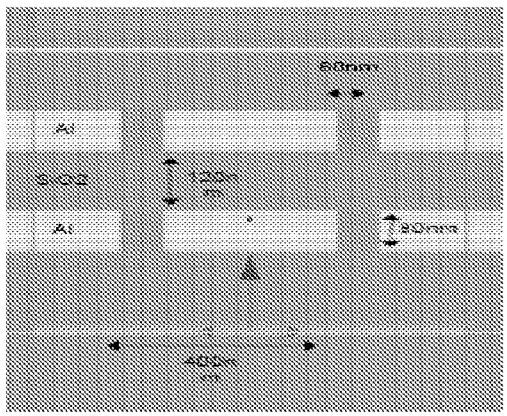
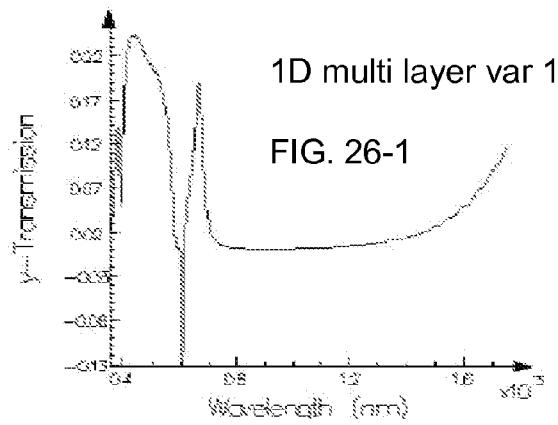
1D multi layer var 1
FIG. 26-1
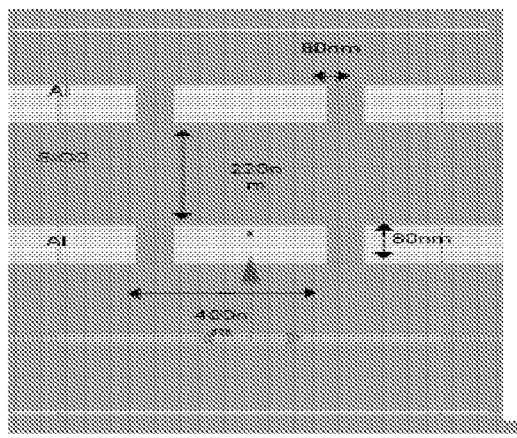
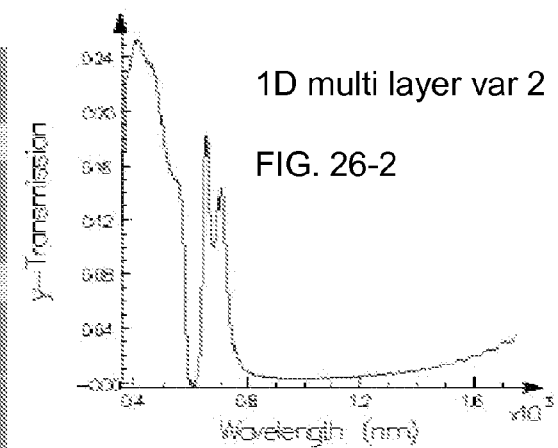
1D multi layer var 2
FIG. 26-2
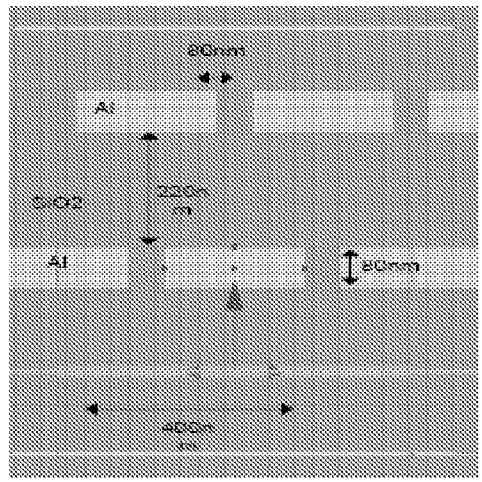
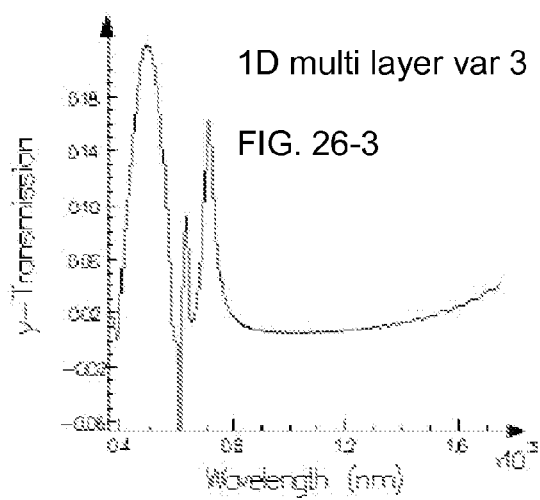
1D multi layer var 3
FIG. 26-3

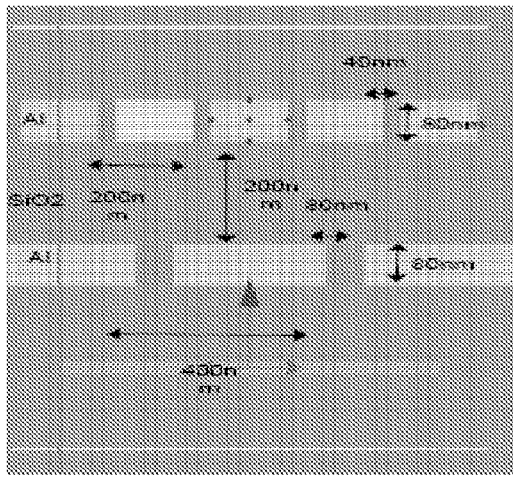
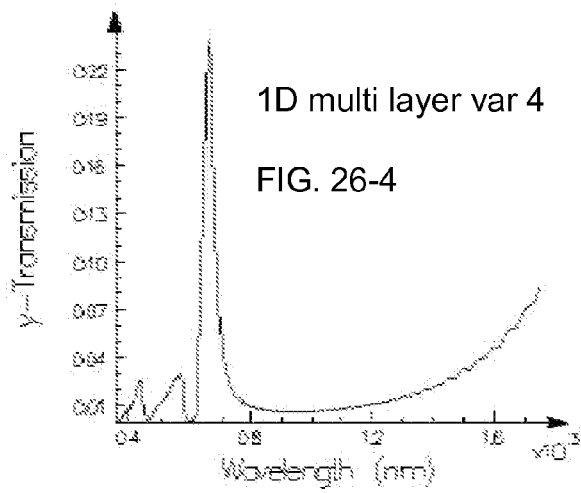
FIG. 26-4
1D multi layer var 4
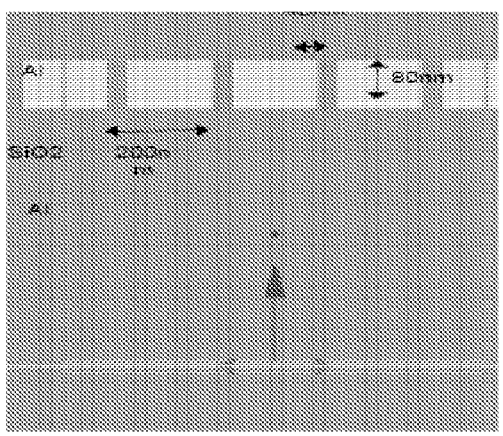
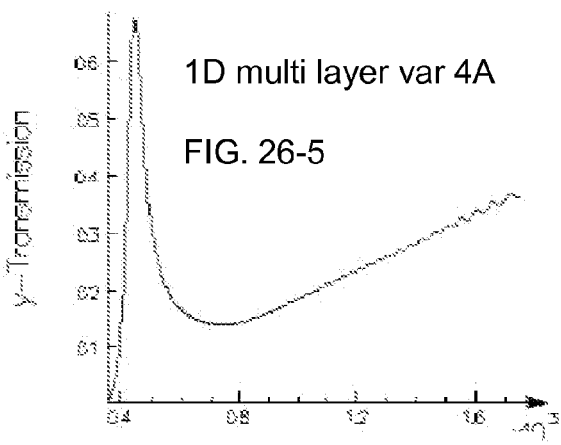
FIG. 26-5
1D multi layer var 4A
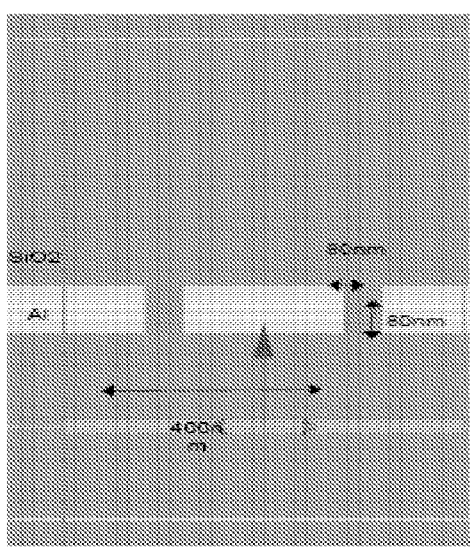
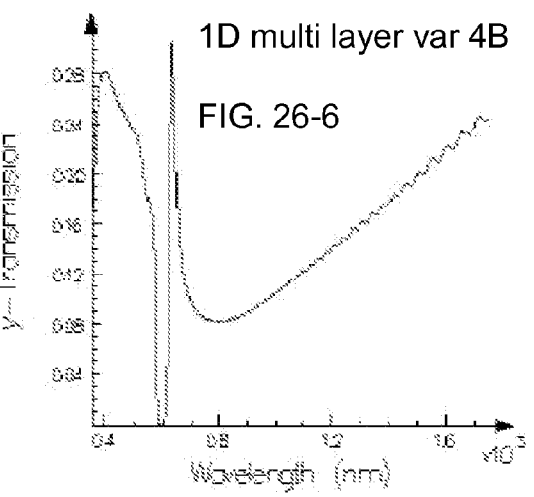
FIG. 26-6
1D multi layer var 4B

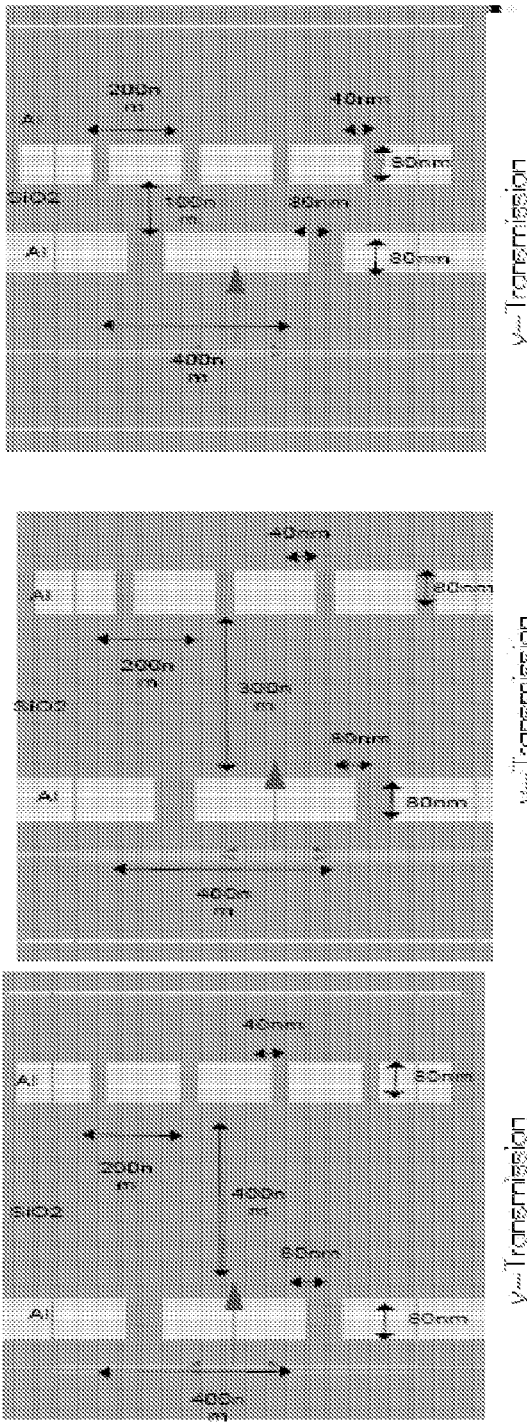
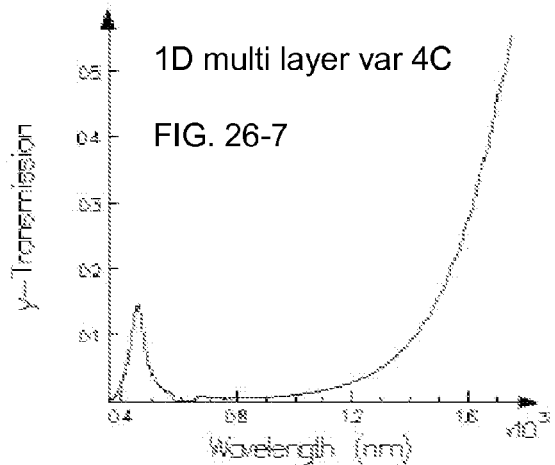
1D multi layer var 4C
FIG. 26-7
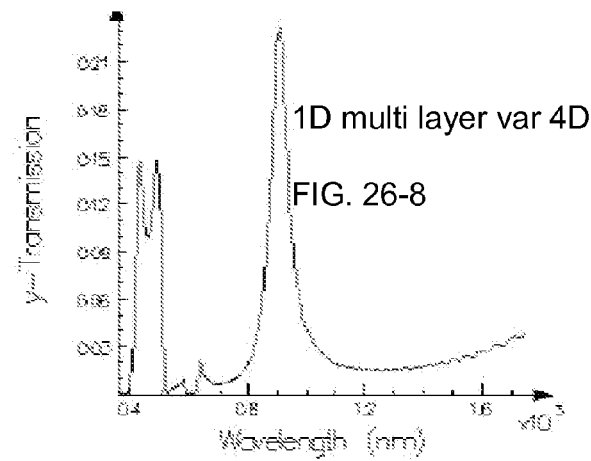
1D multi layer var 4D
FIG. 26-8
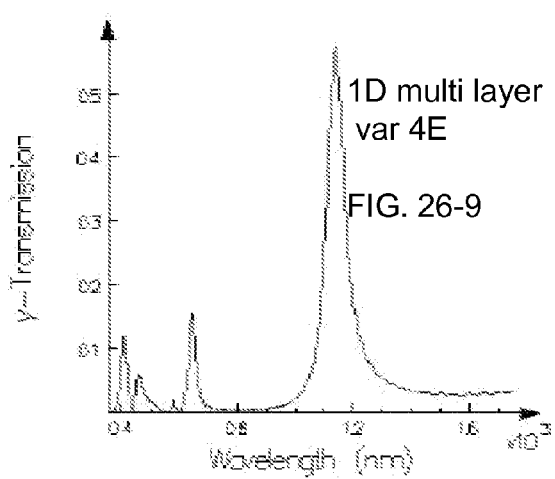
1D multi layer var 4E
FIG. 26-9

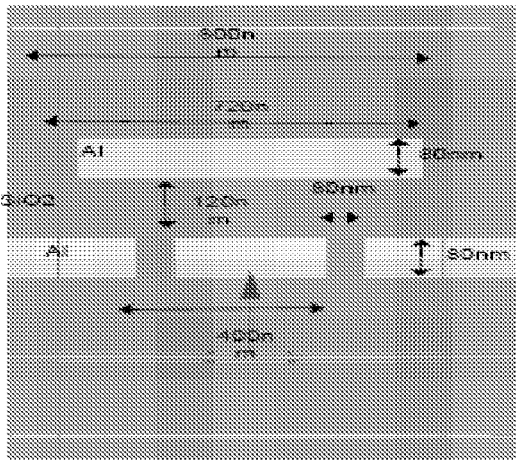 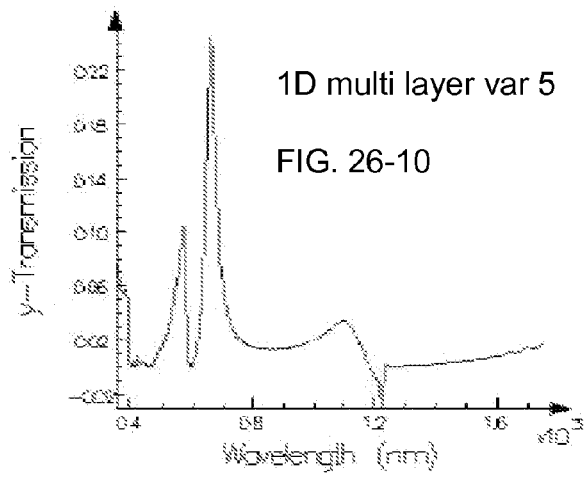
1D multi layer var 5
FIG. 26-10
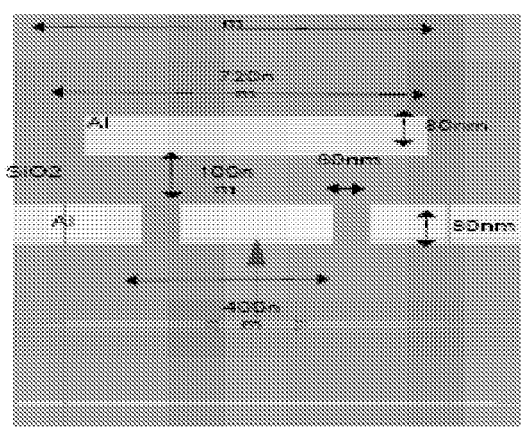 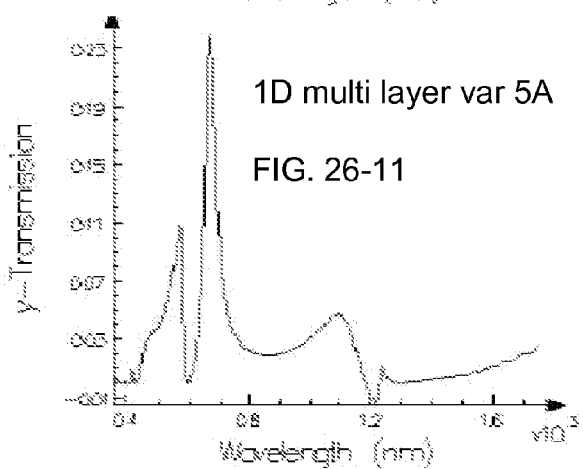
1D multi layer var 5A
FIG. 26-11
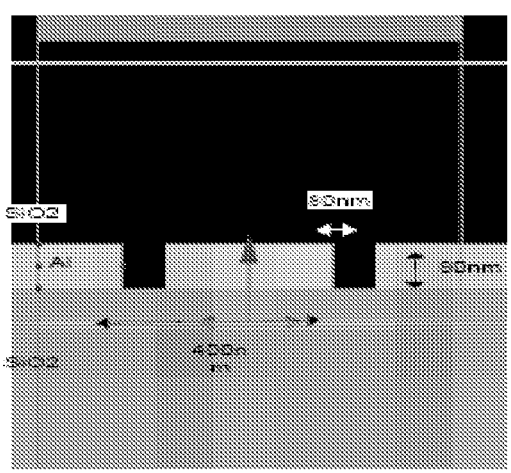 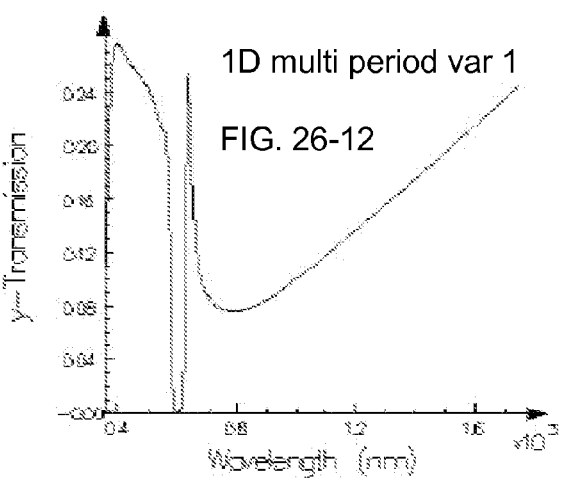
1D multi period var 1
FIG. 26-12

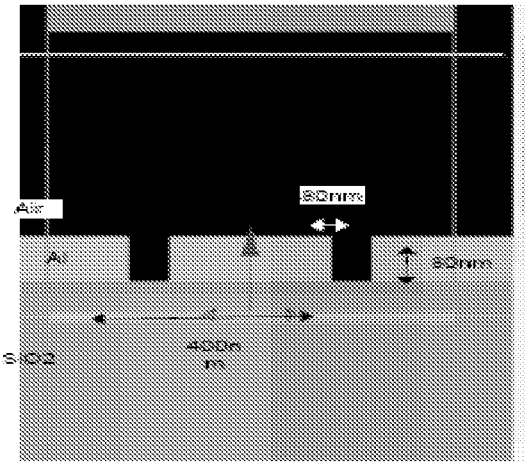
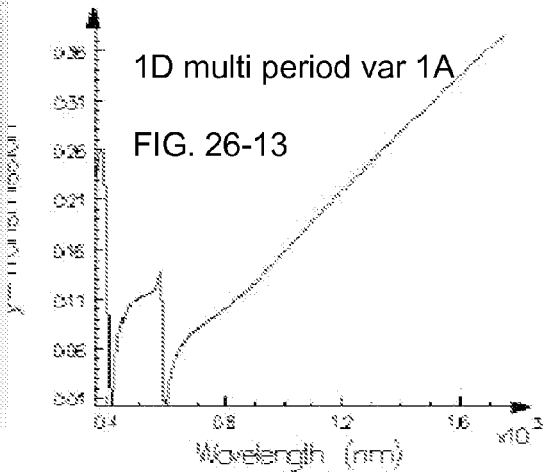
1D multi period var 1A
FIG. 26-13
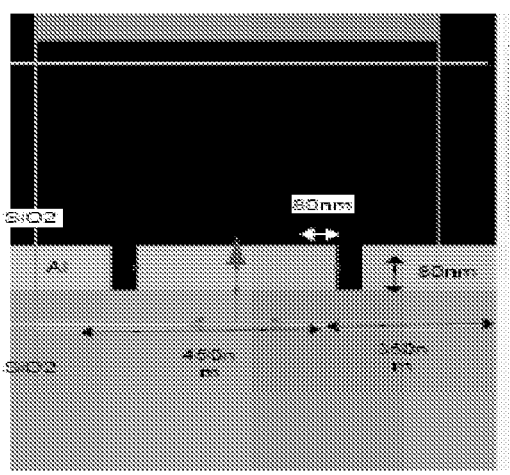
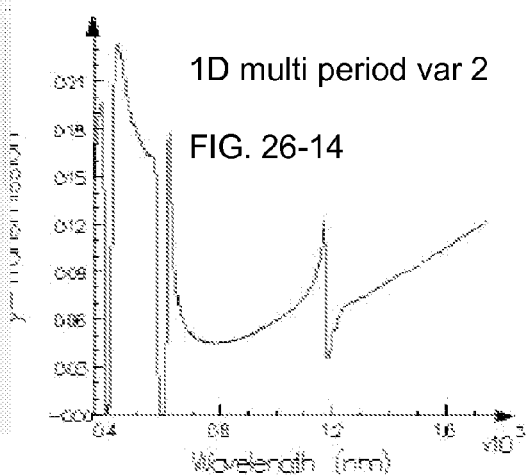
1D multi period var 2
FIG. 26-14
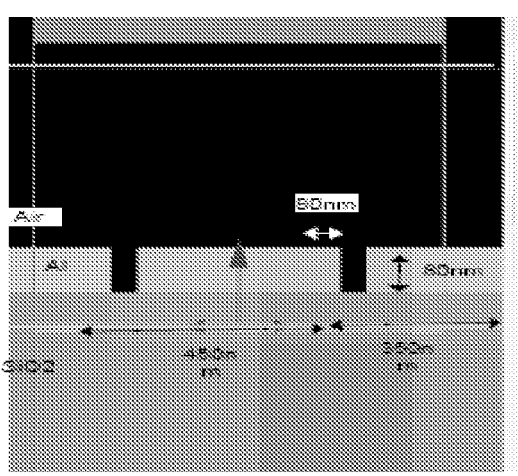
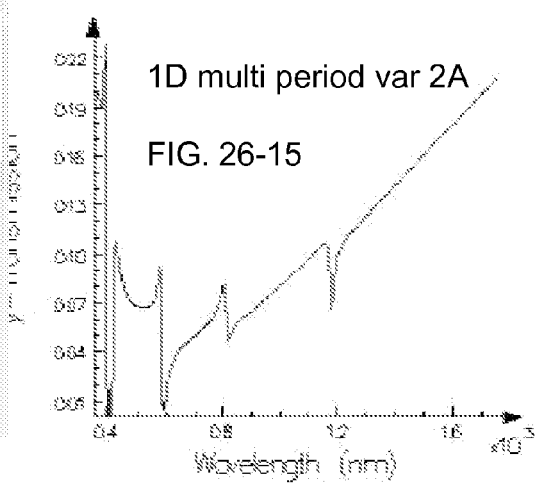
1D multi period var 2A
FIG. 26-15

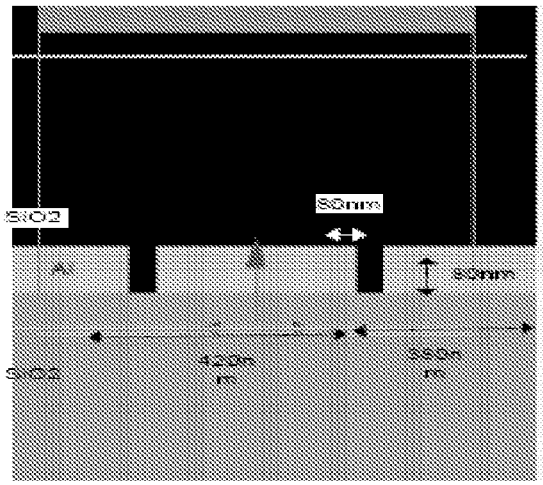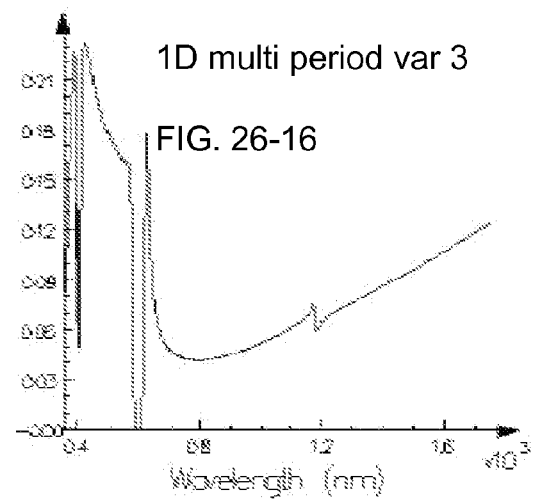
FIG. 26-16 1D multi period var 3
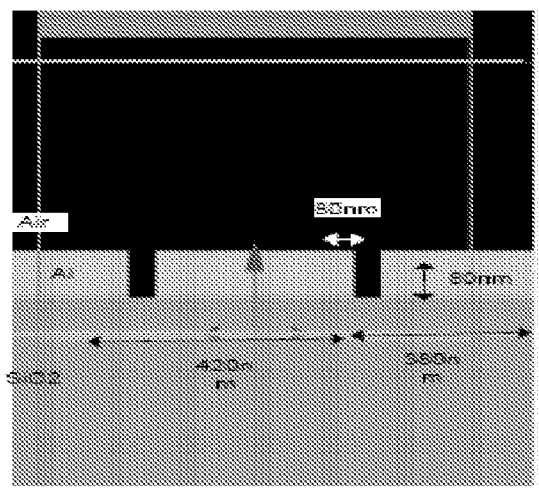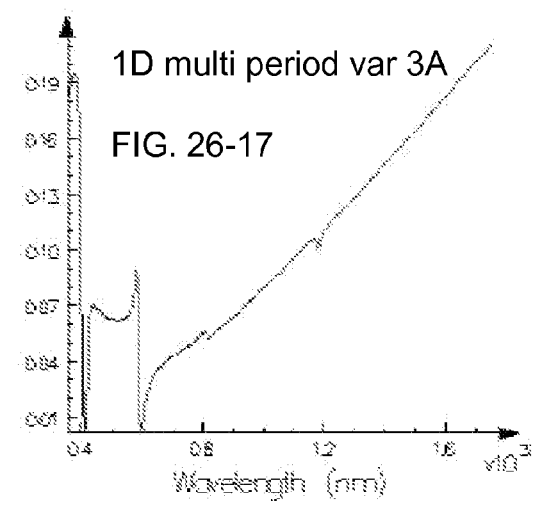
FIG. 26-17 1D multi period var 3A
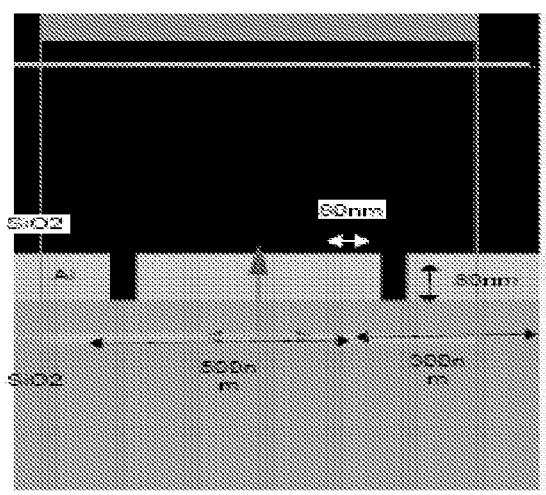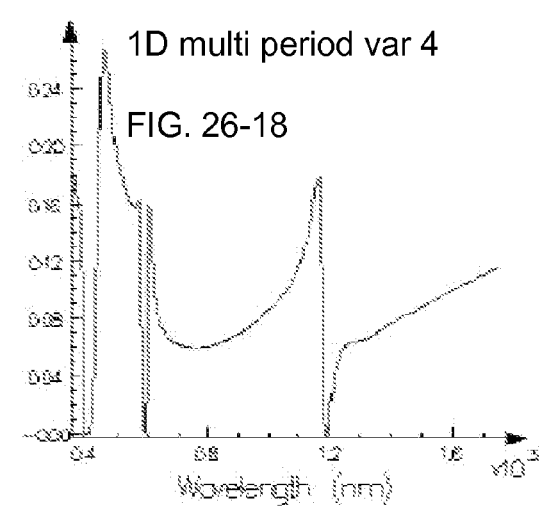
FIG. 26-18 1D multi period var 4

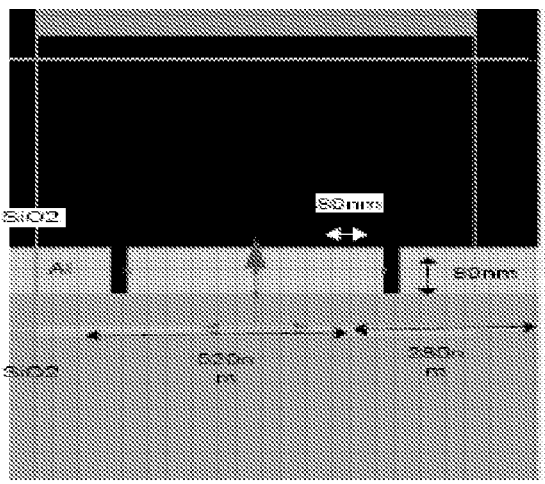 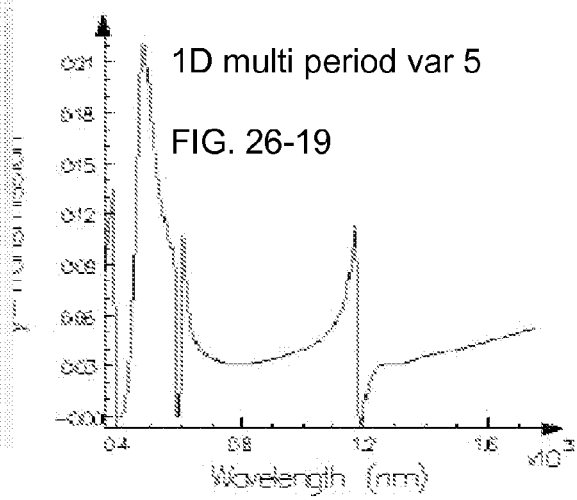
1D multi period var 5
FIG. 26-19
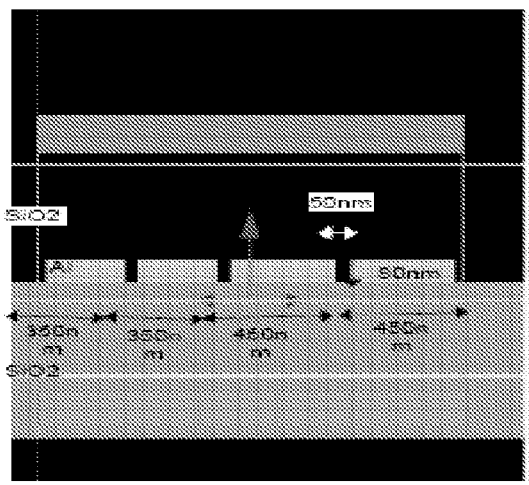 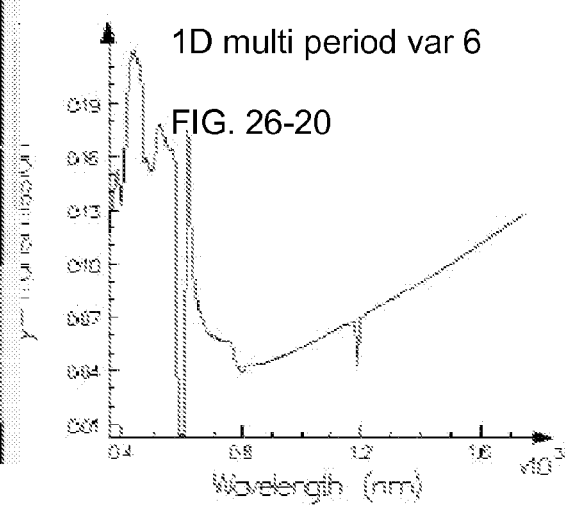
1D multi period var 6
FIG. 26-20
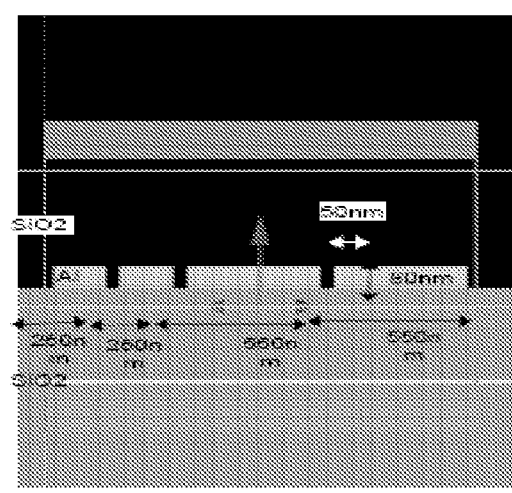 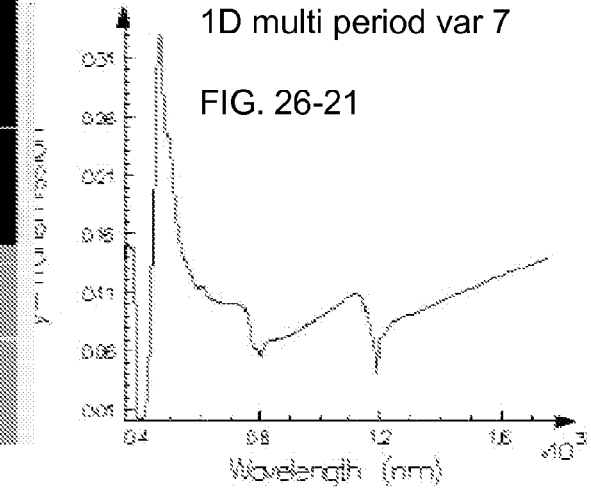
1D multi period var 7
FIG. 26-21

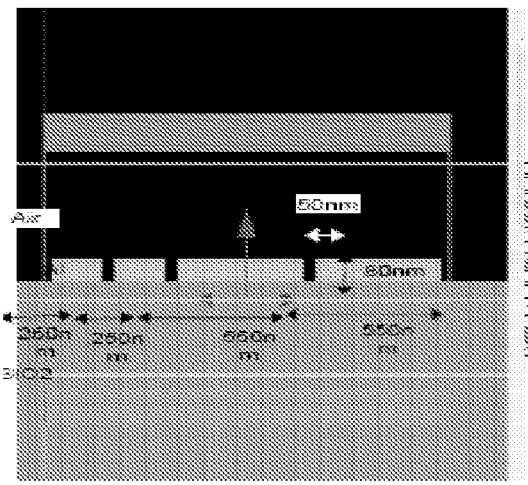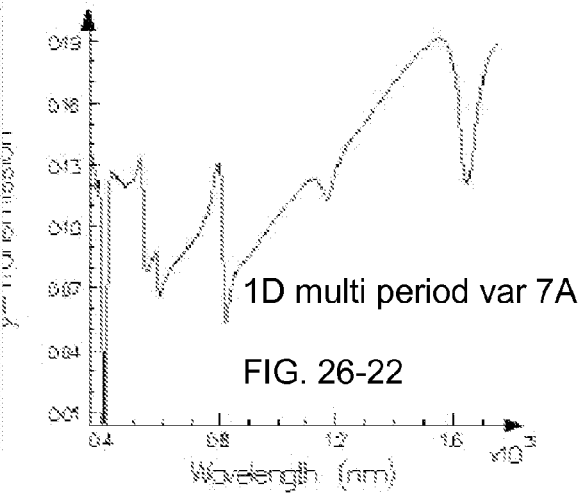
1D multi period var 7A
FIG. 26-22
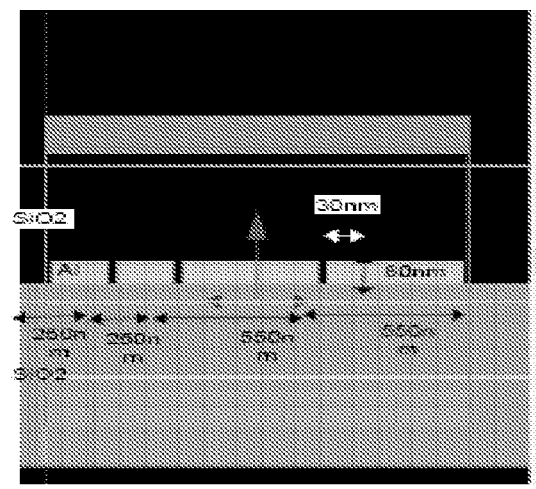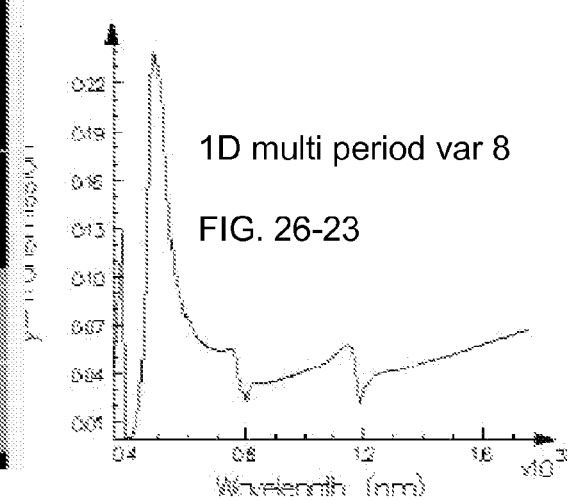
1D multi period var 8
FIG. 26-23
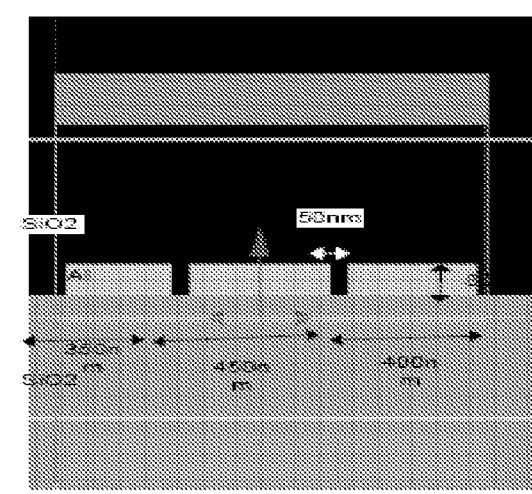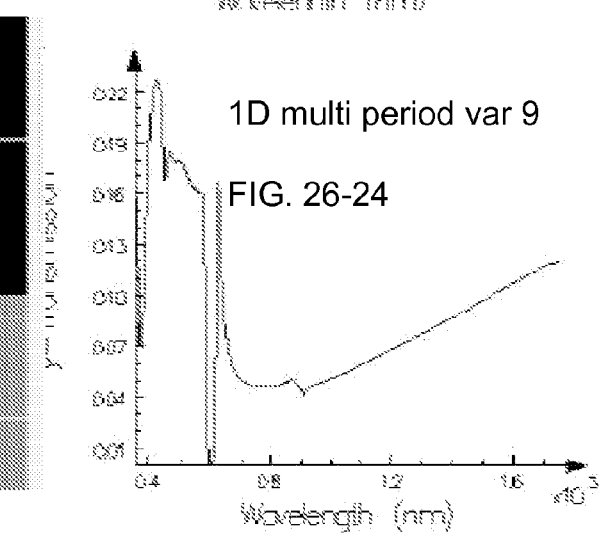
1D multi period var 9
FIG. 26-24

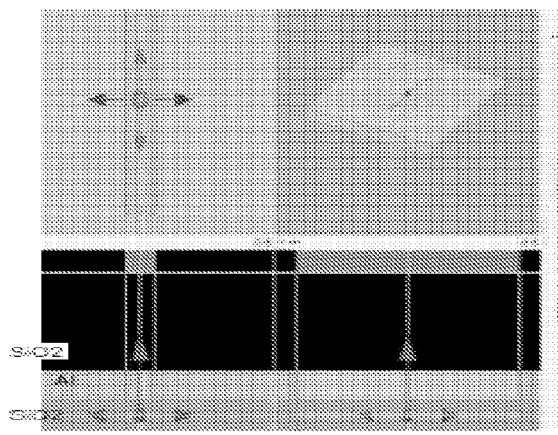
30nm slit/30nm island
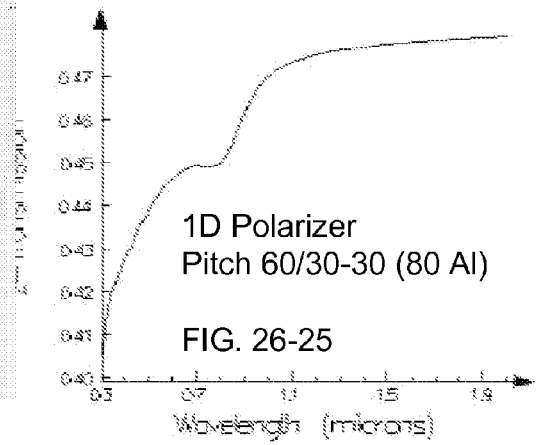
1D Polarizer
Pitch 60/30-30 (80 Al)
FIG. 26-25
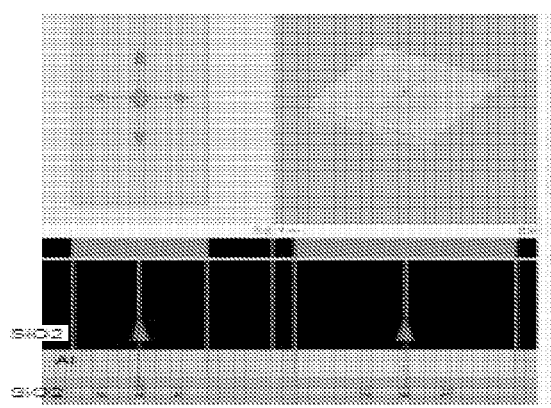
30nm slit/270nm island
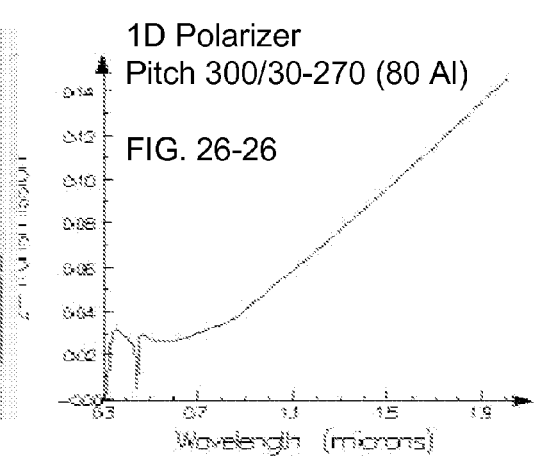
1D Polarizer
Pitch 300/30-270 (80 Al)
FIG. 26-26
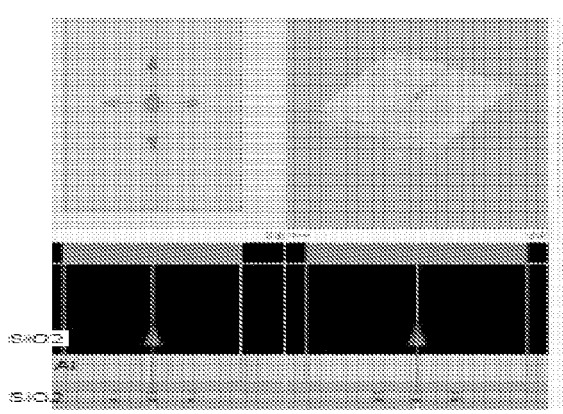
40nm slit/360nm island
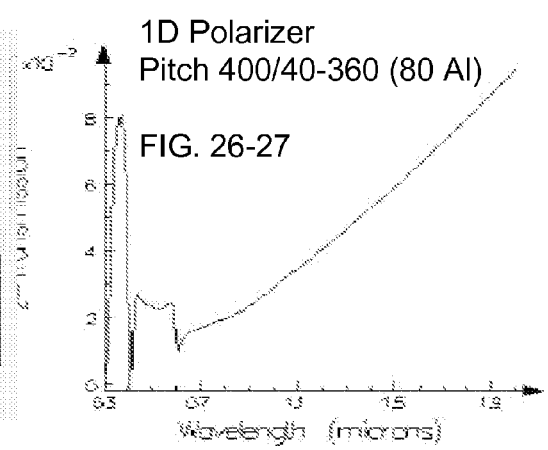
1D Polarizer
Pitch 400/40-360 (80 Al)
FIG. 26-27

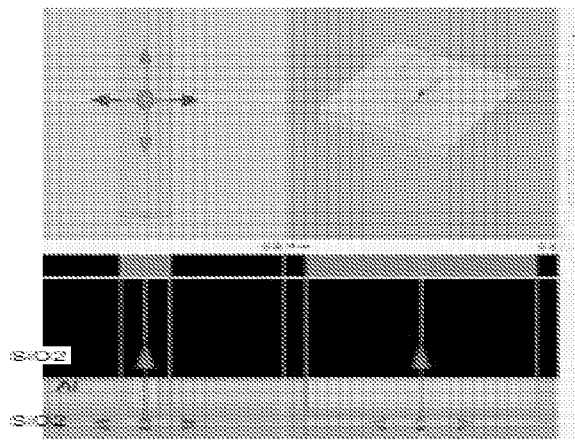
50nm slit/50nm island
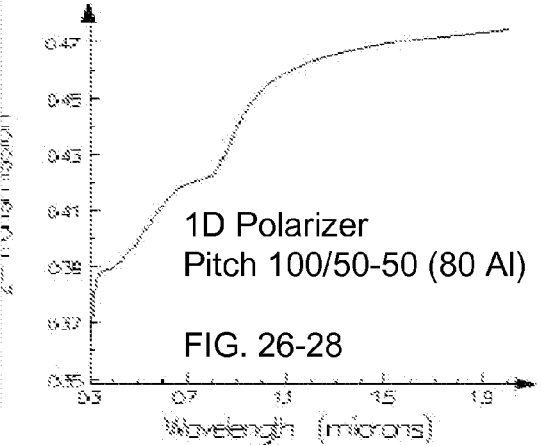
1D Polarizer
Pitch 100/50-50 (80 Al)
FIG. 26-28
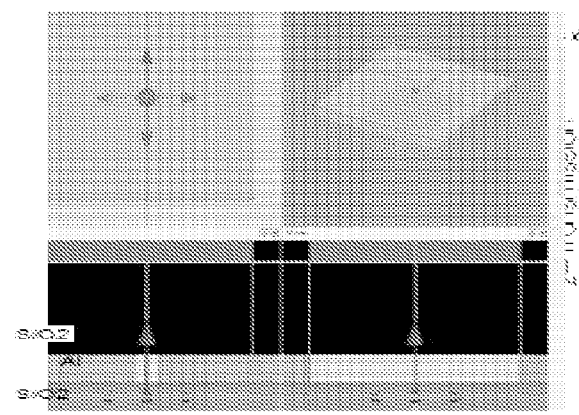
50nm slit/450nm island
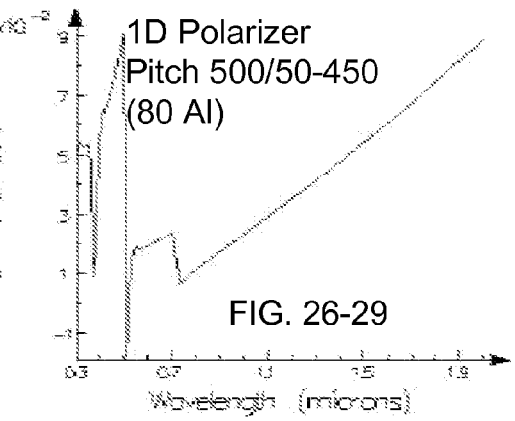
1D Polarizer
Pitch 500/50-450
(80 Al)
FIG. 26-29
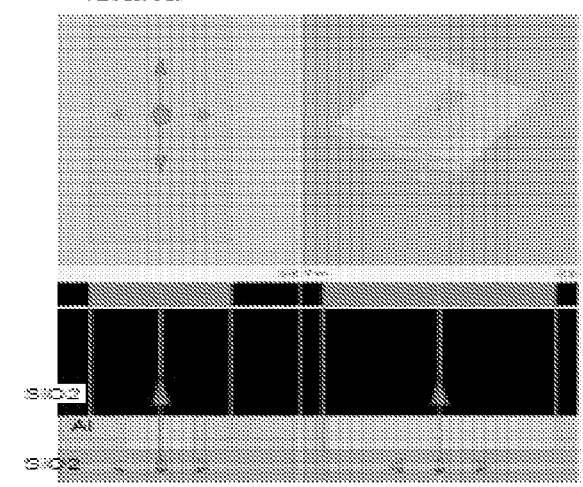
150nm slit/150nm island
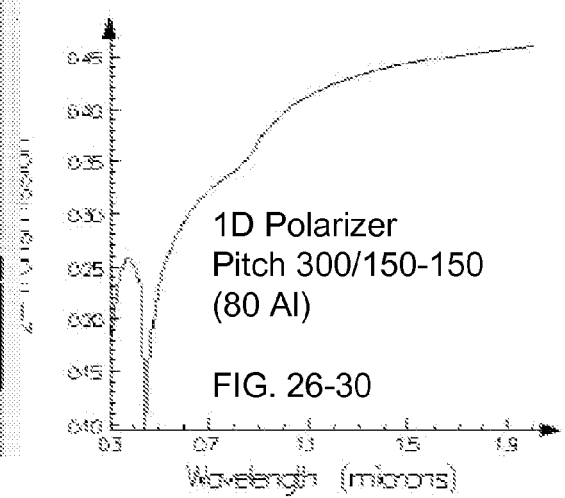
1D Polarizer
Pitch 300/150-150
(80 Al)
FIG. 26-30

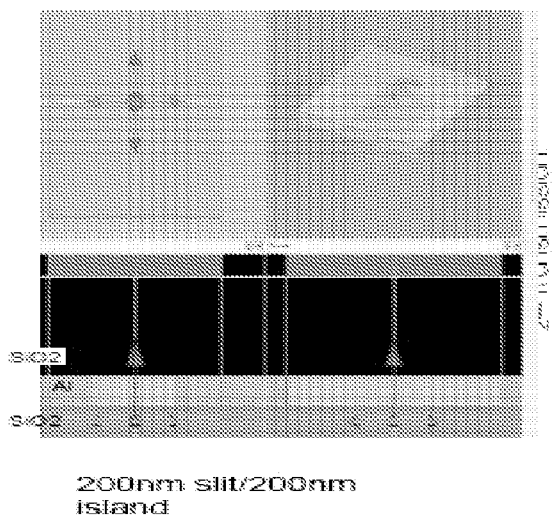
200nm slit/200nm island
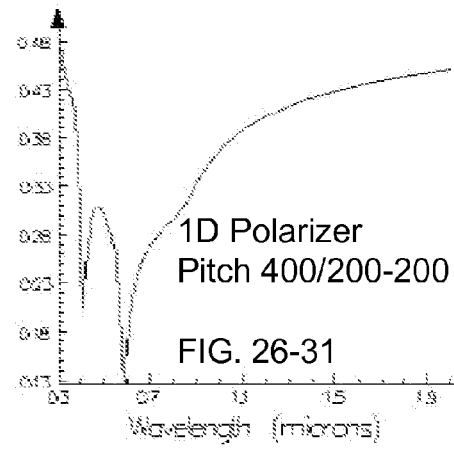
1D Polarizer
Pitch 400/200-200 (80 Al)
FIG. 26-31
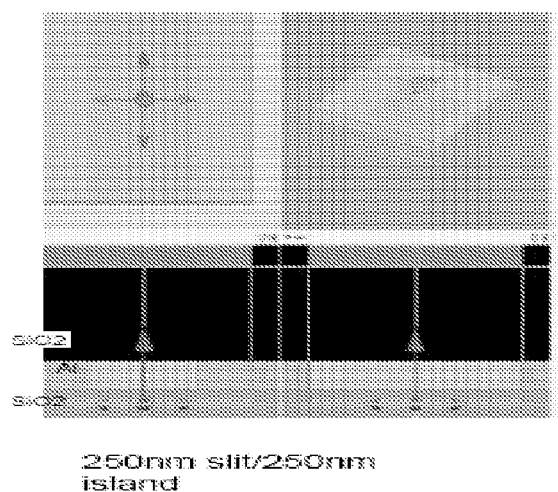
250nm slit/250nm island
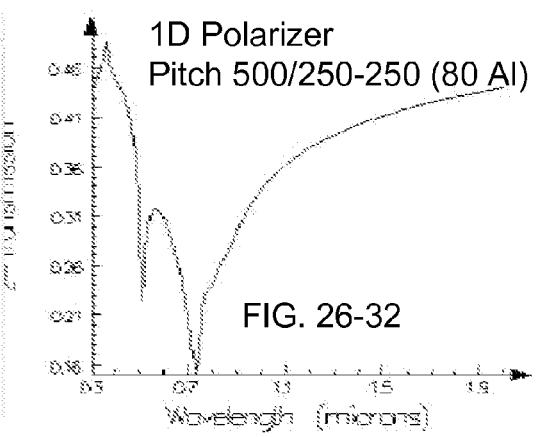
1D Polarizer
Pitch 500/250-250 (80 Al)
FIG. 26-32
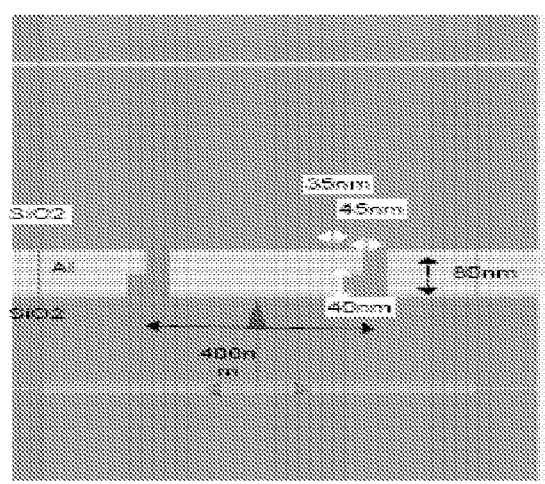
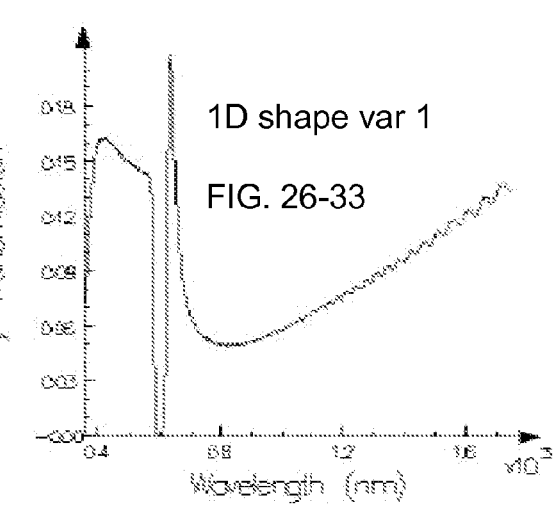
1D shape var 1
FIG. 26-33

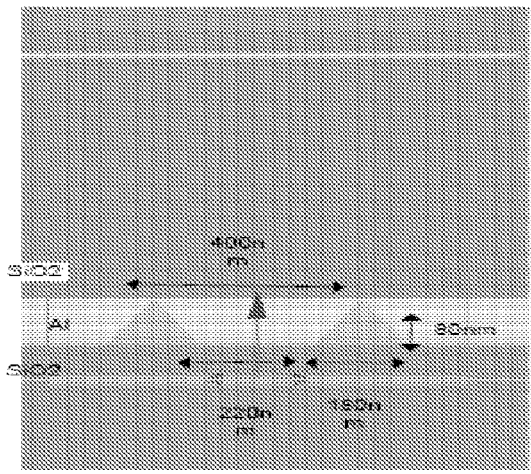
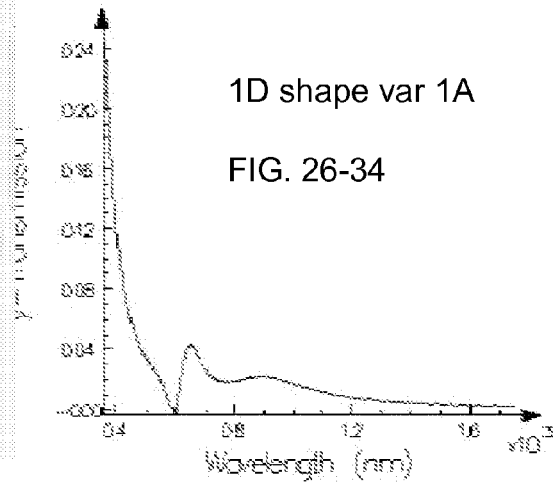
1D shape var 1A
FIG. 26-34
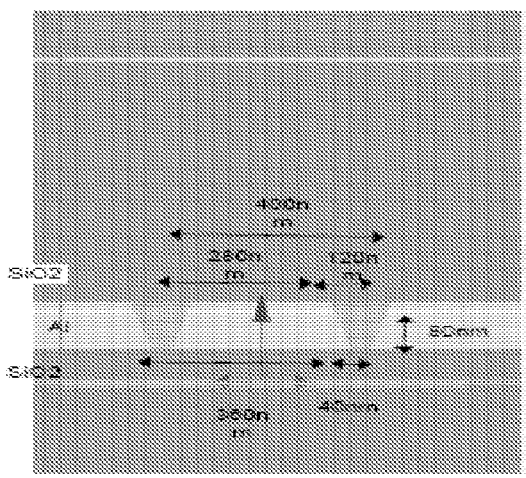
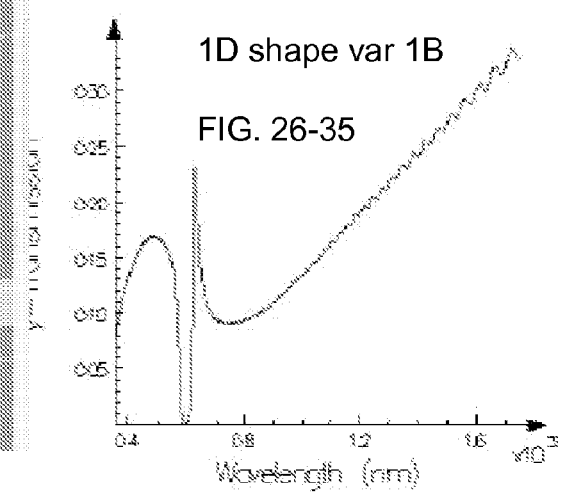
1D shape var 1B
FIG. 26-35
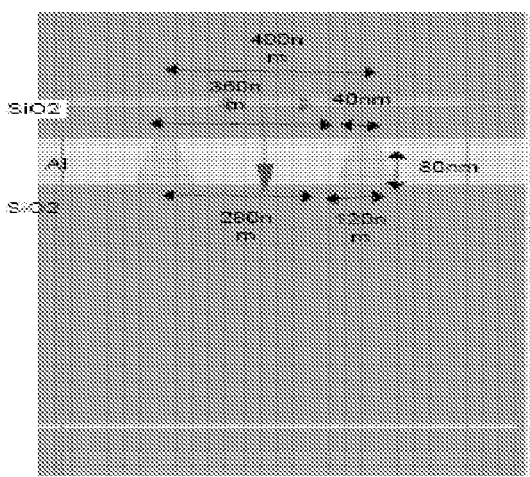
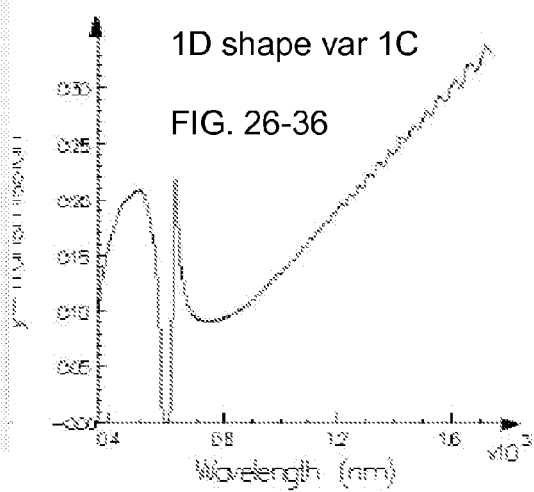
1D shape var 1C
FIG. 26-36

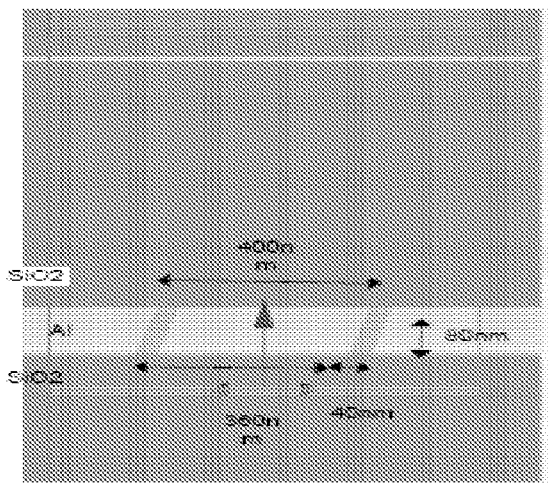 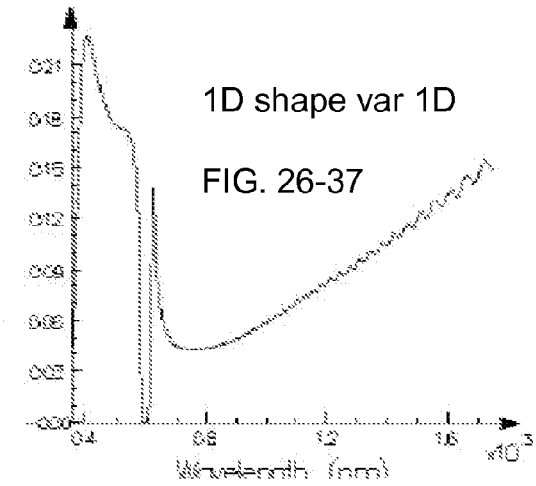
1D shape var 1D
FIG. 26-37
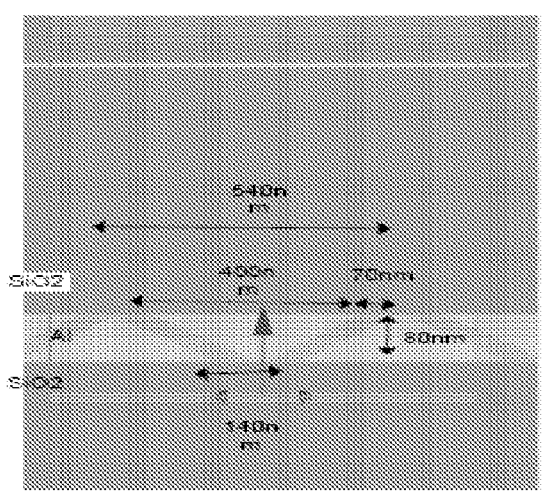 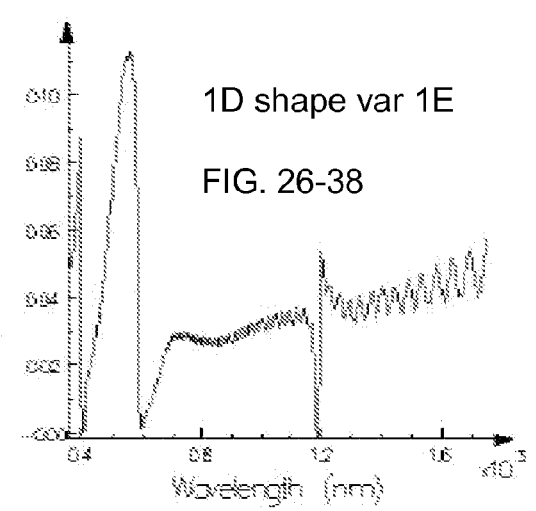
1D shape var 1E
FIG. 26-38
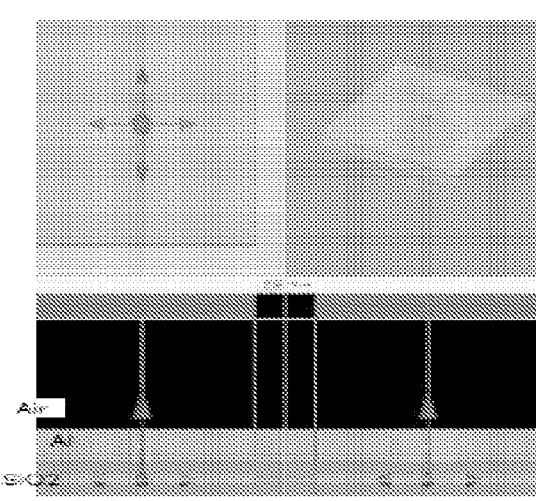 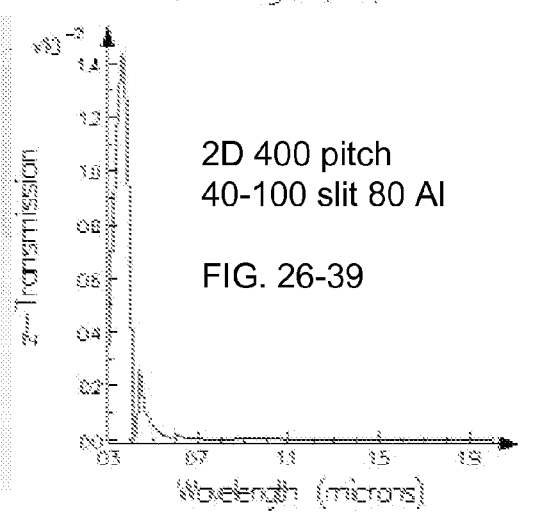
2D 400 pitch
40-100 slit 80 Al
FIG. 26-39

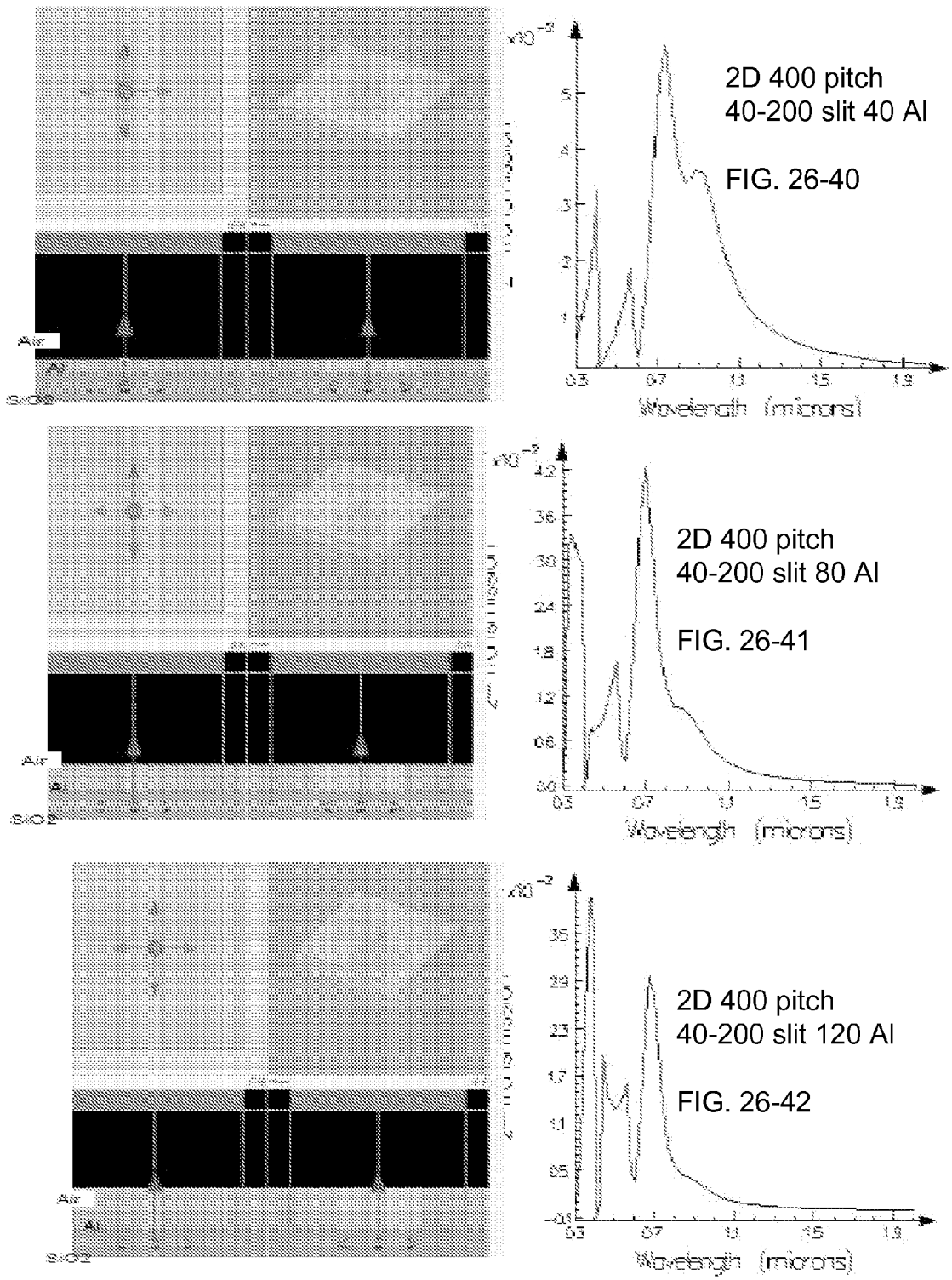
FIG. 26-40 — 2D 400 pitch 40-200 slit 40 Al
FIG. 26-41 — 2D 400 pitch 40-200 slit 80 Al
FIG. 26-42 — 2D 400 pitch 40-200 slit 120 Al

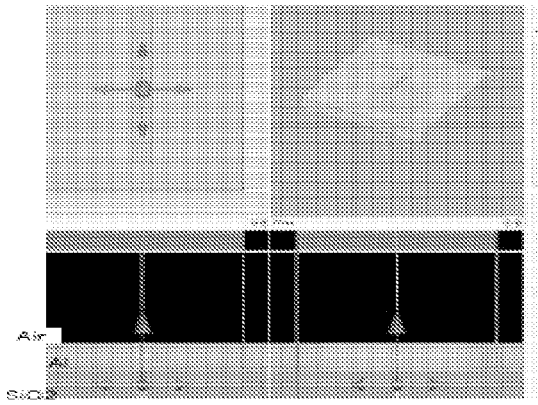 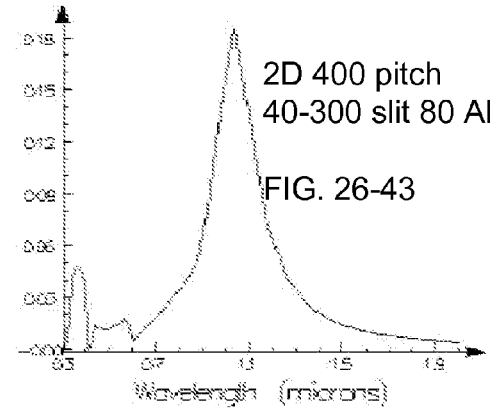
2D 400 pitch
40-300 slit 80 Al
FIG. 26-43
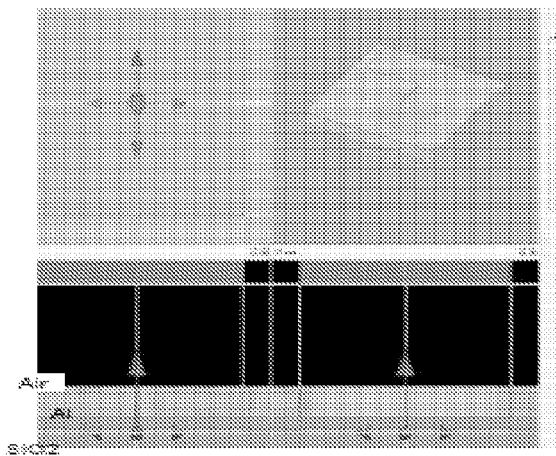 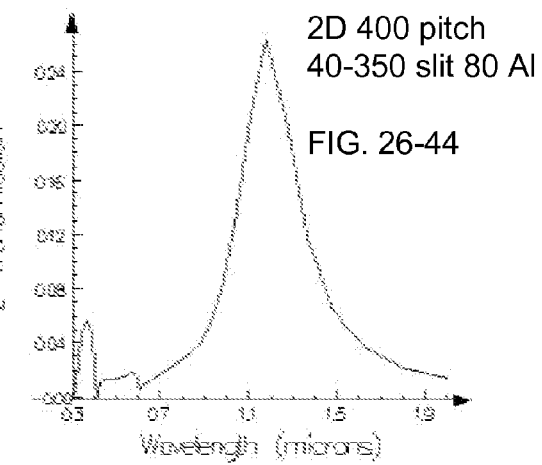
2D 400 pitch
40-350 slit 80 Al
FIG. 26-44
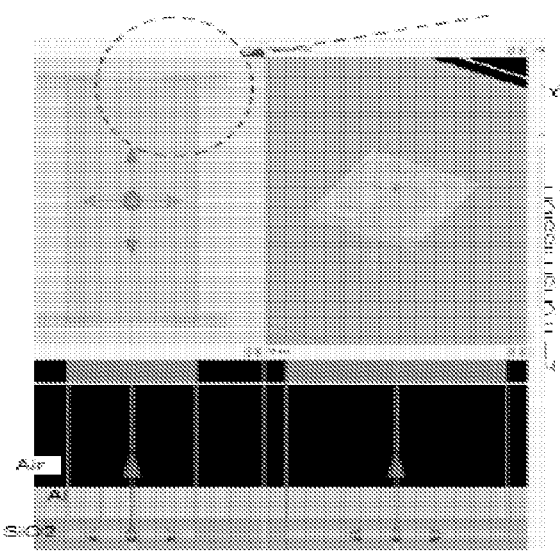 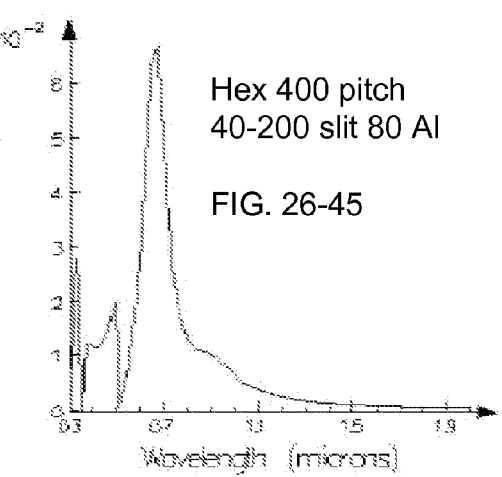
Hex 400 pitch
40-200 slit 80 Al
FIG. 26-45

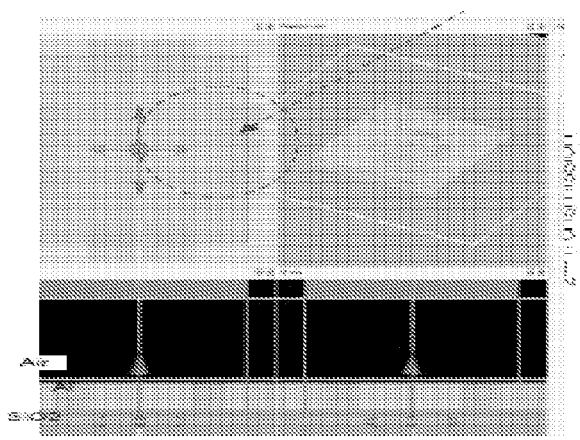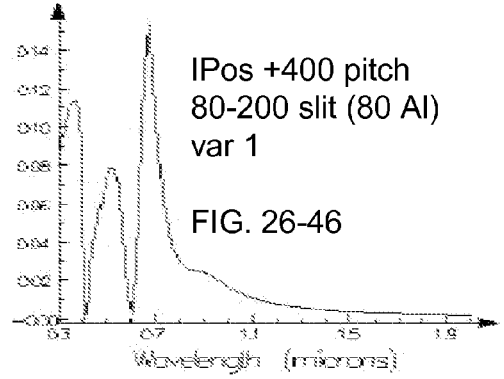
IPos +400 pitch
80-200 slit (80 Al)
var 1
FIG. 26-46
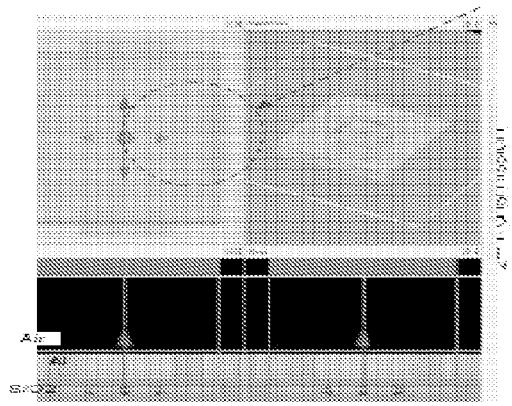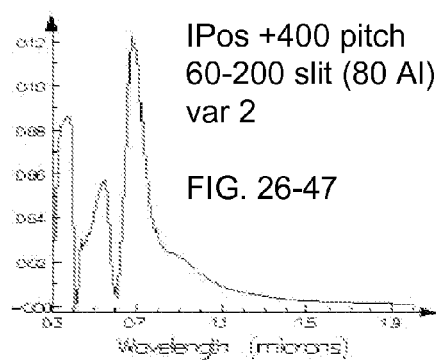
IPos +400 pitch
60-200 slit (80 Al)
var 2
FIG. 26-47
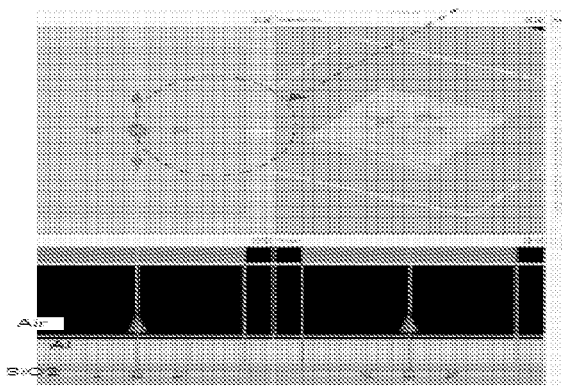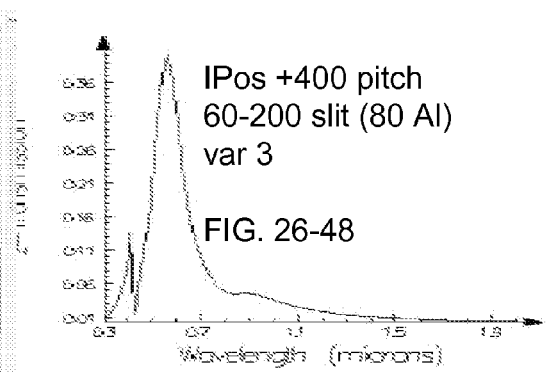
IPos +400 pitch
60-200 slit (80 Al)
var 3
FIG. 26-48

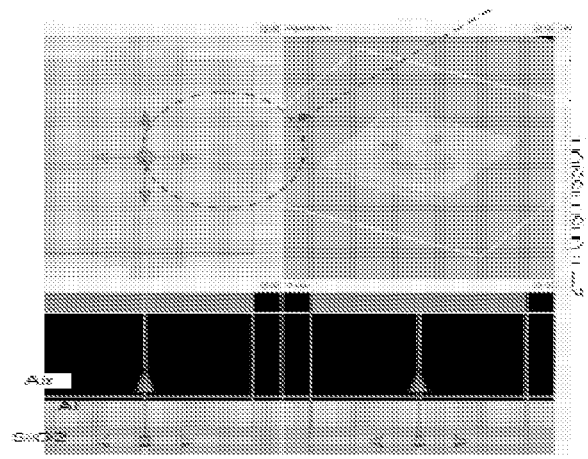
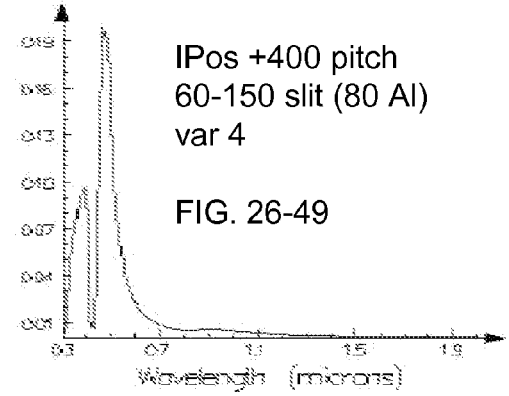
IPos +400 pitch
60-150 slit (80 Al)
var 4
FIG. 26-49
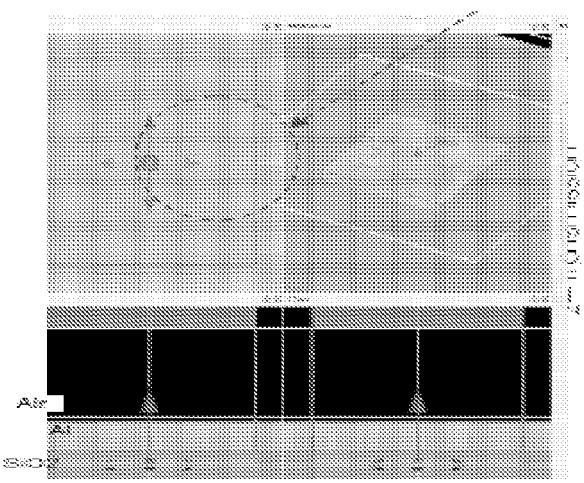
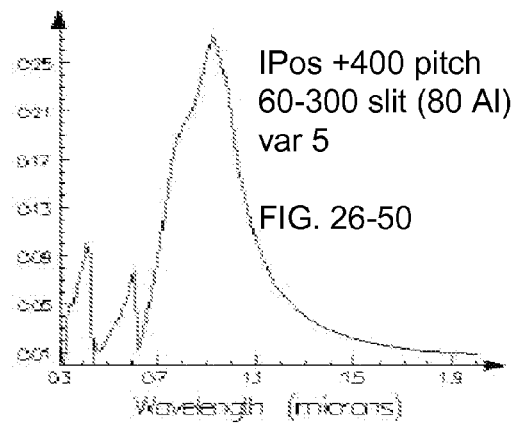
IPos +400 pitch
60-300 slit (80 Al)
var 5
FIG. 26-50
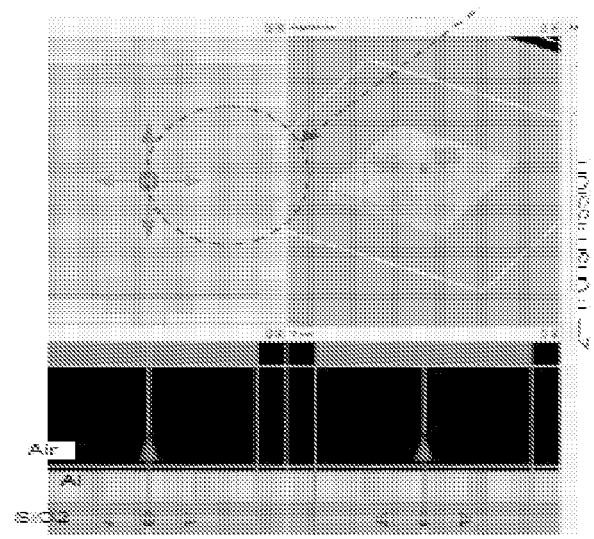
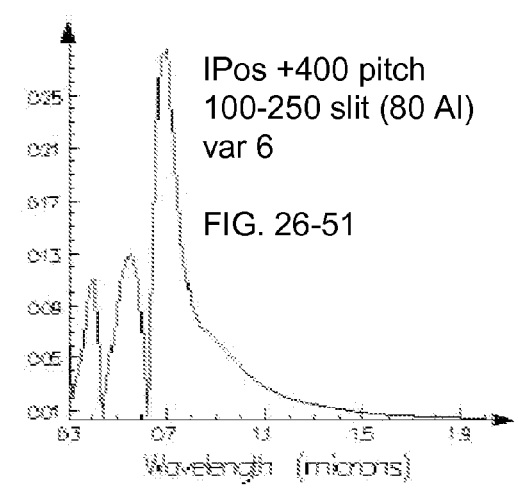
IPos +400 pitch
100-250 slit (80 Al)
var 6
FIG. 26-51

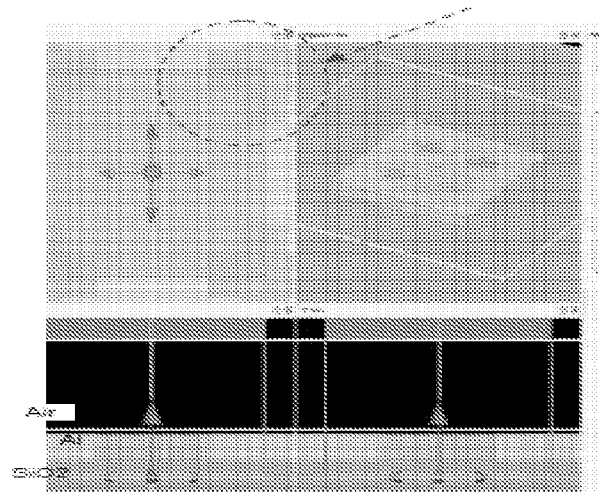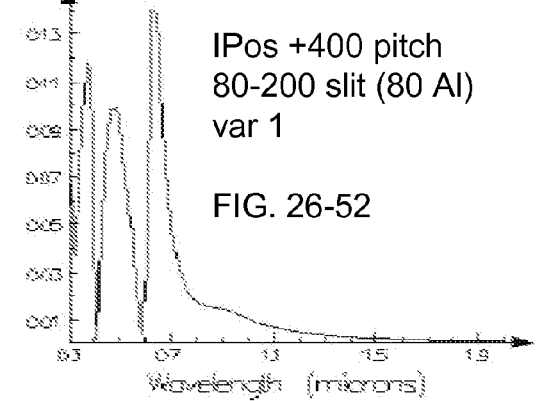
IPos +400 pitch
80-200 slit (80 Al)
var 1
FIG. 26-52
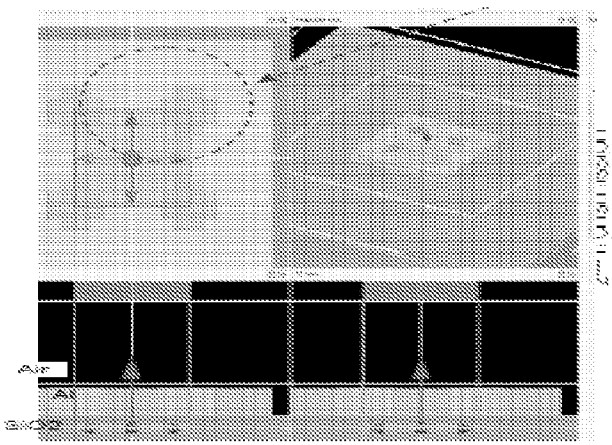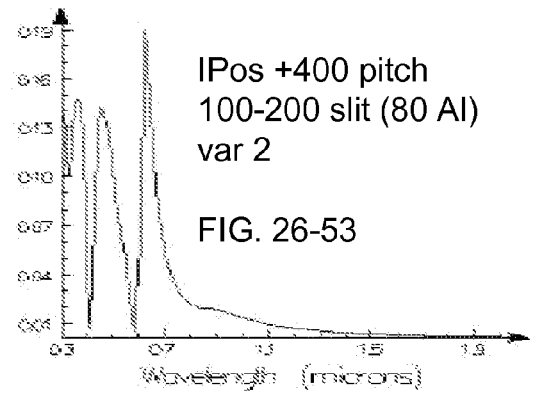
IPos +400 pitch
100-200 slit (80 Al)
var 2
FIG. 26-53
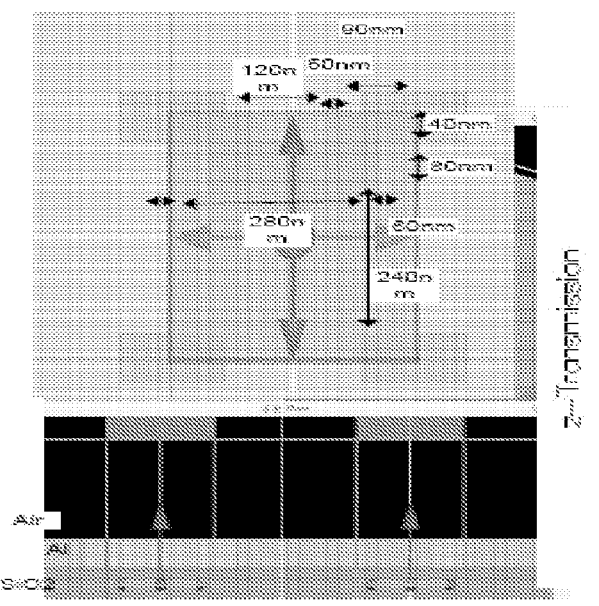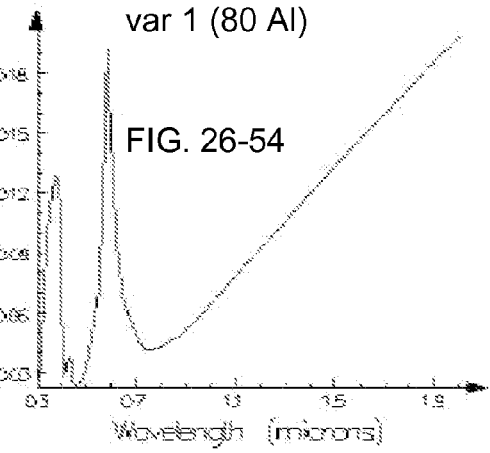
Zigzag(b) 400 pitch
var 1 (80 Al)
FIG. 26-54

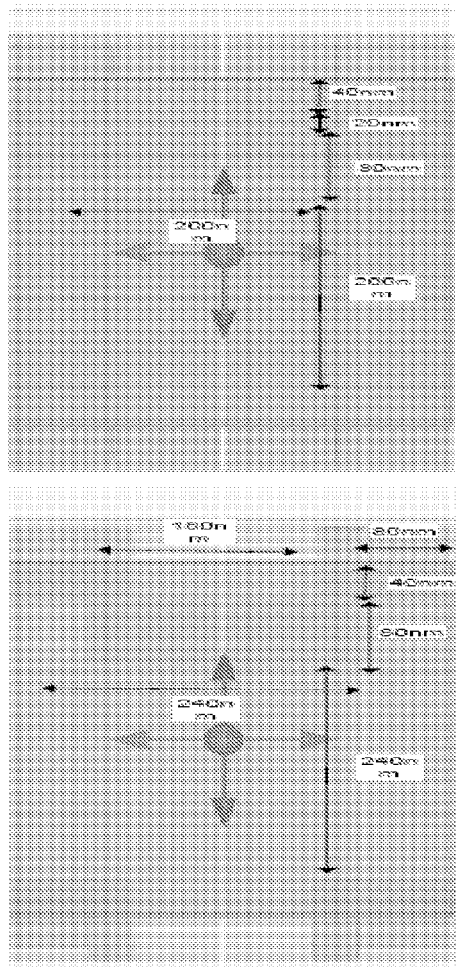
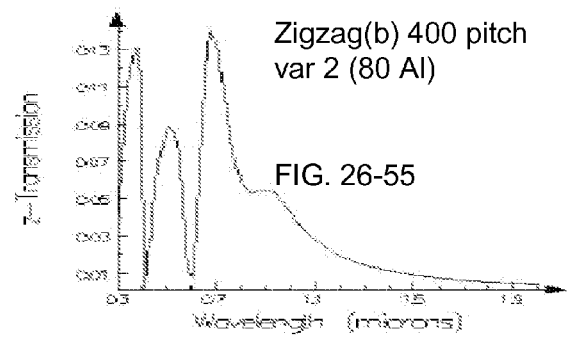
Zigzag(b) 400 pitch
var 2 (80 Al)
FIG. 26-55
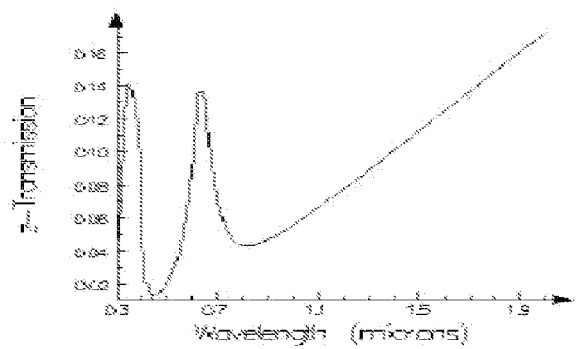
Zigzag(c) 400 pitch
var 2 (80 Al)
FIG. 26-56

NANO-OPTIC FILTER ARRAY BASED SENSOR

The present application is a national phase entry of international application PCT/US10/27957, and claims priority to U.S. Provisional Patent Application Ser. No. 61/161,892, filed Mar. 20, 2009, the disclosure of which is hereby incorporated by reference in its entirety.

BACKGROUND OF THE INVENTION

Optical spectroscopy technology has been widely used to detect, quantify and analyze the characteristics or concentration of a physical, chemical or biological target object such as a blood sample. This technology can also be used in other in vivo chemometric analyses of chemical components of tissues or organs in a living organism. A variety of spectral techniques involve absorption, transmission, reflection, emission, and scattering (including elastic and non-elastic) of radiations applied to a target sample. The radiations used span over a wide range and include UV, Visual, NIR (Near Infrared), SWIR (Short-Wavelength Infrared), MWIR (Medium-Wavelength Infrared), and LWIR (Long-Wavelength Infrared) light.

Optical spectroscopy is also used for highly accurate color measurement of various colored materials. Advanced techniques are used for clinical quantification of blood glucose, dissolved oxygen, dissolved carbon dioxide, urea, lactic acid, creatine, bicarbonate, electrolytes, protein, albumin, cholesterol, triglycerides, bilirubin, heart rate, breathing rate, hematocrit, and hemoglobin.

Optical diagnostics using optical spectroscopy allows for the ability to obtain chemical and biological information without taking a physical specimen, or the ability to obtain information in a non-invasive or non-destructive method from a physical specimen. The challenge is that the adoption of this technology has been limited due to the size of the equipment and the associated cost. Therefore, its application has often been limited to centralized labs with scaled testing protocols. The opportunity now exists to develop a compact and low cost spectrometer. Among those previous efforts to miniaturize the spectrometer to expand the application of optical spectroscopy into broader uses, the planar waveguide-based, grating-based, and Fabry-Perot-based techniques have been the major approaches.

One of the issues encountered when trying to miniaturize the spectrometer is the resolution degradation. The resolution is usually dominated by the optics, especially by the distance from the input slit where the input light comes into the system to the detector array such as a photo diode array (PDA). The shorter the distances, the higher the resolution degradation will be. When filters are used, the number of the filters, and the shape or bandwidth (often measured in terms of FWHM—Full Width Half Maximum) of each filter dominate the degradation. A larger number of filters and a narrower FWHM would provide a higher resolution. However, there is a certain limitation to how narrow the bandwidths of the filters can be, especially when these filters are fabricated in an array configuration.

There are some other issues in using these optical spectroscopy technologies. For example, Berger et al. (U.S. Pat. No. 5,615,673) and Yang et al. (U.S. Pat. No. 6,167,290) each describe a Raman spectroscopic system designed for transdermal analysis of blood components. Xie (U.S. Patent Application Publication No. 2005/0043597) describes a spectral analysis system for analyzing blood components using a radiation passing through a nail of a finger or toe. In these systems, individual variation in skin or nail properties and in blood vessel placement can significantly affect the accuracy of the measurements.

SUMMARY OF THE INVENTION

Embodiments disclosed herein employ nano-optic devices and neural-network-based pattern recognition techniques to improve the miniaturized spectral sensing.

In one embodiment, a device is provided comprising a conductive layer including a periodic pattern of elements. The elements have shapes and sizes configured such that a transmittance or reflectance spectrum of the conductive layer has a drop at a long-wavelength end. The elements have a period configured such that the spectrum has a dip at a Plasmon mode resonant wavelength. The spectrum further includes a peak between the dip and the drop.

Methods and the systems to detect, sense or monitor vital and health signals using nano-optic filter array based spectrum sensors, and their applications are disclosed. Methods of mapping spectrum sensor outputs to health signals or color information, and methods and devices used to shape the spectral responses of the nano-optic filters are also disclosed. Structures and configurations of highly conductive materials are used to suppress or cutoff the transmission or to enhance the reflection.

BRIEF DESCRIPTION OF THE DRAWINGS

FIG. 9A illustrates a 2-D array of nano-optic filter structure having a rectangular array configuration;

FIG. 9B illustrates a 2-D array of nano-optic filter structure having a hexagonal (or triangular) array configuration;

FIG. 9C shows an individual slit;

FIG. 9D illustrates a square array structure having a horizontal gap that is half the pitch value;

FIG. 9F-9H show rectangular array structures of various vertical and horizontal pitches;

FIG. 10 shows low-magnification and high-magnification SEM images of various filter structures;

FIGS. 26-1 through 26-56 show computer simulations of various filter structures.

DETAILED DESCRIPTION

Unless otherwise specified, the words "a" or "an" as used herein mean "one or more". The term "light" includes visible light as well as UV and IR radiation.

Figure 1:
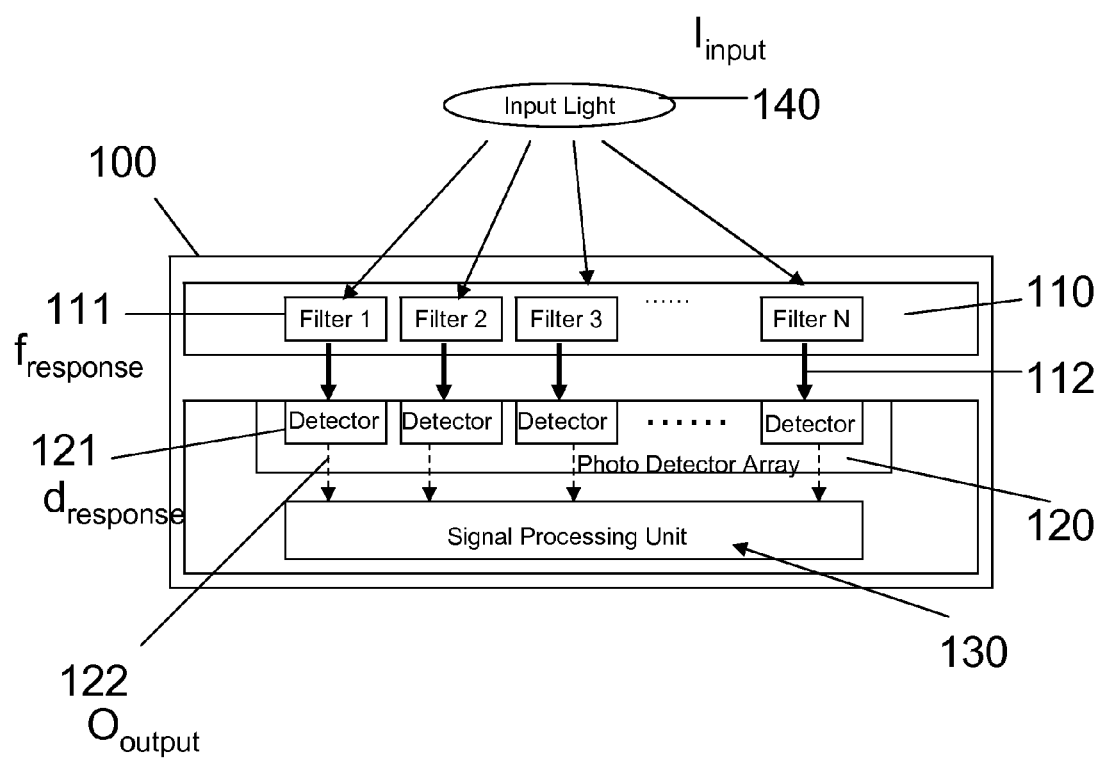
FIG. 1 is a schematic representation of a spectrum sensor using digitized spectral responses of a filter array.

In FIG. 1, a digital filter spectrum sensor 100 is shown containing a set of filters 110, a set or array of detectors 120 (such as a photo diode array or another suitable photodetector array), and a signal processing unit 130. The filters can be made of dielectric or metallic materials, can be waveguide structures, grating structures, Fabry-Perot etalon structures, or plasmonic filter structures.

Figure 2A:
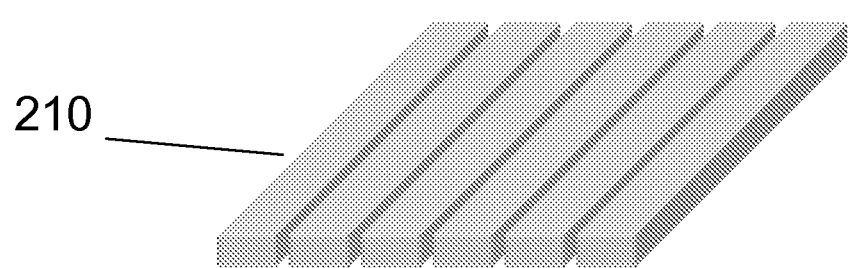
FIGS. 2A, 2B, and 2C show perspective views of different types of plasmonic nano-optic filter devices.
Figure 2B:
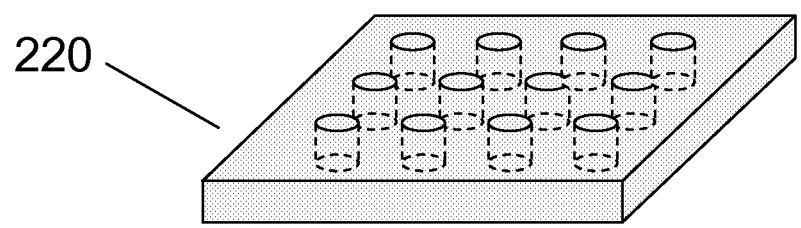
Figure 2C:
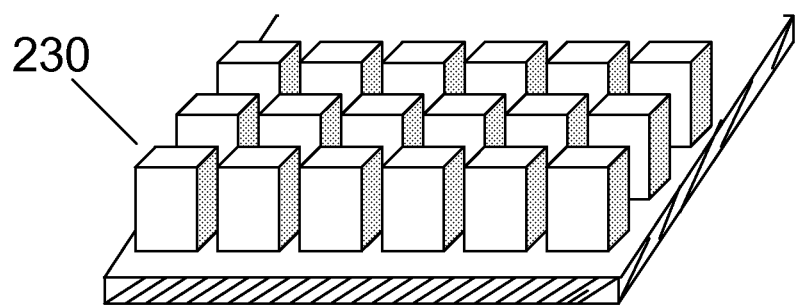

The examples of plasmonic filter structures are shown in FIGS. 2A, 2B, and 2C. In FIG. 2A, the plasmonic filter device 210 shows the metallic nanowire or island structure. In FIG. 2B, the plasmonic filter device 220 shows the metallic film with apertures or holes. Examples of such devices 210 and 220 are described for example in U.S. Patent Application Pub. No. 2006/0273245 A1, the disclosure of which is hereby incorporated by reference in its entirety. In FIG. 2C, the plasmonic filter device 230 shows the metallic embossing structures on a metal film. Examples of such devices 230 are described for example in U.S. provisional application Ser. No. 60/877,660 filed on Dec. 29, 2006, the disclosure of which is hereby incorporated by reference in its entirety. The plurality of metal islands, multiple apertures in metal film or metal embossing array on a metal film are configured such that the incident light is resonant with at least one plasmon mode on the structures in said metal film or metal islands. A predetermined wavelength will perturb the metallic plasmonic structures in surface plasmon energy bands for the wavelength selective transmission of light. The filter device is located either on a dielectric substrate or in between two dielectric layers.

Figure 5A:
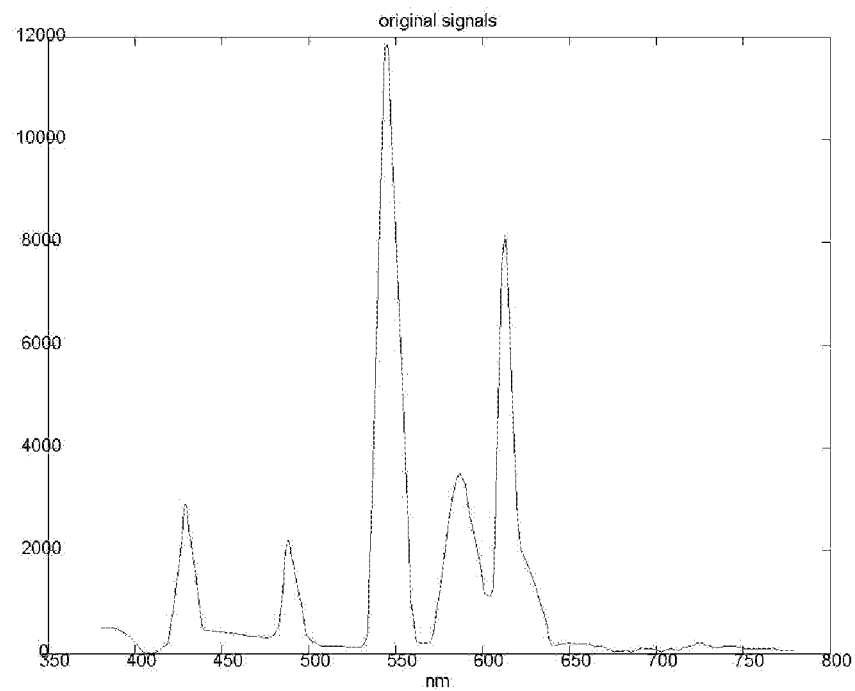
FIG. 5A is an example of spectral profile of an input light.
Figure 5B:
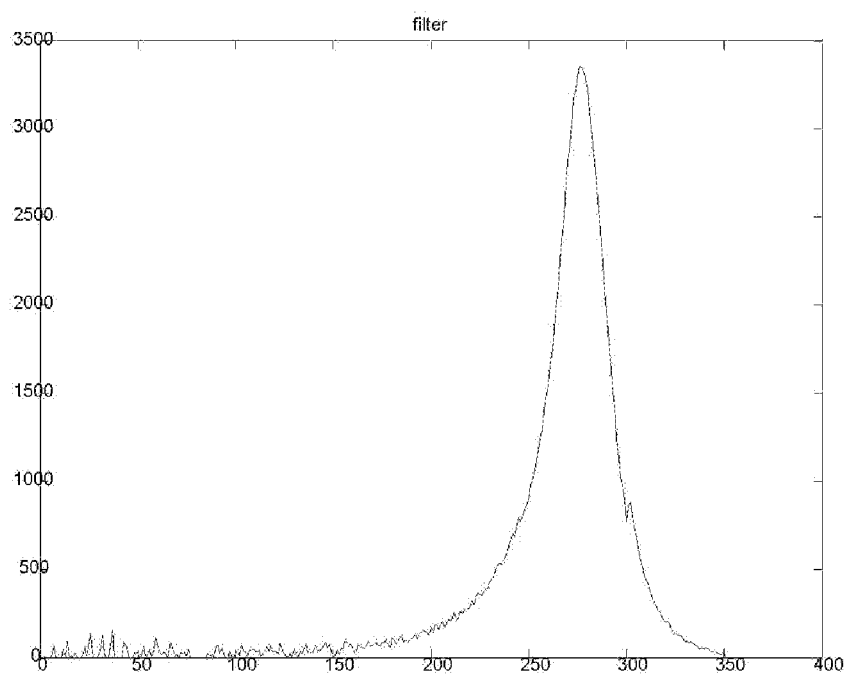
FIG. 5B is an example of a spectral response of a broad bandwidth filter.
Figure 6A:
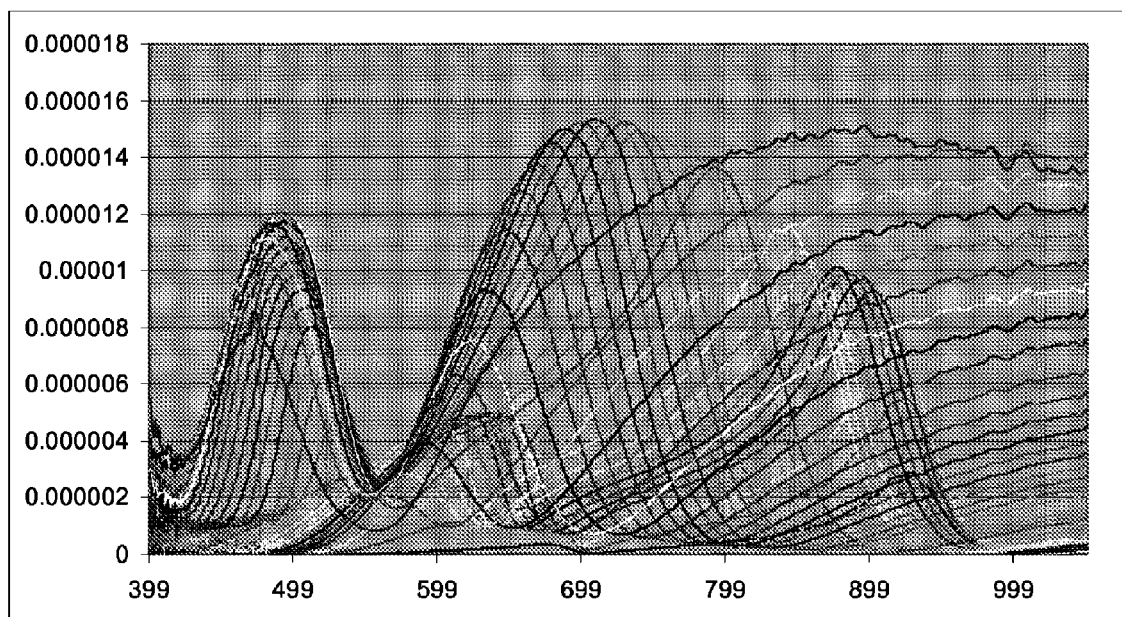
FIG. 6A shows overlaid spectral responses of forty broadband and multi-peak filter sets.
Figure 6B:
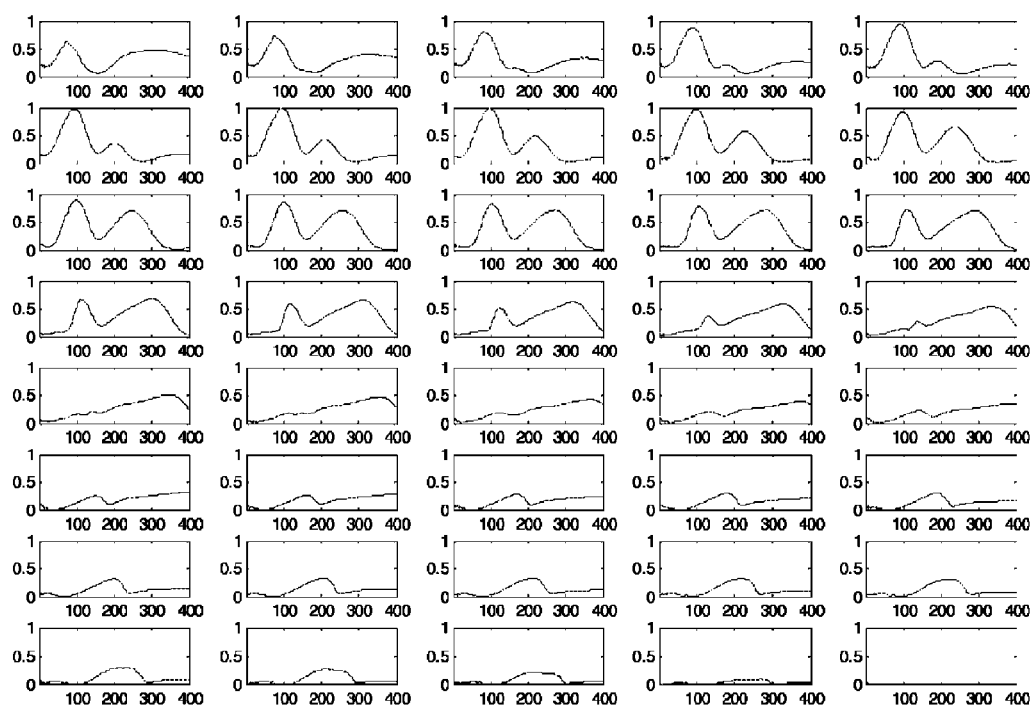
FIG. 6B shows the individual spectral responses of these filters.

The spectral response 111 of each filter may show single peak as shown in FIG. 5B or multi-peaks as shown in FIGS. 6A and 6B. The spectral responses of individual filters can be measured at the time when the filters are fabricated or during the period when the filters are used. The measured spectral response data is digitized through sampling in wavelength domain over the whole interest wavelength range and quantization. The sampling rate can be no less than the desired wavelength resolution. For example, if the desired resolution is 10 nm over the 400 nm range from 380 nm to 780 nm, the sampling rate will be no less than 40 times in such a way the spectral response of a filter is measured at 485 nm, 495 nm, 505 nm, . . . , and 775 nm, or more. Then the measured data is quantized to a digital data at a defined scale. For example, if the defined scale is 8-bit, the measured data is converted into 8-bit digital data. If the defined scale is 16-bit, the measured data is converted into 16-bit digital data. The digitized filter data now will be stored in the processing unit 130, more specifically in the designated memory 331 of the processing unit.

Figure 3:
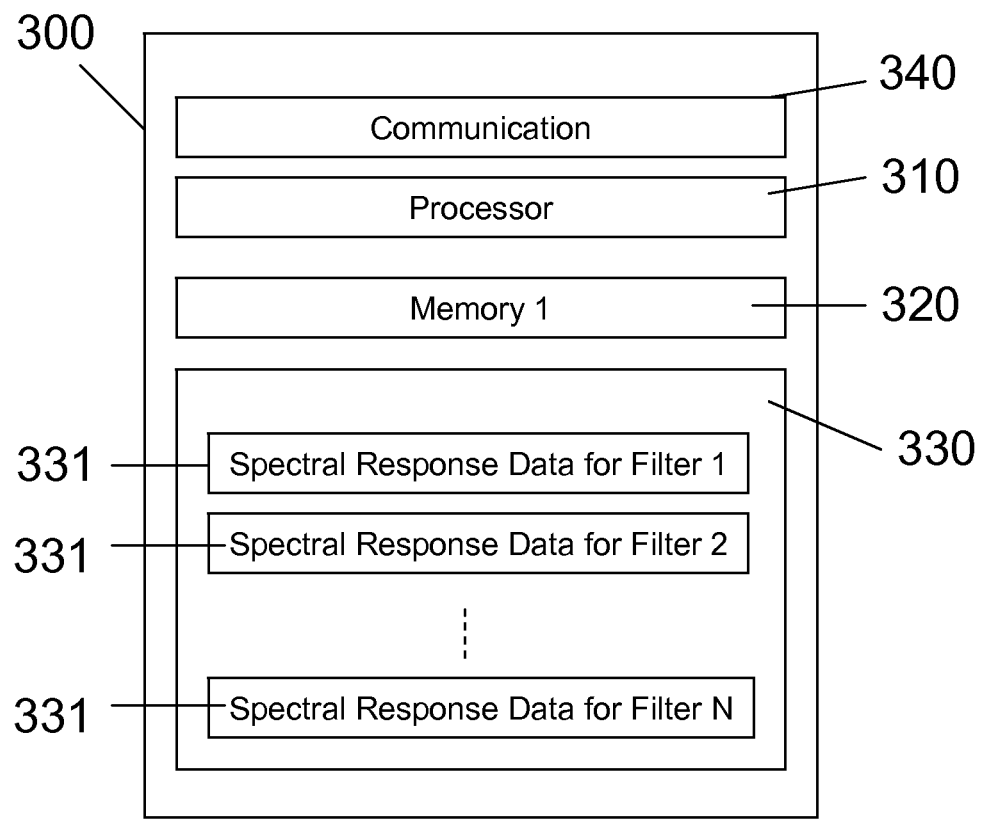
FIG. 3 is a graphical representation of a processing unit within the spectrum sensor.

In FIG. 3, a processing unit 300 of the digital filter spectrum sensor 100 is shown as comprising a communication unit 340, a processor 310 (such as any suitable logic chip or device, such as an ASIC or a computer logic portion), memory 320 (such as any suitable volatile or non-volatile memory devices or computer components) for program run, and designated memory 331 for digitized filter data. The communication unit 340 can comprise a serial or parallel connector or can be a wireless communication unit such as a Bluetooth or Wibree, Zigbee, Wireless USB, or Wi-Fi, or any variations of those. The memory 331 is preferably a non-volatile memory. In the implementation, this processing unit may reside within the same spectrum sensor device 100 or may be a separate chip or computer connected to the spectrum sensor device 100. The processing operations may be conducted by software stored in a computer, or by hardware of the processor 310, depending on the desired configuration or whether a computer or a chip is used as a processor.

In FIG. 1, the input light $I_{input}$ 140 goes through the filter $f_{response}$ 111 and detector response $d_{response}$ 121 to get an output matrix $O_{output}$ 122 which is N×1 array format. The detector response $d_{response}$ 121 can be identical to all the detectors across the whole detector array. When digitized, the filter response $f_{response}$ 111 and detector response $d_{response}$ 121 are multiplied to combine the spectral responses into a single spectral response matrix F such that $F_1=(d_1 \times f_{11}, d_2 \times f_{12} \ldots d_N \times f_{1N})$, $F_2=(d_1 \times f_{21}, d_2 \times f_{22} \ldots d_N \times f_{2N}), \ldots$, and $F_N=(d_1 \times f_{N1}, d_2 \times f_{N2} \ldots d_N \times f_{NN})$. The $O_{output}$ now can be expressed as $F \times I_{input} + n = O_{output}$, where n is noise. When the noise n is negligible, the unknown input $I_{input}$ can be calculated or estimated through the matrix inversion operation such as $I_{input\_estimate} = F^{-1} \times O_{output}$ or $I_{input\_estimate} = F^+ \times O_{output}$ where $F^+$ is psudoinverse of $F$.

Figure 4:
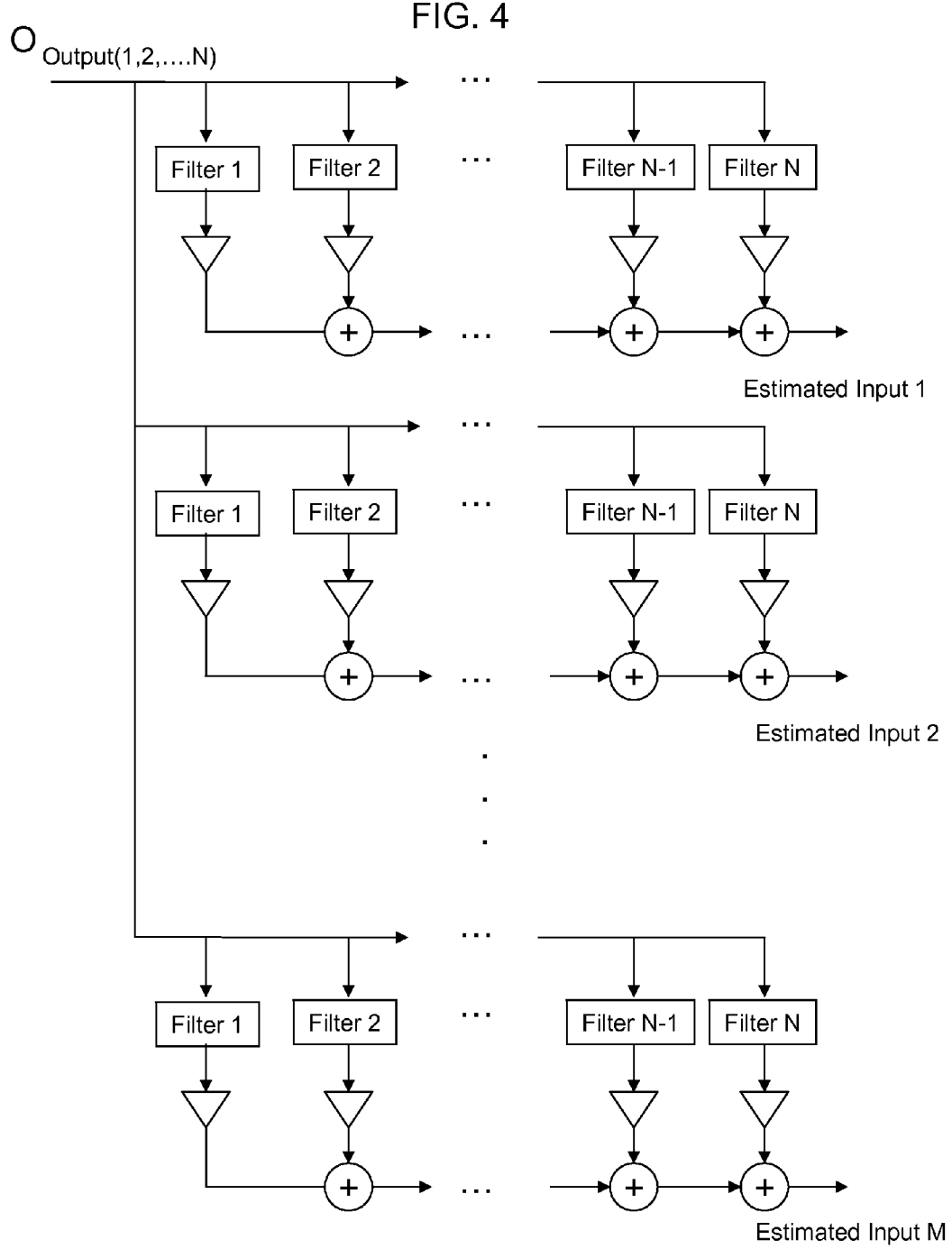
FIG. 4 shows the conceptual diagram for the operation of the Least Square estimate, equalization, matrices inversion, or Moore-Penrose pseudoinverse.

Since the pseudoinverse provides a least squares solution to a system of linear equations, preferably, pseudoinverse operation may be used for most estimates. FIG. 4 shows how the set of digital filter information is used to get an estimate or to calculate the input level at each wavelength point. Preferably, M (number of estimate point for an input)=N (number of filters used) where either matrix inverse or psudoinverse may be used.

In mathematics, the pseudoinverse $A^+$ of a matrix A is the unique matrix satisfying the following criteria:
1. $AA^+A=A$;
2. $A^+AA^+=A^+$ ($A^+$ is a weak inverse for the multiplicative semigroup);
3. $(AA^+)^*=AA^+$ ($AA^+$ is Hermitian); and
4. $(A^+A)^*=A^+A$ ($A^+A$ is also Hermitian).

Here $M^*$ is the conjugate transpose of a matrix M. For matrices whose elements are real numbers instead of complex numbers, $M^*=M^T$.

An alternative way to define the pseudoinverse is via a limiting process:

$$A^+ = \lim_{\delta \to 0}(A^*A + \delta I)^{-1}A^* = \lim_{\delta \to 0}A^*(AA^* + \delta I)^{-1}$$

These limits exist even if $(AA^*)^{-1}$ and $(A^*A)^{-1}$ do not exist.

a. Properties

Pseudoinversion is reversible. It is its own inverse: $(A^+)^+=A$.

The pseudoinverse of a zero matrix is its transpose.

Pseudoinversion commutes with transposition, conjugation, and taking the conjugate transpose:

$(A^T)^+=(A^+)^T$, $\overline{A^+}=\overline{A}^+$, and $(A^*)^+=(A^+)^*$.

The pseudoinverse of a scalar multiple of A is the reciprocal multiple of $A^+$:

$(\alpha A)^+=\alpha^{-1}A^+$ for $\alpha \neq 0$.

If the pseudoinverse of $A^*A$ is already known, it may be used to compute $A^+$:

$A^+=(A^*A)^+A^*$.

Likewise, if $(AA^*)^+$ is already known:

$A^+=A^*(AA^*)^+$.

b. Special Cases

If the columns of A are linearly independent, then $A^*A$ is invertible. In this case, an explicit formula is:

$A^+=(A^*A)^{-1}A^*$.

It follows that $A^+$ is a left inverse of A: $A^+A=I$.

If the rows of A are linearly independent, then $AA^*$ is invertible. In this case, an explicit formula is:

$A^+=A^*(AA^*)^{-1}$.

It follows that $A^+$ is a right inverse of A: $AA^+=I$.

If both columns and rows are linearly independent (that is, for square nonsingular matrices), the pseudoinverse is just the inverse:

$A^+=A^{-1}$.

If A and B are such that the product AB is defined and either A or B is unitary, then $(AB)^+=B^+A^+$. If A and B are such that the product AB is defined, A is of full column rank, and B is of full row rank, then $(AB)^+=B^+A^+$. The second case here does not cover the first; a unitary matrix must be of full rank, but otherwise there is no assumption made on the matrix it multiplies.

It is also possible to define a pseudoinverse for scalars and vectors. This amounts to treating these as matrices. The pseudoinverse of a scalar x is zero if x is zero and the reciprocal of x otherwise:

$$x^+ = \begin{cases} 0, & \text{if } x = 0; \\ x^{-1}, & \text{otherwise.} \end{cases}$$

The pseudoinverse of the null vector is the transposed null vector. The pseudoinverse of other vectors is the conjugate transposed vector divided by its squared magnitude:

$$x^+ = \begin{cases} 0^T, & \text{if } x = 0; \\ \dfrac{x^*}{x^*x}, & \text{otherwise.} \end{cases}$$

For a proof, simply check that these definitions meet the defining criteria for the pseudoinverse.

c. Finding the Pseudoinverse of a Matrix

Let k be the rank of a m×n matrix A. Then A can be decomposed as A=BC, where B is a m×k-matrix and C is a k×n matrix. Then $A^+=C^*(CC^*)^{-1}(B^*B)^{-1}B^*$.

If A has full row rank, so that k=m, then B can be chosen to be the identity matrix and the formula reduces to $A^+=A^*(AA^*)^{-1}$. Similarly, if A has full column rank (that is, k=n), then $A^+=(A^*A)^{-1}A^*$.

A computationally simpler way to get the pseudoinverse is using the singular value decomposition.

If $A=U\Sigma V^*$ is the singular value decomposition of A, then $A^+=V\Sigma^+U^*$. For a diagonal matrix such as $\Sigma$, we get the pseudoinverse by taking the reciprocal of each non-zero element on the diagonal.

Optimized approaches exist for calculating the pseudoinverse of block structured matrices.

If a pseudoinverse is already known for a given matrix, and the pseudoinverse is desired for a related matrix, the pseudoinverse for the related matrix can be computed using specialized algorithms that may need less work. In particular, if the related matrix differs from the original one by only a changed, added or deleted row or column, incremental algorithms exist that exploit the relationship.

d. Applications

The pseudoinverse provides a least squares solution to a system of linear equations.

Given an overdetermined system with independent columns $Ax=b$, we look for a vector x that minimizes $\|Ax-b\|^2$, where $\|\cdot\|$ denotes the Euclidean norm.

The general solution to an inhomogeneous system $Ax=b$ is the sum of a particular solution of the inhomogeneous system and the general solution of the corresponding homogeneous system $Ax=0$.

Lemma: If $(AA^*)^{-1}$ exists, then the solution x can always be written as the sum of the pseudoinverse solution of the inhomogeneous system and a solution of the homogeneous system:

$$x = A^*(AA^*)^{-1}b + (1 - A^*(AA^*)^{-1}A)y.$$

Proof:

$$Ax = AA^*(AA^*)^{-1}b + Ay - AA^{**}(AA^*)^{-1}Ay$$
$$= b + Ay - Ay$$
$$= b.$$

Here, the vector y is arbitrary (apart from the dimensionality). In both summands, the pseudoinverse $A^*(AA)^{-1}$ appears. If we write it as $A^+$, the equation looks like this:

$$x = A^+b + (1 - A^+A)y.$$

The first summand is the pseudoinverse solution. In the sense of the least squares error, it is the best linear approximation to the actual solution. This means that the correction summand has minimal euclidean norm. The second summand represents a solution of the homogeneous system Ax=0, because $(1-A^+A)$ is the projection on the kernel (null space) of A, while $(A^+A)=A^*(AA^*)^{-1}A$ is the projection onto the image (range) of A (the space spanned by the column vectors of A). The Moore Penrose pseudoinverse is described in more detail in Table I which follows the Figures.

As is usually the case in most signal processing system, however, there will be noises in this digital filter spectrum sensor system. The noise negatively impacts on estimating the input value, reducing the accuracy of the system. To remove or reduce the noise effects, simple spatial averaging or time averaging can be used. Spatial averaging uses the multiple identical sets of filters to receive the input at different physical locations on detector array. Time averaging uses multiple data reading through the same detector. The multiple outputs of the detectors can be averaged, or multiple of the input estimates through the matrices inversion can be averaged.

Further, when the noise n is not negligible as in most practical cases, the unknown input can be estimated through various Least Square estimate methods with various types of constraints, as summarized in the following references: Roman Z Morawski, REVIEW ARTICLE, Spectrophotometric applications of digital signal processing, Meas. Sci. Technol. 17 (2006) R117-R144, and Cheng-Chun Chang and Heung-No Lee, On the estimation of target spectrum for filter array based spectrometers, 21 Jan. 2008/Vol. 16, No. 2/OPTICS EXPRESS 1056, which are incorporated by reference in their entirety.

In the Chang et al. reference, the Least Square estimate operation is further explained in detail as following. The transformation between the target spectrum and the CCD-sensor outputs is associated by the matrix equation $$r = Hs + n, \qquad (1)$$

where the dimensionalities of r, H, s, and n are N×1, N×M, M×1, and N×1, respectively.

Suppose r is an observed signal vector. Working on the observation vector, an estimator provides an estimation ŝ of the input spectrum by considering all possible source signal-vectors s. One criterion which can be used as the starting point is the maximum a posteriori (MAP) rule. The MAP estimator is obtained by maximizing the posterior probability, i.e., $$\hat{s}_{MAP} = \arg\max_s P(s|r). \qquad (2)$$

From the Bayes' rule, the posterior probability can be written as P(s|r)=P(r|s)P(s)/P(r). Therefore, there is no information on the source signal such that P(s) is uniformly-distributed, the MAP estimator can be simplified to the maximum likelihood (ML) estimator. The ML estimator maximizes the likelihood function, i.e., $$\hat{s}_{ML} = \arg\max_s P(r|s). \qquad (3)$$

For the filter-array spectrometer, the observed signal vector, r, and the source signal vector, s, can be associated by Eq. (1) as discussed. Now assume the noise vector n is multivariate Gaussian with zero mean and covariance matrix $R_n$, i.e., E[n]=0, and $E[nn^T]=R_n$, where the superscript T denotes the transpose operation The ML estimator then is obtained by maximizing the likelihood function $$P(r|s) = \frac{1}{(2\pi)^{N/2}|R_n|^{1/2}} \exp\left[-\frac{1}{2}(r-Hs)^T R_n^{-1}(r-Hs)\right]. \qquad (4)$$

To solve for the estimator, it is equivalent to find the vector s which minimizes $-2r^T R_n^{-1}Hs + s^T H^T R_n^{-1}Hs$. The solution can be found by solving the partial differential equation $\partial(-2r^T R_n^{-1}Hs + s^T H^T R_n^{-1}Hs)/\partial s = 0$. Providing that the matrix $H^T R_n^{-1} H$ is nonsingular (i.e., inverse exists), the solution of this is $$\hat{s}_{ML} = (H^T R_n^{-1} H)^{-1} H^T R_n^{-1} r. \qquad (5)$$

Furthermore, if there is no knowledge about the correlation of the Gaussian noise vector (or if the elements are mutually independent), it is reasonable to substitute the covariant matrix $R_n$ by an identity matrix I. Thus the ML estimator, Eq. (5), is reduced to the least-squares (LS) estimator, i.e., $$\hat{s}_{LS} = (H^T H)^{-1} H^T r. \qquad (6)$$

It requires that the inverse of $H^T H$ matrix exists. Recall that the dimensionality of H is N×M. For solution to exist, M needs to be less than or equal to N such that the M×M $H^T H$ matrix is possibly full rank. That is, the number of filters used in the filter-array spectrometer needs to be greater than or equal to the number of resolved points in the wavelength-domain. For the most efficient and practical consideration, take M=N, i.e., H is a square matrix. Then the LS estimator can be reduced to $$\hat{s}_{inv} = (H^T H)^{-1} H^T r = H^{-1} r. \qquad (7)$$

It is worth to mention that, for zero-mean noise, the $\hat{s}_{ML}$, $\hat{s}_{LS}$, and $\hat{s}_{inv}$ are unbiased, e.g., $E[\hat{s}_{ML}] = (H^T R_n^{-1} H)^{-1} H^T R_n^{-1} Hs = s$. Therefore, for a fixed unknown source signal vector s, one may have the received signal vector r measured multiple times over either the temporal or spatial domain. This unbiased property ensures the enhancement of estimation accuracy after averaging operation. The estimation-error covariance-matrix of the ML estimator, Eq. (5), can be calculated and expressed as $E[(\hat{s}-s)(\hat{s}-s)^T] = (H^T R_n^{-1} H)^{-1}$. We note that it is a function of the filter matrix H. Thus, it can show how good an estimator can be for a particular filter array. Although the covariance matrix of system noise $R_n$ is fixed, the variance of the estimation error can be amplified by the detector sensitivity matrix H. Of interest is the case that H is a square matrix. Conventionally, the singular value decomposition (SVD) is considered as a powerful technique to deal with the noise amplification issue. This method computes the inverse of the H matrix based on the singular value decomposition where an Eigen value less than a certain threshold can be discarded. By exploiting the non-negative nature of the spectral content, the non-negative constrained least-squares (NNLS) algorithm works particularly well to estimate the target spectral. NNLS can be seen as a member of the family of the least squares estimator. NNLS returns the vector $\hat{s}$ that minimizes the norm subject to $\hat{s}>0$. The original design of the algorithm was by C. L. Lawson, and R. J. Hanson. Although the NNLS algorithm solves the solution iteratively, the iteration always converges.

Figure 5C:
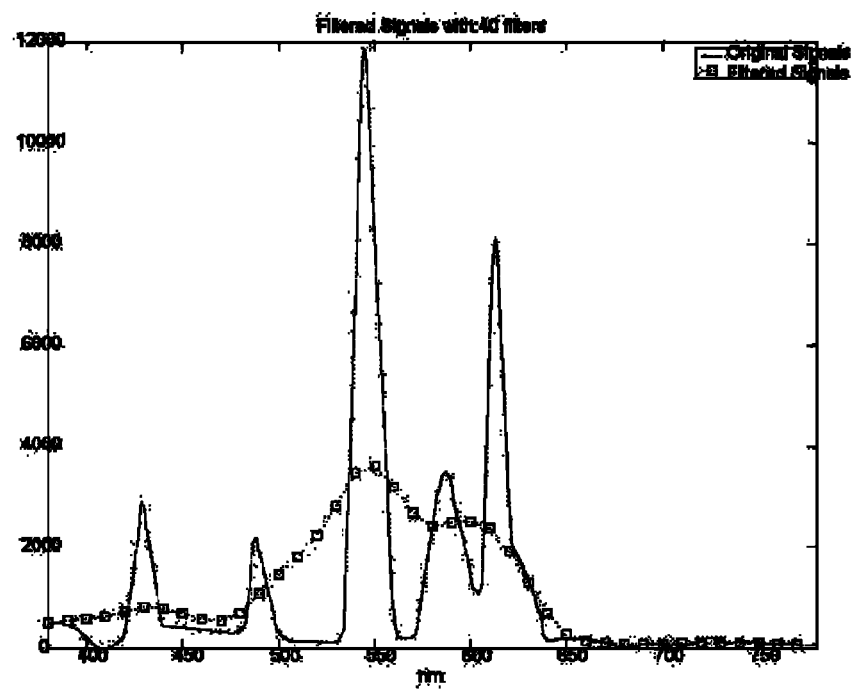
FIG. 5C shows an output result without the resolution enhancement operation.
Figure 5D:
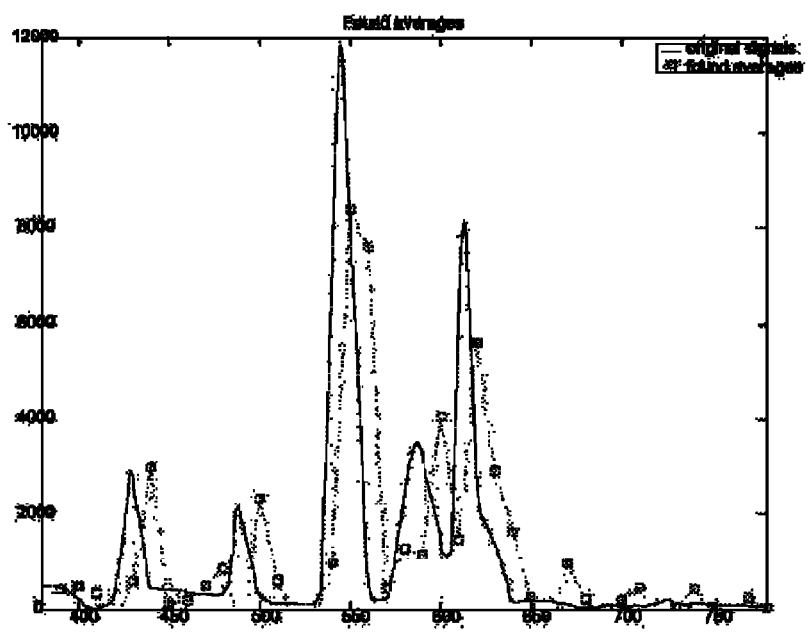
FIG. 5D shows the output with the resolution enhancement operation.
Figure 7:
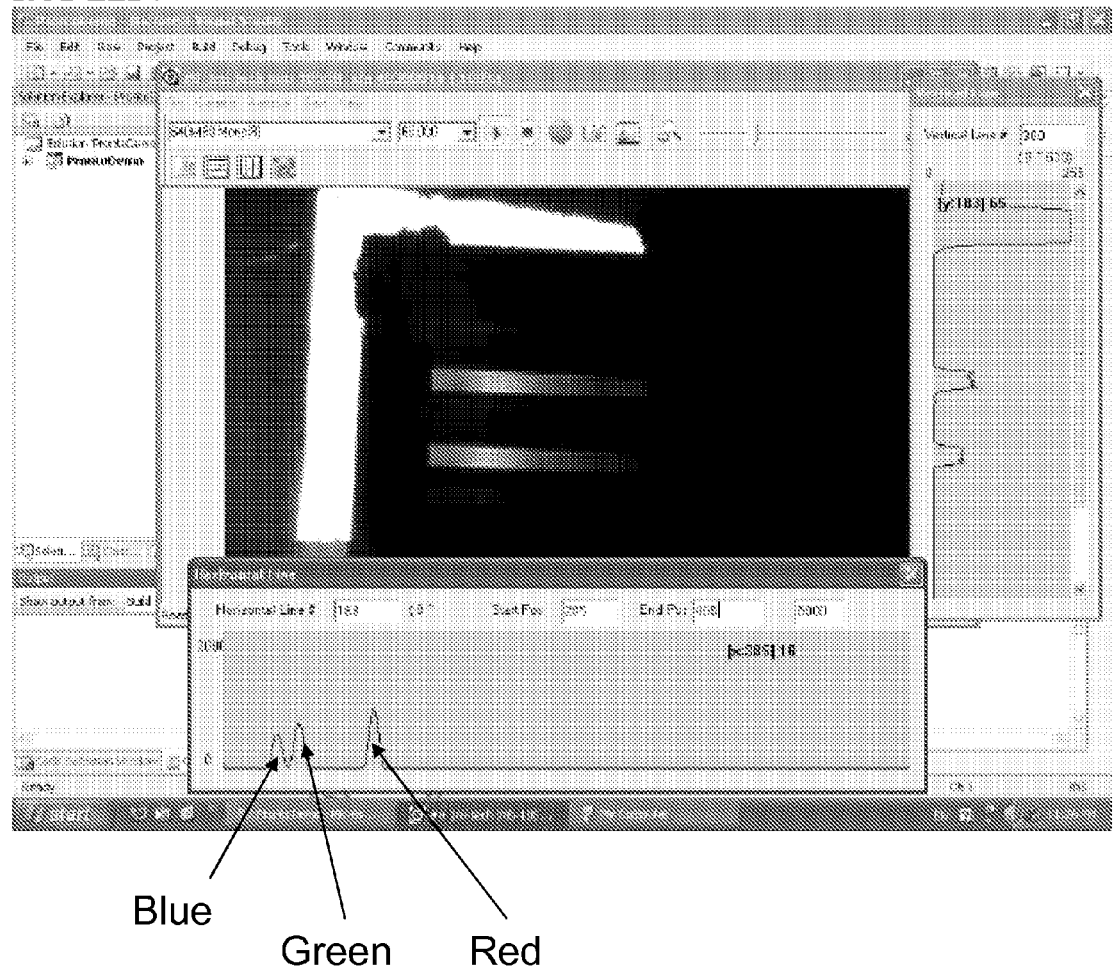
FIG. 7 shows the output from three different LEDs (Red, Green and Blue) using the spectrum sensor through resolution enhancement operation using digitized spectral response data of filters.

The input example shown in FIG. 5A is the spectral profile of a typical fluorescence lamp. When this input is read or measured by the set 40 of the broad bandwidth filters whose FWHM is about 60 nm as shown in FIG. 5B, the output spectral profile, shown as square dot line in FIG. 5C, through these 40 filters and detectors is not very close to the original input spectral profile. However, when the matrices inversion operation is executed, the input estimates, shown as square dot line in FIG. 5D now become much closer to the original input spectral profile. FIG. 6A and FIG. 6B show another example of filter set with the broad bandwidth and multi-peaks used to detect the spectral profile of LEDs (Red, Green and Blue). As shown in FIG. 7, the digital filter spectrum sensor with these types of broad bandwidths and multi-peaks can rebuild the spectral profile of three LEDs, quite closely to the original LEDs' spectral profile. Noticeably, the bandwidth of the filter used is close to 100 nm, but the digital filter spectrum sensor system reconstructs the input signals at higher resolution such as 10 nm. Also the known spectral information of the LEDs, input lights, can be utilized to estimate further closer to the original signals. This color measurement capability will find lots of useful application areas in color measurement or monitoring for flat panel display, printed materials, or even in bio applications. The measured spectral information can be mapped into color domain data in different format such as CIE systems, such as CIELUV or CIELAB or CIE 1931 or CIE 1976.

Figure 8A:
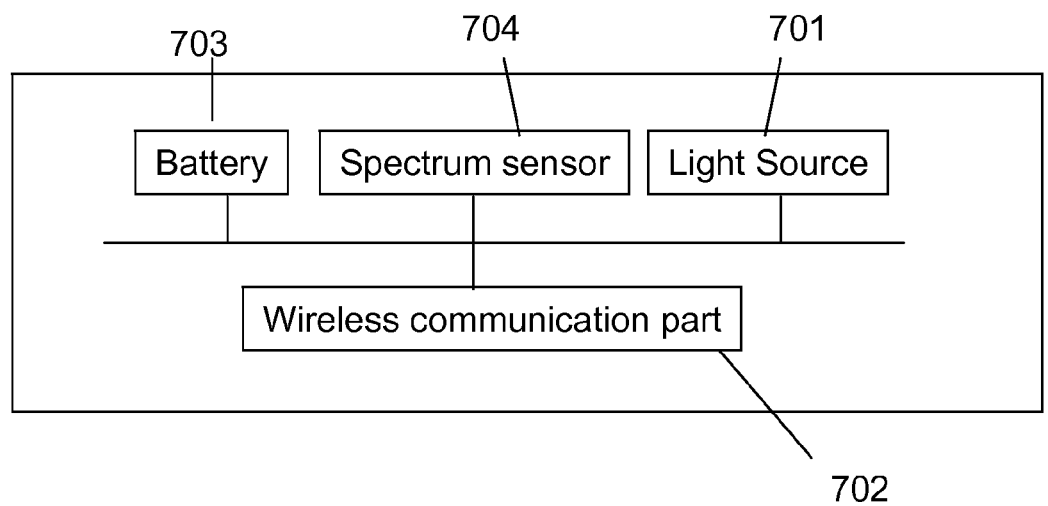
FIG. 8A is a the schematic representation of a wireless spectrum sensor.
Figure 8B:
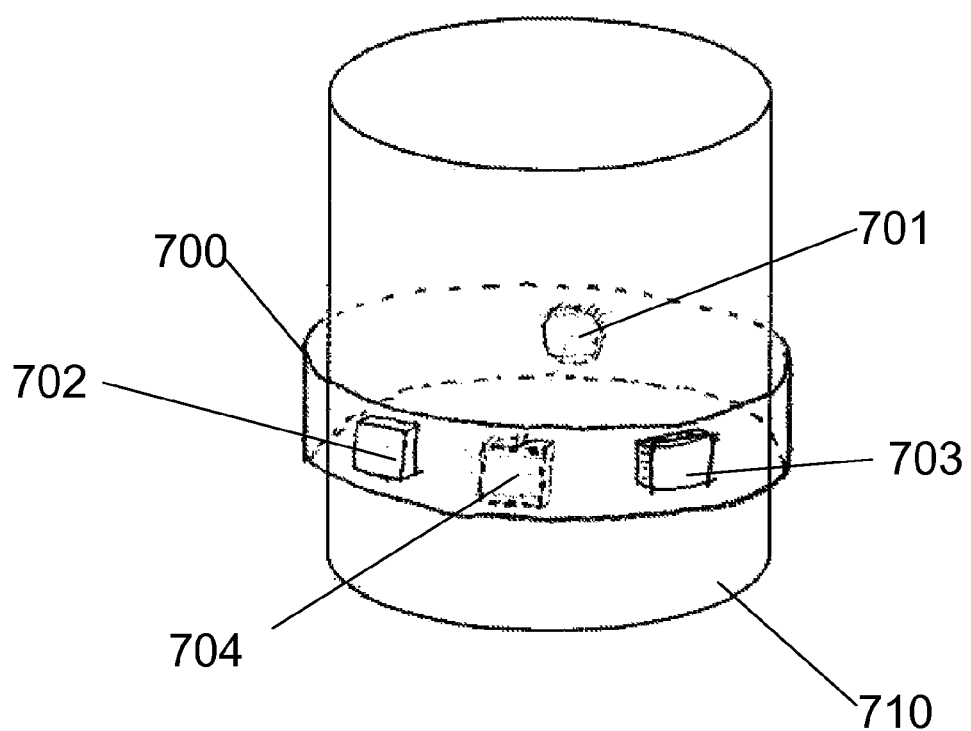
FIG. 8B is a prospective representation of a wireless spectrum sensor around a target.

Because of its compact size and reasonable resolution, the digital spectrum sensor can be used in many applications where the small size is desired. Such applications may include mobile or wearable devices to monitor personal health, high resolution color monitoring for the color input, display and output devices, and environmental monitoring sensors such as water or air quality sensors. For some of those applications, wireless solution may be more desirable. As shown in FIGS. 8A and 8B, the wireless spectrum sensor has one or more embedded wireless units 702 mounted on a holder (such as a substrate or a band) along with spectrum sensor 704, one or more light sources 701, and a power unit 703, such as a battery unit or power generator. The holder may have embedded circuits connecting these embedded units. This wireless digital spectrum sensor may be located adjacent to or wrap around the target object 710, such as a human or animal body part, an inanimate object, the container of the target object to be measured, or the passage or pipeline where the target objects (such as any suitable fluid) to be measured pass through. If the power unit 703 is a power generator, then this power generator may utilize wireless RF power to generate the electrical power and/or it may utilize the flow of said object, such as water or other fluid, to generate power.

FIG. 9A illustrates a 2-D array of nano-optic filter structure 910 comprising an aluminum layer on a quartz substrate. The Al layer has a rectangular array of apertures. The filter structure 910 can be fabricated, for example, by electron beam photolithography and Al etching process on the quartz substrate. The filter structure 910 can have dimensions of, for example, 50×50 µm. FIG. 9B illustrates a 2-D array of nano-optic filter structure 920 having a hexagonal (or triangular) aperture array configuration. Other array configurations can also be employed.

In the examples shown in FIGS. 9A and 9B, the array elements are the slits or apertures in a conductive layer. In some other embodiments, the array elements can include reflective particles or protrusions. The shapes, sizes, gaps between the array elements, and the patterns can be engineered to affect the transmittance (if the filter is configured as a transmissive filter) or reflectance (if the filter is configured as a reflector or a reflective filter).

FIG. 9C shows an individual slit 930, which can be characterized by a vertical slit width (V-Gap, or y) and a horizontal slit length (H-Gap, or x).

FIG. 9D illustrates a square array structure 940a having an H-Gap=0.5×Pitch. FIG. 9E illustrates a triangular array structure 940b having an H-Gap=0.5×Pitch. The height of the triangle is $\sqrt{3}/2\times$Pitch.

FIG. 9F-9H show rectangular array structures 950a, 950b, 950c of various vertical and horizontal pitches.

FIG. 10 shows low-magnification and high-magnification SEM images of various filter structures of the embodiments disclosed herein.

Figure 11:
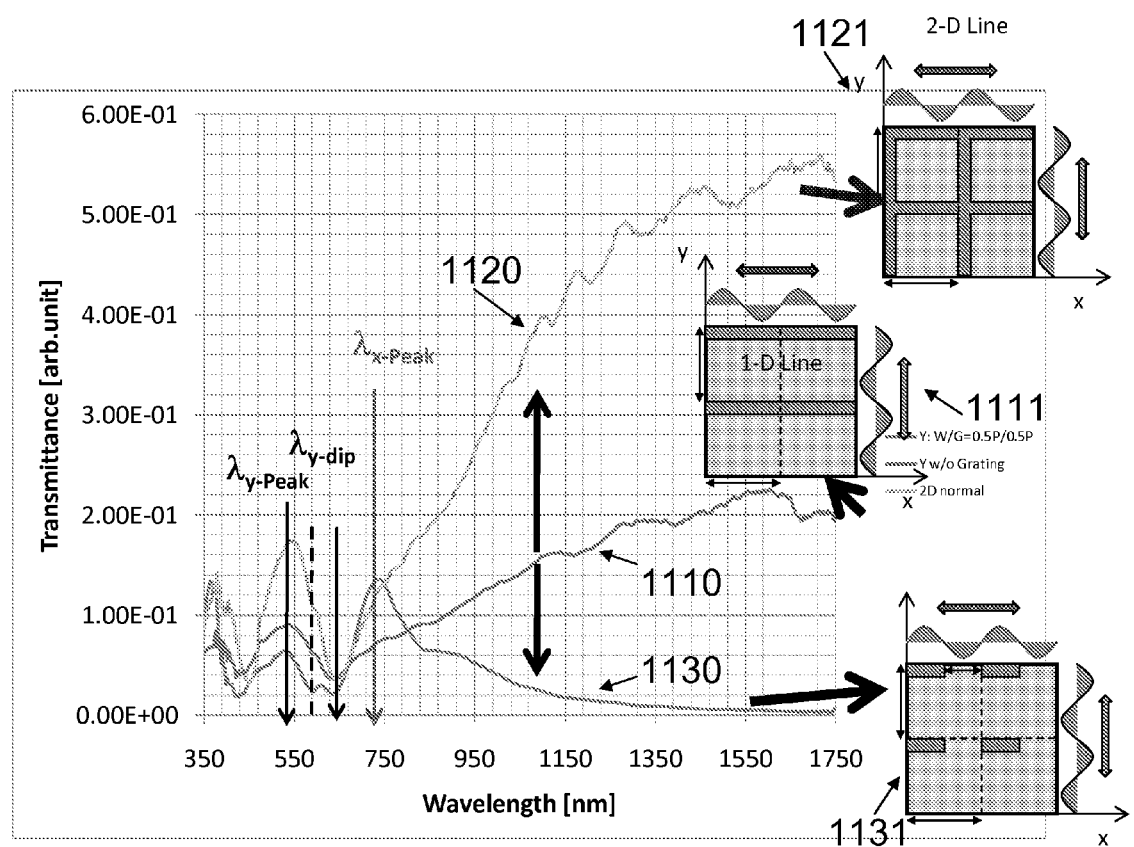
FIG. 11 shows transmittance spectra of a 1-D line structure filter, a 2-D line structure filter, and 2-D array structure filter.

FIG. 11 shows transmittance spectra 1110, 1120, and 1130, respectively of a 1-D line structure filter 1111, a 2-D line structure filter 1121, and 2-D array structure filter 1131. From these spectral curves 1110, 1120, and 1130 it can be seen that the $\lambda_{y-Peak}$ (~530 nm) and $\lambda_{y-Dip}$ (~630 nm) exist at about the same wavelength locations regardless of whether the filter structure is 1-D or 2-D. The peak intensities of the $\lambda_{y-Peak}$ of the 1-D line structure (~0.9) and the 2-D line structure (~1.75) are different. The longer wavelength noise of 2-D line structure (~5.6) is significantly higher than that of the 1-D line structure (~2.2).

The 2-D array filter structure 1131 as shown has a transmittance spectrum with a drop at the long wavelength end. The drop or cut off can be characterized by a "cut-off" wavelength, for example, defined by the wavelength at which the transmittance drops to about 50% of its peak value. The drop in the spectrum 1130 in conjunction with the dip at $\lambda_{y-Dip}$ forms another peak at $\lambda_{x-Dip}$ (~750 nm in this case). This advantageously narrows the shape of the spectrum 1130 at the wavelength region of interest thereby improving the resolution of the transmittance spectrum.

The shape of the transmittance spectrum can be engineered, for example, by varying the length (x) and width (y) of the slits, and the horizontal pitch (X) and vertical pitch (Y). X, Y, x, and y are generally comparable to the wavelength range of interest (e.g., IR radiation, UV radiation or visible light (400-700 nm)). Preferably x and y are smaller than the wavelength of interest, and thus the slits are often referred to as having "sub-wavelength" dimensions. In a preferred embodiment, y<x, and in the filter structure 1131 as shown x/X~0.5. For example, X=100 to 1000 nm, x=50 to 500 nm, Y=200 to 1000 nm and y=20 to 200 nm.

In one embodiment, the slits are formed in a highly conductive layer. The highly conductive layer can comprise, for example, a highly conductive metal or an alloy of metals (i.e., metal alloy), a highly doped semiconductor, a layer comprising carbon nanotubes or graphene, or coated with highly conductive materials. In some embodiments, the highly conductive layer can be a combination of multiple layers.

The highly conductive layer can be disposed between at least two dielectric layers (e.g., quartz, silicon dioxide, silicon nitride, alumina, etc.), as shown for example in FIG. 26-1. The highly conductive layer can have one or more periodic pattern of sub-wavelength apertures. When two or more periodic patterns are included, these periodic patterns can interlace with each other. Alternatively, the array elements can be made of sub-wavelength sized conductive particles or protrusions.

The conductive layer can be made from a same material across the device, although different structures can be disposed over the conductive layer. Alternatively, at least two different highly conductive materials can be used across the device. Similarly, the same, or at least two different dielectric materials, can be used for the top or bottom dielectric layer.

The shapes and sizes of the apertures or gaps are configured such that the transmittance or reflectance spectrum has a drop at the long wavelength end. The drop is often referred to as a "cut-off" that is characterized by a cut-off wavelength. The periods of the array elements can be configured such that the transmittance spectrum is minimized or suppressed (having dips in the spectral curves) at specified wavelengths. These wavelengths can be those resonant with at least one Plasmon mode of the periodic patterns.

As a result of engineering the array structures described above, at least one peak in the transmittance or reflectance can be located between the dip and the cut off wavelength, as shown in the spectrum 1130 in FIG. 11.

In some embodiments, the thickness of the highly conductive layer is thicker than a skin depth, i.e., the light penetration depth, of the highly conductive material.

In some embodiments, the apertures or gaps can have sharpened edges to enhance the transmission or reflection of light at the peak wavelength. The enhancement of the light transmission is realized through, for example, highly condensed charges or fields of the sharpened edges.

A coating comprising a magnetic material can be included to modify the electromagnetic field adjacent the conductive layer to thereby affect a Plasmon mode.

As described in detail below, the narrow widths of the apertures or gaps can also enhance the sharpness of dips and peaks, thereby reducing the FWHM and improving the resolution of the filter or reflector.

In some embodiments, the conductive layer can have at least two alternating periods of the periodic pattern, and/or at least two alternating shapes or sizes of the array elements.

In a preferred embodiment, the dielectric layers on both sides of the conductive layer are composed of the same material. In addition, dielectric material filling the apertures or gaps can also be the same material as the dielectric layers sandwiching the conductive layer. By reducing the types of interfaces, the number of the Plasmon modes can be reduced. Thus, the number of dips and peaks in the transmittance or reflectance spectra can be reduced, and the transmittance or reflectance can be increased.

The shapes and sizes of the apertures or gaps on the top surface and the bottom surface of the conductive layer can be the same, or can be different.

In some embodiments, a plurality of optical filters disclosed above can be stacked together, wherein a separation between the two conductive layers is in the sub-wavelength range, or can be larger than a predetermined wavelength.

In one embodiment, a method is provided to shape a spectrum. A highly conductive layer can be provided between at least two dielectric layers. The highly conductive layer can have at least one periodic pattern of sub-wavelength apertures, or sub-wavelength sized conductive particles. The shapes and sizes of the apertures, gaps, or the particles are configured such that the transmission of incident light is suppressed at the long wavelength portion of the incident light. Periods of the apertures or particles are configured such that the transmission of the incident light is minimized or suppressed (having dips in the spectrum) for the wavelengths resonant with at least one Plasmon mode of the periodic patterns. As a result, at least one peak wavelength of the transmission is located between the dip and a cut off wavelength that characterizes the drop at the long wavelength portion.

An array of optical filters can be provided, for example, including at least two optical filters, or at least four optical filters.

A digital spectrum sensor can be provided. The sensor can include a photodetector array, and an array of optical filters. A processing unit can be included for estimating input spectral resolution enhancement. Each filter of the filter array can be optically coupled to a photodetector or a group of photodetectors of the photodetector array. A vector value of the outputs from the photodetectors associated with the respective filters is used to analyze properties of a target object or to monitor changes in the target object. Methods such as linear or multi-linear or nonlinear estimation, or trained mapping, or pattern recognition can be employed in the analysis.

The spectral response data of the optical filters or combined spectral responses of each filter and its associated photodetector can be sampled, quantized and digitized and used to analyze properties of the target object, or to estimate of the spectral profile of the incident light.

The vector value can be an array of the outputs from the photodetectors and their respectively associated filters. The vector value can be a matrix of cross relationships among the outputs, a matrix of ratios among the photodetectors and filters. The vector value can be a matrix of first or second derivatives of the outputs.

The linear or nonlinear estimation methods can use at least one of the following operations: matrices inversion, equalization, Moore-Penrose pseudoinverse, least square, linear or nonlinear regression, neural network, or multilayer neural network.

The photodetector array can use at least two different sizes of pixels or at least two different shutter times to enhance a dynamic range or to normalize the outputs of the photodetector array. Pixel binning method may be used to normalize the outputs of the photodetector array.

The photodetector array can be only partially covered by the optical filter array to obtain image data in addition to the spectral data, e.g., some of the photodetectors can receive unfiltered light. Thus, the device can be configured as a spectro-photometric sensor conducting spectroscopy and imaging at the same time.

Spatial, temporal, or moving-time averaging processes can be used to improve the Signal-to-Noise ratio. The spatial averaging includes repeating identical filters over the multiple photodetectors and averaging the outputs. The time averaging process includes reading the output of a photodetector repeatedly over the multiple frames and averaging the outputs.

The digitized spectral response data can be adaptively or selectively used for different input lights. The data can be measured and stored in memory as fixed data. The data can also be adaptively modified or updated through calibration.

Input constraints can be used to process the vector value to analyze properties of the target object, monitor changes of the target object, or estimate a spectral profile of input light. Linear or nonlinear estimation, trained mapping, and pattern recognition are some of the methods that can be employed in the analysis. The known input constraint comprises positivity or negativity of the input signals, known spectral information of light sources used, boundary conditions of input signals, or temporal, spatial, or frequency modulated information.

A database of pre-tested or pre-measured relationships between the vector values and the properties of the target object can be stored and used to map or convert the spectral response data into the space domain property of the target object.

A digital spectrum sensor can be provided including a photodetector array and an array of optical filters. A processing unit can be used for estimation of inputs or input spectral resolution enhancement. The optical filters can include Fabry-Perot filters, linear variable filters, thin film filters, photonic crystal filters, or nanostructured thin film filters. Each filter of the filter array can be optically coupled to a photodetector or a group of photodetectors of said photodetector array.

A digital color sensor can be provided and can include the digital spectrum sensor. The vector value of the outputs can be converted or mapped into human's three-color sense values or tristimulus values. The human's three-color values are represented in the form of International Commission on Illumination (CIE) XYZ values, or International Commission on Illumination (CIE) xy chromaticity values, or xyY, or CIE RGB values.

The stored digitized spectral response data can be used to provide the estimated spectral profile of the input light and the color values.

The systems and methods can be used for, e.g., color sensing for TV, color sensing for ambient light, color sensing for printer, or color sensing for skin, food, process monitoring.

An indirect biochemical material detection apparatus can be provided comprising a color sensor, at least one light source, a processing unit with memory, wireless or wired communication means, at least one color changing material, and a light path. The color changing agent changes color when exposed to a predetermined target biochemical material. The degree of the color change can be proportional to the amount of the biochemical material.

A method can be provided to indirectly detect biochemical material using the apparatus. The method includes exposing the color changing agent to a target biochemical object, or to the environment where the target biochemical object exists, shining light onto the color changing agent, sensing the color changes by reading the color sensor outputs, determining the amount of contacted target biochemical materials, and transmitting the information.

Sensing the color changes can be achieved by filtering a reflected, scattered, or transmitted light from the color changing agent using the filters or reflectors disclosed herein. The filter suppresses a spectrum of the light from the color changing agent at a short wavelength region using a Plasmon resonant mode of a periodic pattern in a conductive layer of the color sensor, and suppresses the spectrum at a long wavelength region by selecting shapes and sizes of elements in the pattern to thereby form a peak in the spectrum.

A noninvasive health monitoring device can be provided comprising at least one digital spectrum sensor, at least one light source, a processing unit, a wireless or wired communication unit, optical means for the light path, mechanical means for attaching device to part of a body. The light sources emit light onto the body, and the sensor detects the reflected, scattered, or transmitted light from the body. Vector values of outputs of the sensors are converted, mapped, or interpreted as the person's vital or health information. The vector values can also be transmitted to an information collecting unit. The device can be wearable on the body using, for example, a band, a clip, or a hook.

The part of body can be preferably an earlobe, a finger tip, a wrist, or an upper arm. A fluorescence material can be embedded in said part of body for enhancing the target object detection.

The light from the light source can be modulated by frequency modulation, amplitude modulation, or code modulation. The light source outputs can be wavelength multiplexed from at least two light emitters.

The mapping or conversion of vector value to vital or health information can be self-trained or self-calibrated for an initial use, or after power off-on of said device. A reference light source and a reference light paths can used for self calibration of the device.

A multispectral imager or a hyperspectral imager can be provided including a photodetector array and an array of optical filters. Each of the optical filters can be associated with a pixel of the photodetector array. A mosaic pattern of a group of the optical filters can be repeated spatially over the entire area of the photodetector array. The number of different filters within each group can be, for example, at least four, or at least twelve. The different spectral outputs of pixels within the group can used to define, process, or approximate the spectrum of the group and neighboring groups.

A tunable optical filter or reflector can be provided utilizing the structures disclosed herein. A voltage or current source can be used to apply a voltage or current to the conductive layer and/or dielectric layers. An intensity or wavelength of light transmitted through or reflected from the tunable device is modulated by the voltage or current.

The tunable device can be used in, for example, a transmissive, a reflective, a transreflective flat panel display, which includes an array of the tunable optical filters. The tunable device can also be used in a hyperspectral imager, a photodetector array, an optical modulator, or a Fabry-Perot filter comprising two stacked filters in which the distance between the two filters is smaller than a predetermined wavelength of incident light. The two stacked filters can have different shape and configurations.

In the tunable Fabry-Perot filter, the dielectric materials between the two filters can have sub-wavelength structures to change the effective refractive index.

Figure 12:
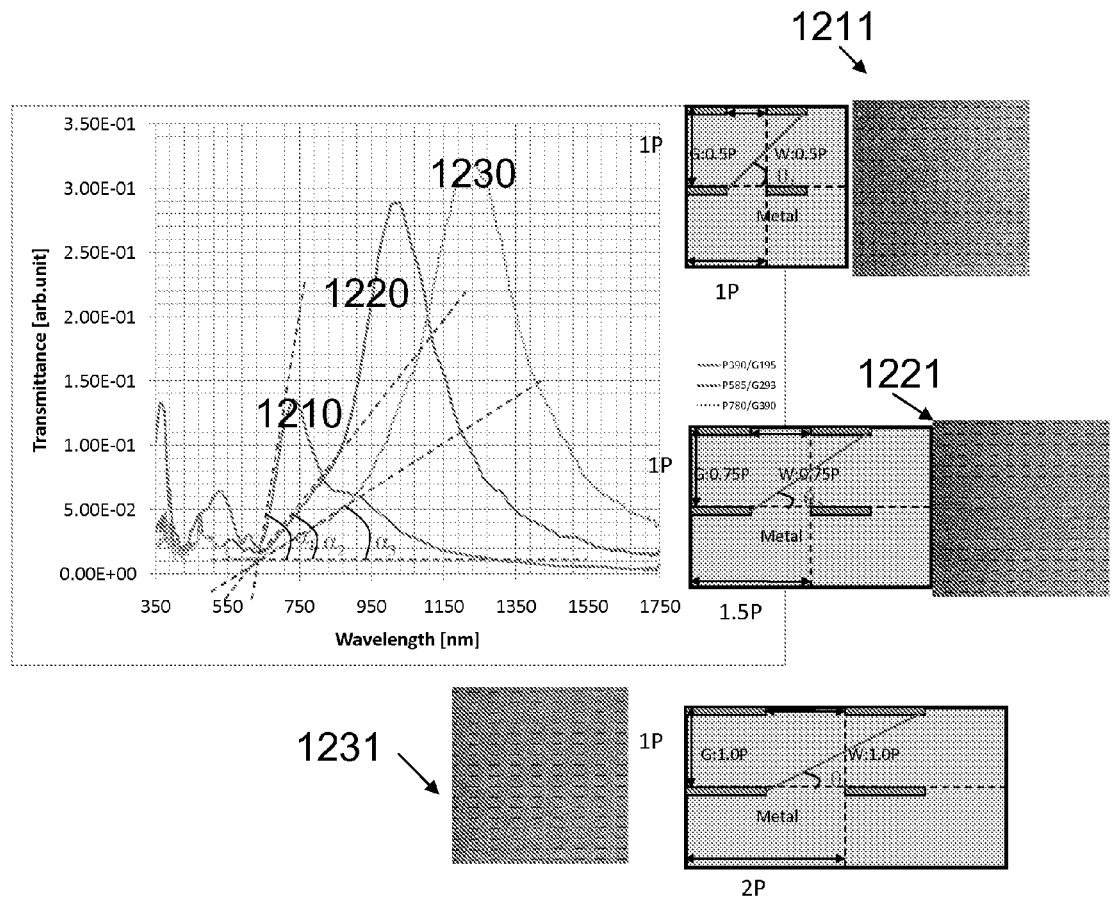
FIG. 12 shows spectra of 2-D array structures having different horizontal pitches, illustrating the effects on the transmittance spectra.

FIG. 12 shows spectra of 2-D array structures 1211, 1221, 1231 having different horizontal pitches, illustrating the effects on the transmittance spectra 1210, 1220, 1230. By increasing the horizontal pitch, from example, from 1P to 2P, while the horizontal gap is kept at half of the horizontal pitch, and the vertical pitch is fixed at about 390 nm and the gap is fixed at about 40 nm, it can be shown that the transmittance spectra 1210, 1220, 1230 have increasingly higher peaks. The slopes of the peaks are different as well.

Figure 13:
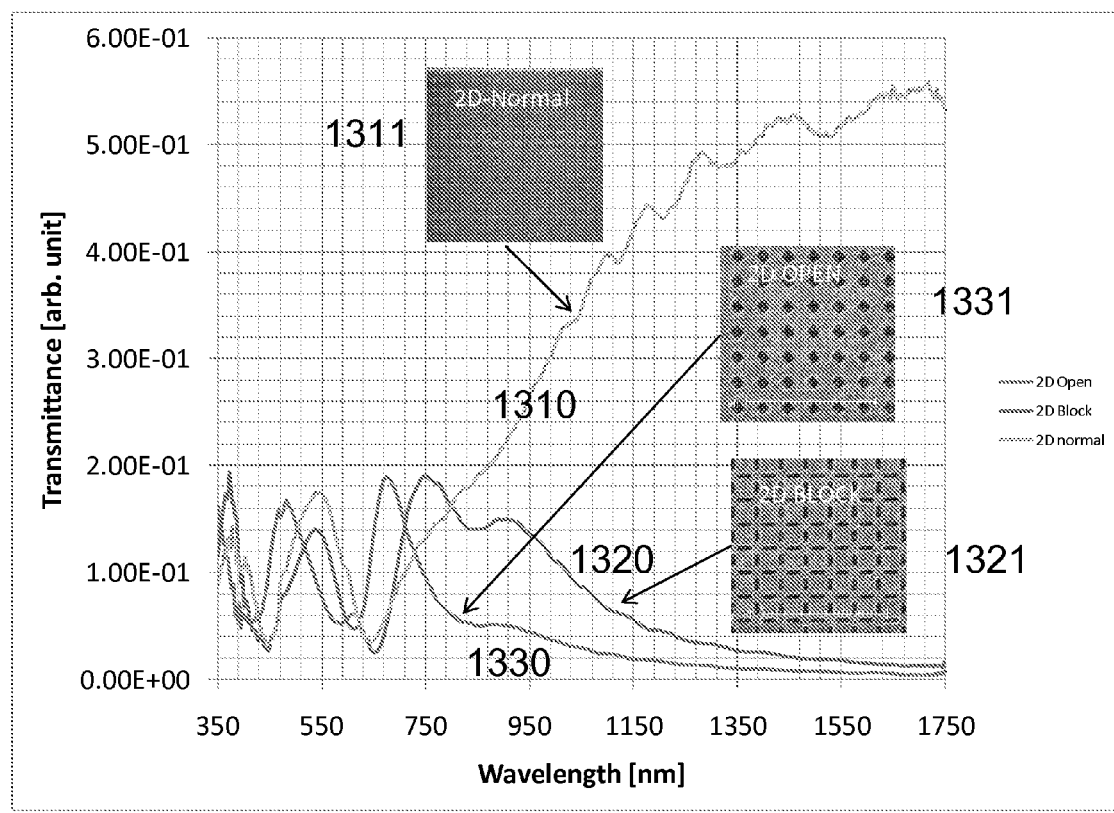
FIG. 13 shows spectra of 2-D array structures having different shapes of apertures illustrating the effect of the aperture shapes on the spectra.

FIG. 13 shows spectra of 2-D array structures having different shapes of apertures illustrating the effect of the aperture shapes on the spectra. A simple, rectangular pattern 1311 comprising intersecting lines, similar to that of the structure 1121 shown in FIG. 11 and, results in a spectrum 1311 without a drop at the long wavelength end. A rectangular pattern 1321, in which the apertures are shaped like crosses with their center portions blocked, results in a spectrum 1320 with a drop at the long wavelength end and a relatively broad peak. A rectangular pattern 1331, in which the apertures are rhombus shaped, results in a spectrum 1330 having a desirable narrow peak between the dip and the cutoff wavelength (i.e., drop).

Figure 14:
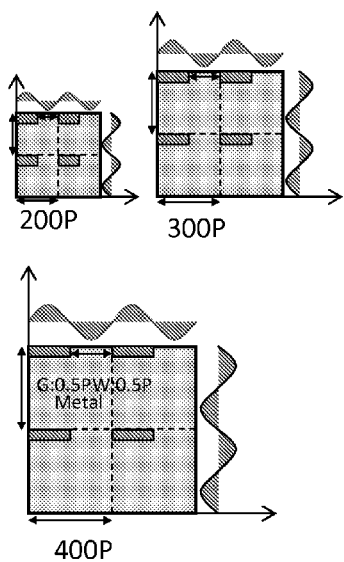
FIG. 14 shows the effect of increase in both the horizontal and the vertical pitches on the spectra.
Figure 14:
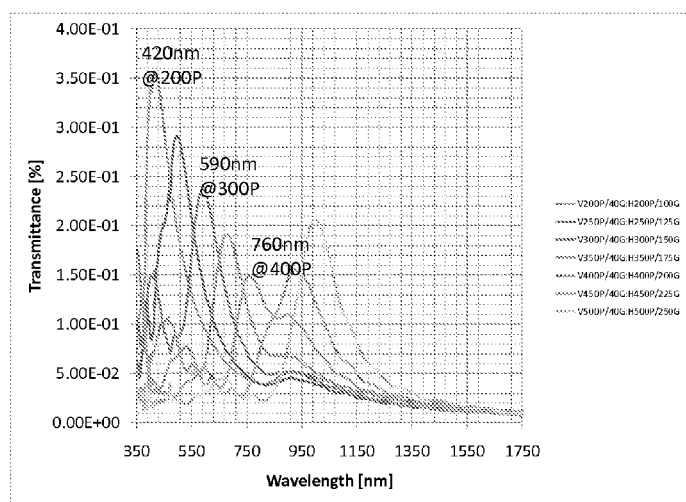
Figure 14:
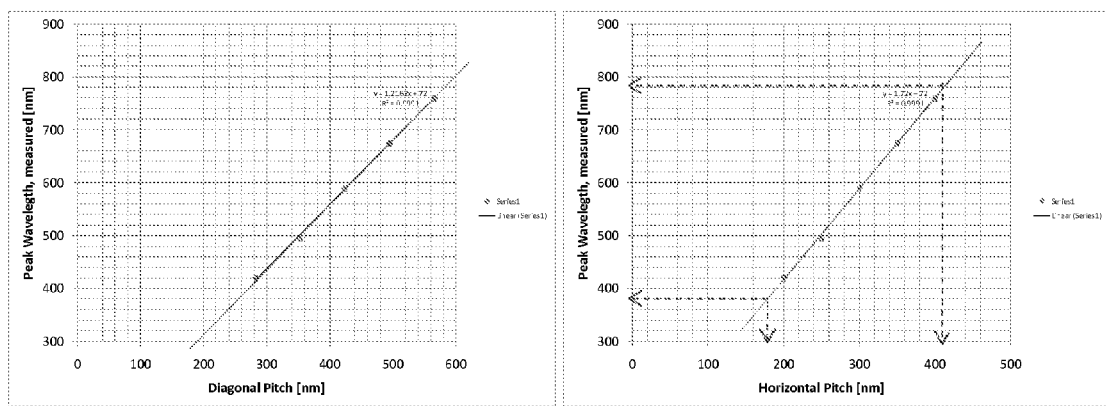

FIG. 14 shows the effect of horizontal pitch on the spectra. As the horizontal pitch increases from about 200P to about 300P and then 400P while the vertical pitch and the horizontal gap of the slits increase proportionally, the peak locations shift red-ward (to longer wavelength) from about 420 nm, to about 590 nm, and then to about 760 nm. The peak wavelength has a linear relation with horizontal pitch or the diagonal pitch.

Figures 15A, 15B:
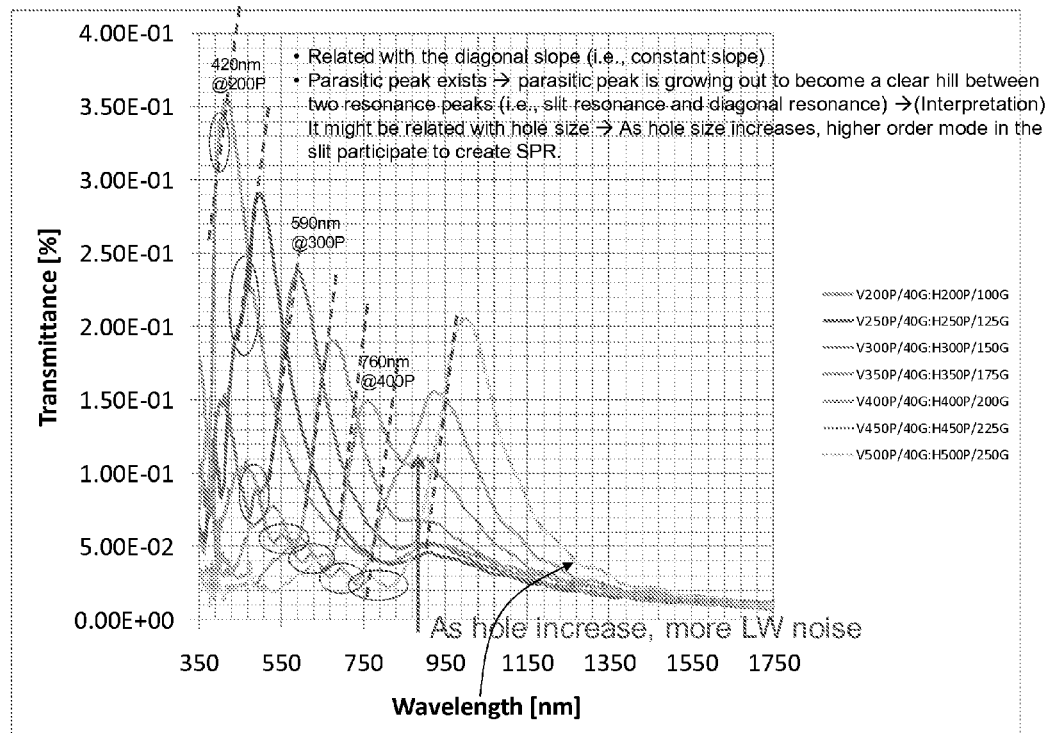
FIG. 15A shows the effect of vertical pitch on the spectra.
FIG. 15B tabulates the values of the pitch and the gaps, and the resulting spectral data.
Figure 15C:
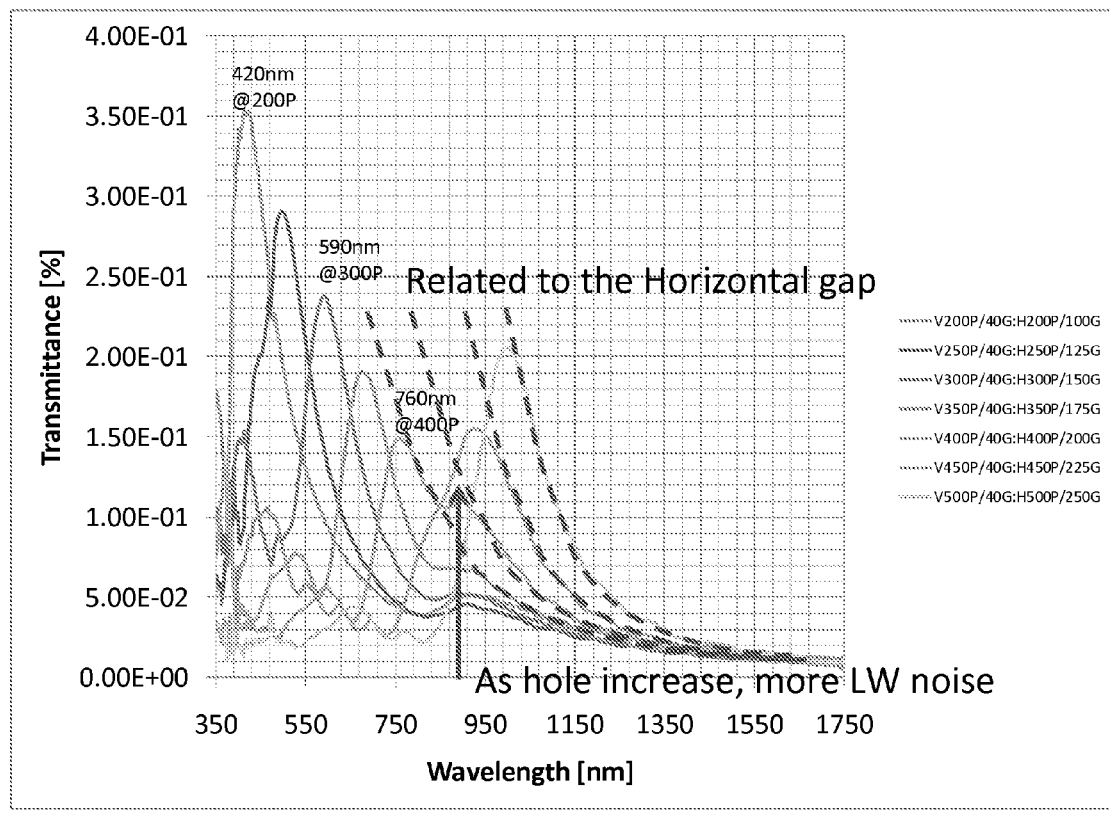
FIG. 15C shows the effect of the aperture size on the spectra.

FIG. 15A shows the effect of vertical pitch on the spectra. As the vertical pitch increases, the dip shifts towards the long wavelength end, and the slopes at the left sides of the peaks also change. The pitch is kept the same in horizontal and vertical directions, and the horizontal gap remains at 50% of the pitch. FIG. 15B tabulates the values of the pitch and the gaps, and the resulting spectral data. FIG. 15C shows the effect of the aperture size on the spectra. As the horizontal gap increases together with the pitch values while the vertical gap is kept const, the cut-off wavelengths increase, and the slopes at the right sides of the peaks also change. The pitch is kept the same in horizontal and vertical directions, and the horizontal gap remains at 50% of the pitch.

Figure 16:
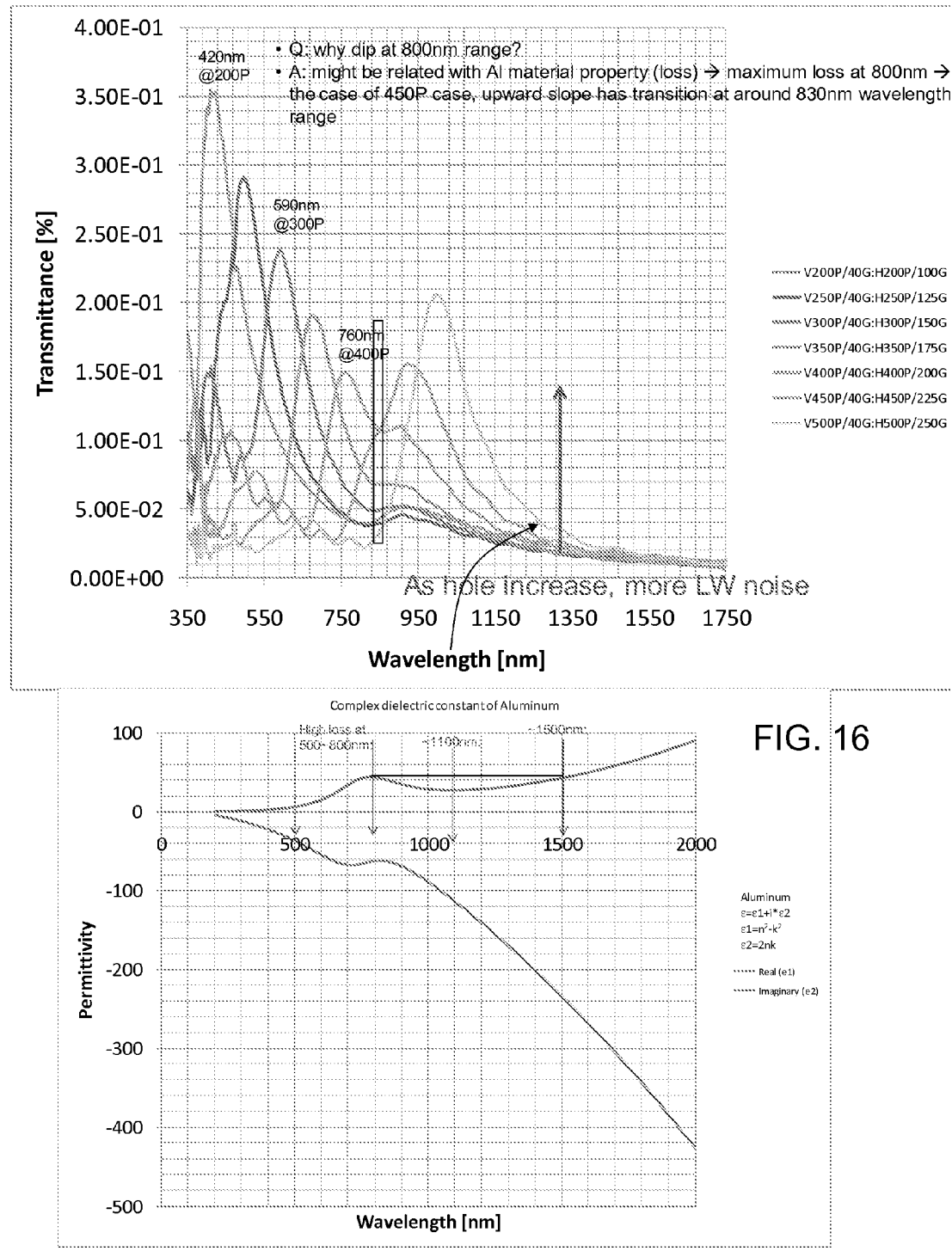
FIG. 16 illustrates the effect of the increase in horizontal gap on the spectra while the pitch increases proportionally.

FIG. 16 illustrates the effect of the increase in horizontal gap on the spectra while the pitch increases proportionally. As the vertical gap increases, the transmittance at the right side of the peak increases. The noise in the long wavelength range can also increase. The dip at about 800 nm may be related to the metal (Al) material property. For example, the permittivity curve of Al indicates that there may be a high loss in the 500~800 nm range.

Figure 17:
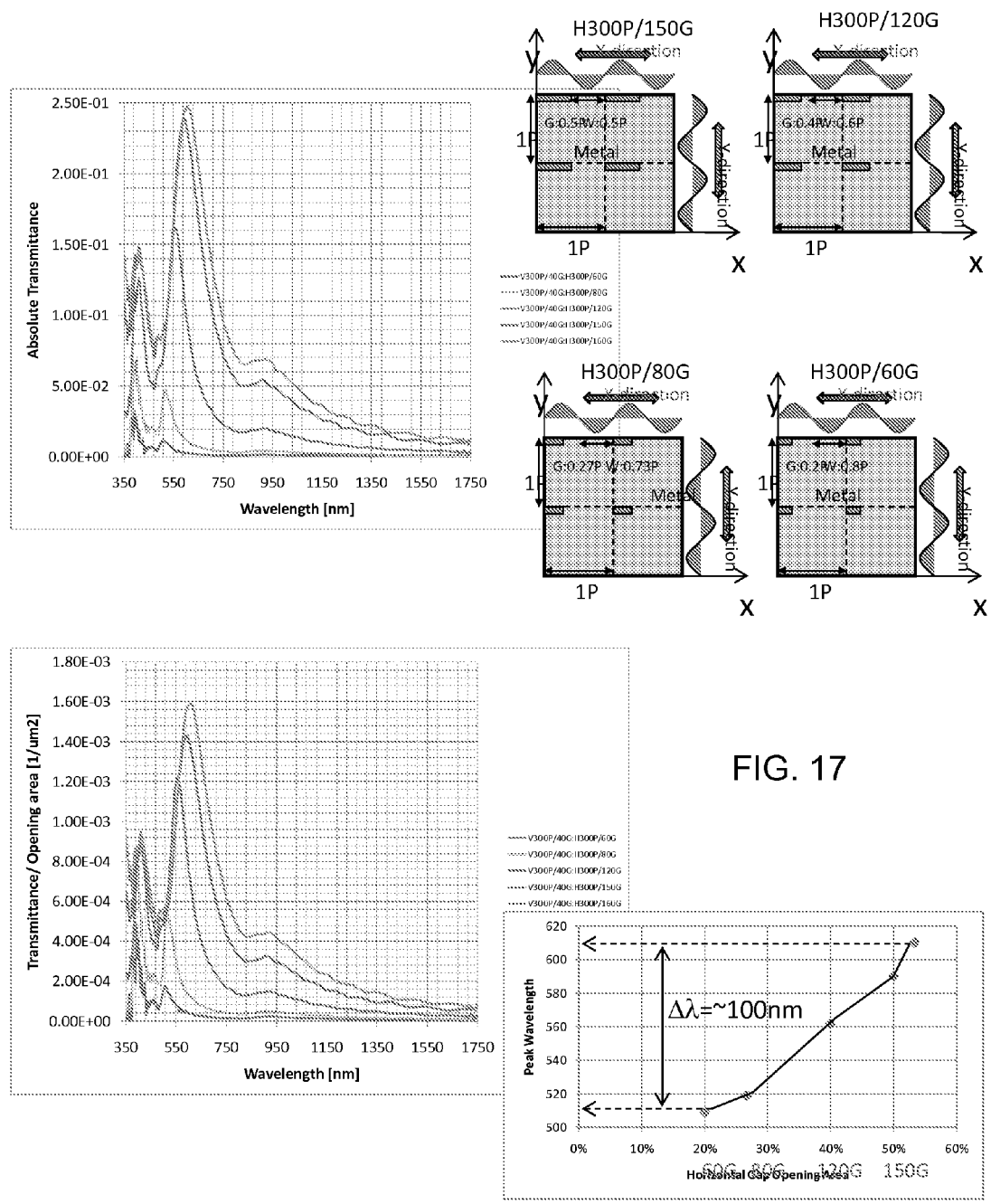
FIG. 17 illustrates the effect of the increase in horizontal gap on the spectra while the pitch is kept constant.

FIG. 17 illustrates the effect of the increase in horizontal gap on the spectra while the pitch is kept constant. The peak wavelength increases while the peak broadens slightly. The transmitted light per unit aperture (gap) area=Transmittance/Total area of gap, and the total area of gap=(Gap area/unit cell)×(# of cell in each filter).

Figures 18A, 18B:
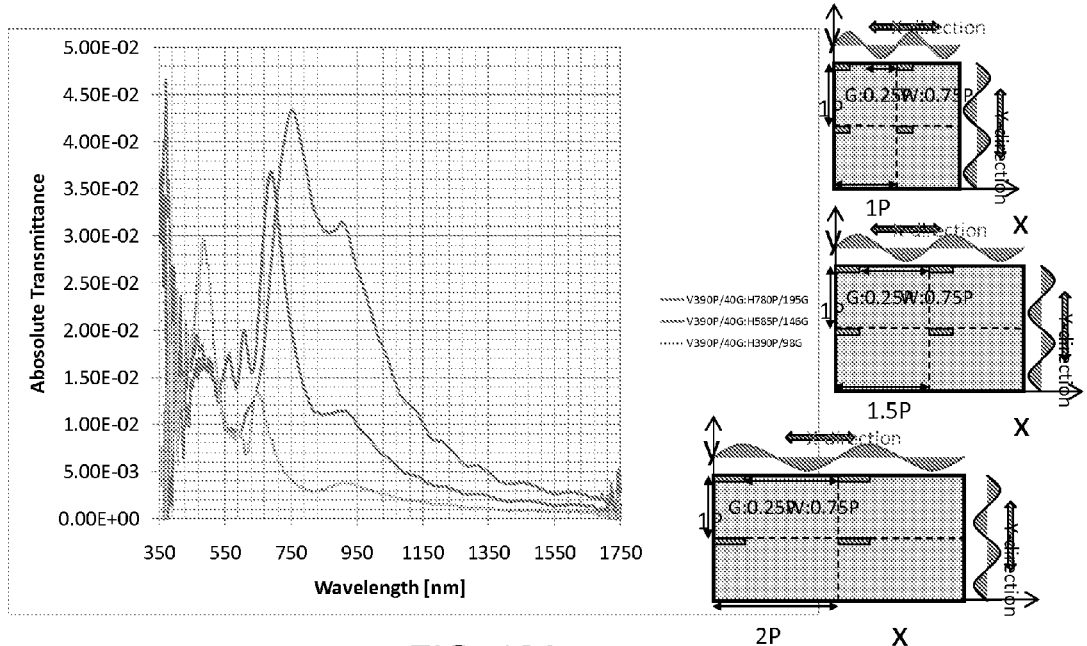
FIG. 18A illustrates the effect of the horizontal pitch on the spectra.
FIG. 18B tabulates the values of the spectra for horizontal gaps ranging from 60 nm to 150 nm.

FIG. 18A illustrates the effect of the horizontal pitch on the spectra. While the horizontal pitch increases from 1P to 2P, the horizontal gap increases proportionally and is kept at 0.25×the horizontal pitch. The vertical pitch is fixed at 390 nm, and the vertical gap is fixed at 40 nm. The peak of the spectrum shifts toward the long wavelength end and becomes broader. An optimal configuration may be present, and can be determined by simulating a large number of different configurations. For example, in FIG. 18A it is shown that when the horizontal pitch is 585 nm, the peak is substantially narrower than that for a horizontal pitch of 780 nm while having a desirable intensity.

FIG. 18B tabulates the values of the spectra for horizontal gaps ranging from 60 nm to 150 nm.

Figure 18C:
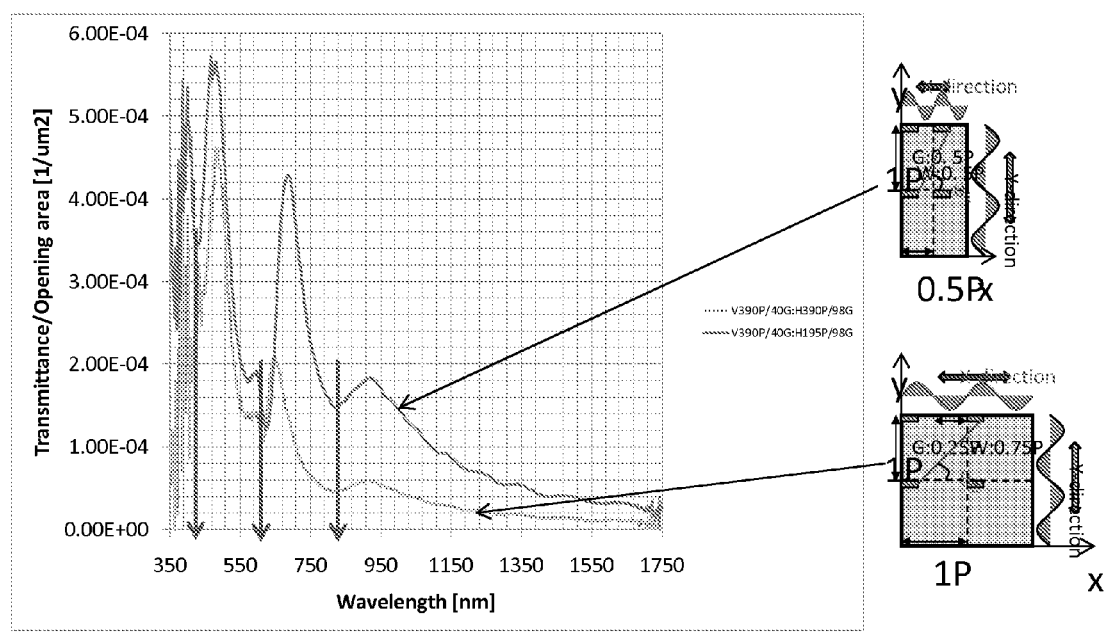
FIG. 18C illustrates the effect of the horizontal gap on the spectra with an increase in horizontal pitch and a fixed vertical pitch.

FIG. 18C illustrates the effect of the horizontal gap on the spectra with an increase in horizontal pitch and a fixed vertical pitch. The area of the gap is kept at a constant value, with a horizontal gap of 98 nm. The transmittance is normalized by the hole area.

Figure 19:
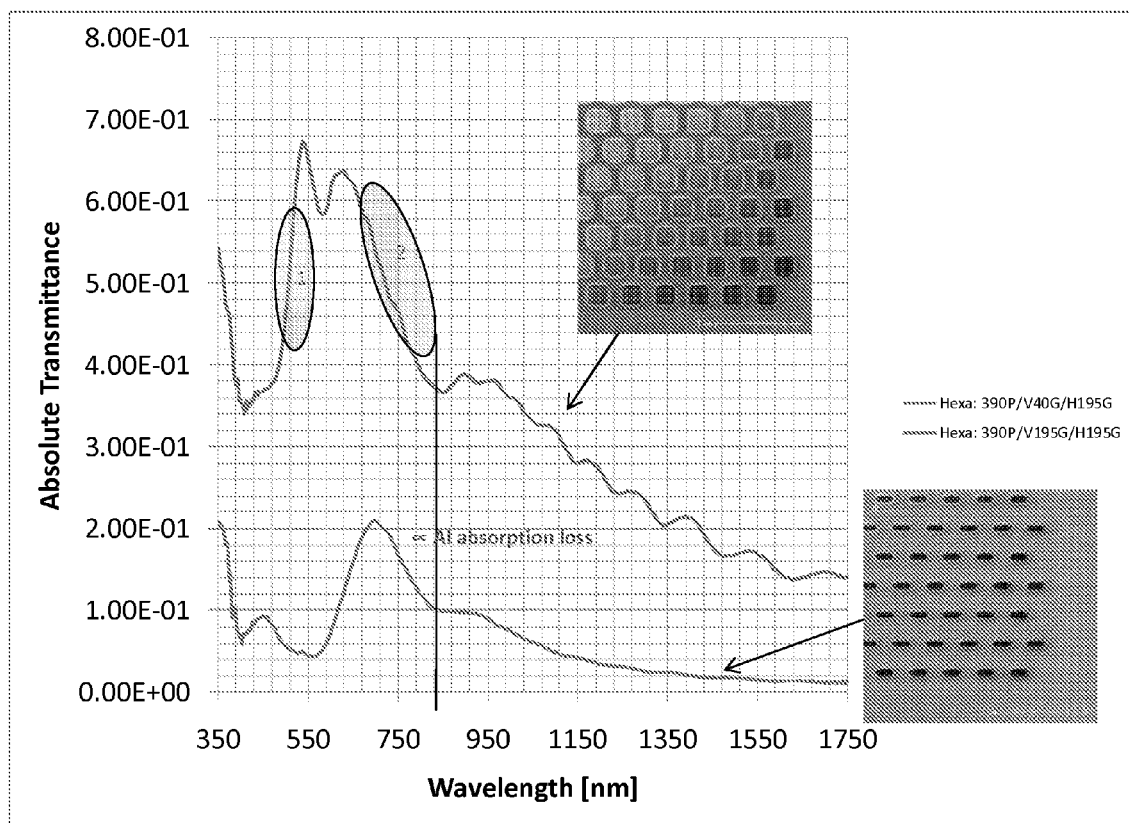
FIG. 19 illustrates transmittance spectra for triangular arrays.

FIG. 19 illustrates transmittance spectra for triangular arrays. If the area of the aperture is large, the filter acts like a polarizer filter, and the intensity slope increases. If the aperture is small, then the wavelength is limited by the hole size, and cut-off mechanism takes place, and thus the intensity slope decreases.

Figure 20:
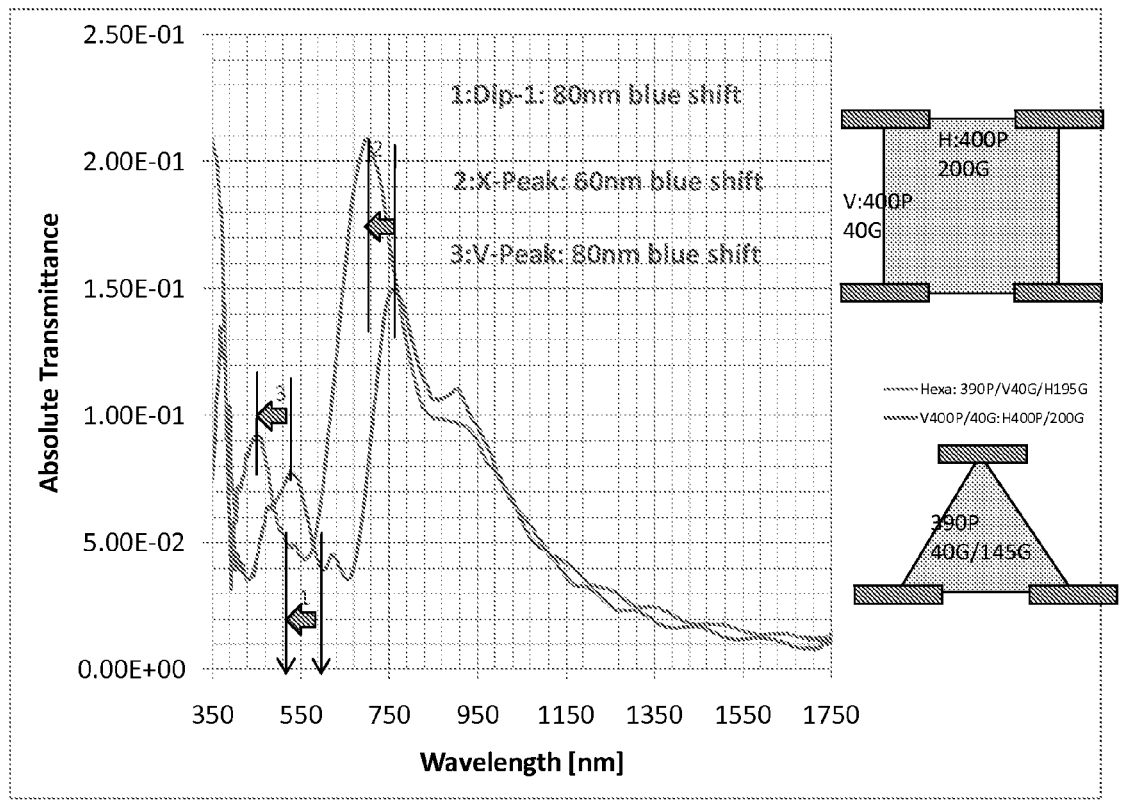
FIG. 20 shows a comparison of transmittance spectra of rectangular and triangular array structures.

FIG. 20 shows a comparison of transmittance spectra of rectangular and triangular array structures. In terms of slit array structure, the hexagonal (or triangular) array shifts the peak wavelength for about 60-80 nm toward shorter wavelength compared with the rectangular array at the same footprint.

Figure 21:
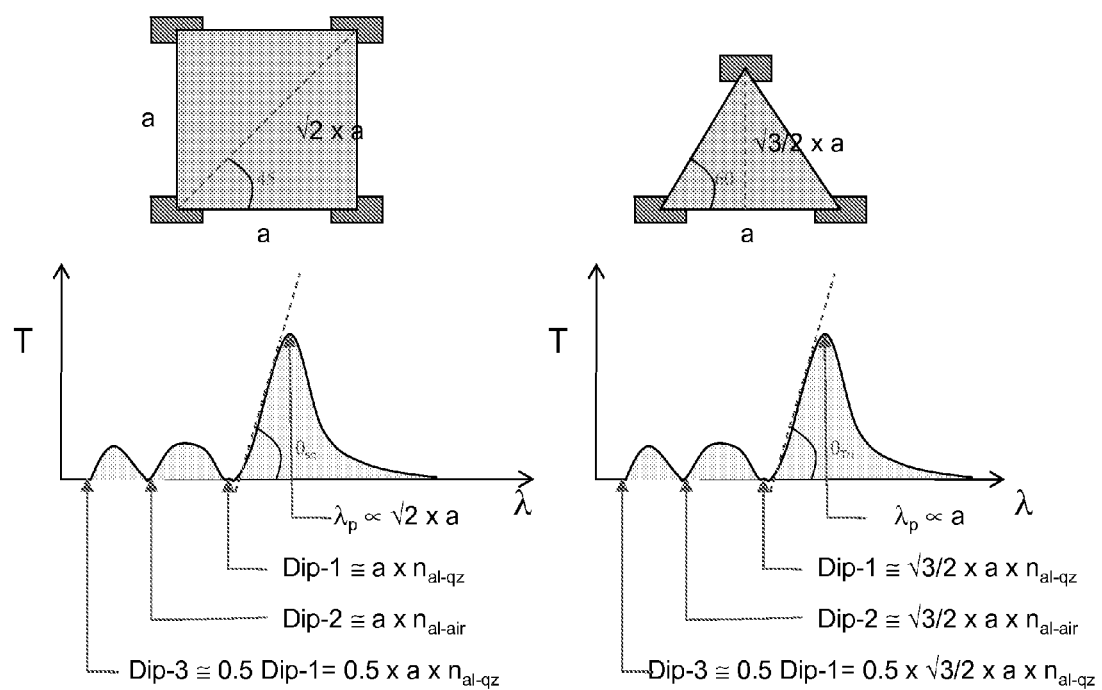
FIG. 21 further illustrates advantages of a triangular array over a square array.

FIG. 21 further illustrates advantages of a triangular array shape over a square array shape. $\theta_{sq} < \theta_{tri}$ indicates that triangular arrays can have a sharper peak in its spectrum than square arrays, resulting in a decreased FWHM. The dip location of the triangular array is shifted for about 13% toward shorter wavelength, resulting from that the height of the triangle is about $\sqrt{3}/2=0.87$ that of the square. Thus, $\lambda_p$ can be shifted toward shorter wavelengths at the same footprint by engineering the shape of the periodic pattern.

In the transmittance spectra, the first dip results from a Plasmon mode at an aluminum-quartz interface, and the second dip results from a Plasmon mode at an aluminum-air interface. Thus, by engineering the refractive indices, for example, by selecting the dielectric materials on one side or both sides of the conductive layer, and/or selecting the conductive material itself, the spectral shape can be modified. In particular, increasing the types of interfaces can increase the number of peaks and dips. If fewer peaks and dips are desired, a single type of dielectric material is desired. This provides another design freedom in addition to designing the periodic patterns and the shapes and sizes of the array elements.

Figure 22:
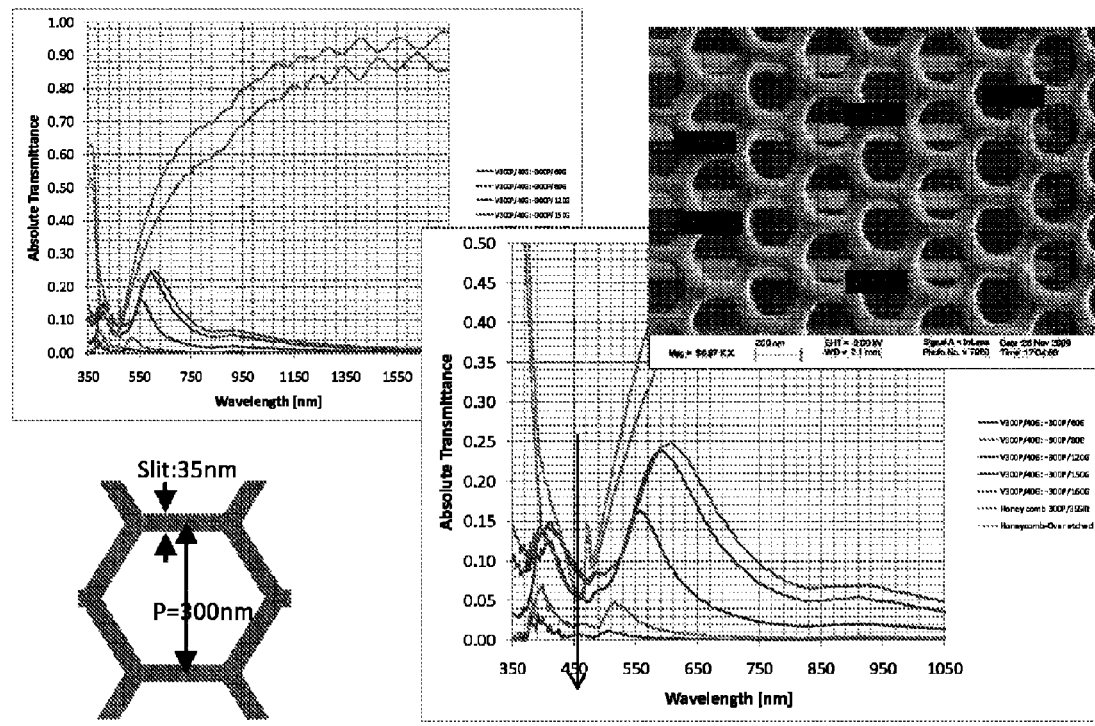
FIG. 22 illustrates transmittance spectra from an inverse honey comb structure.

FIG. 22 illustrates transmittance spectra from an inverse honey comb structure.

Figure 23:
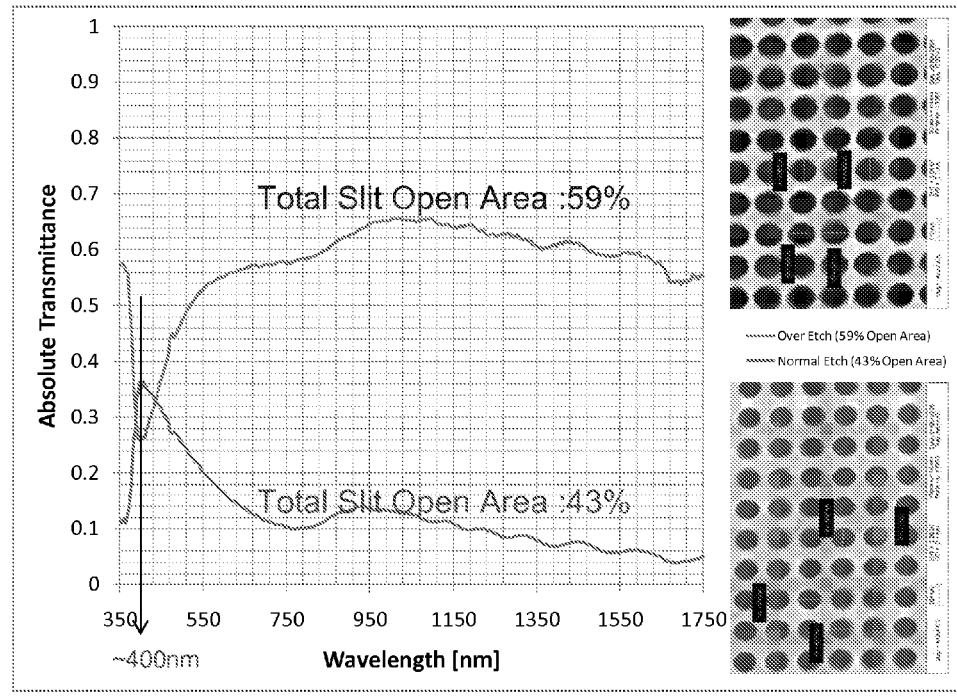
FIG. 23 shows the effect of the aperture area on the spectra.

FIG. 23 shows the effect of the aperture area on the spectra. As shown, when the slit open area is 59% of the total area of the conductive layer, the spectrum does not show a drop in the long wavelength end, and the filter can function as a long-pass filter or polarizer. When the slit open area is 43% of the total area of the conductive layer, the drop or cut off is present.

Figure 24:
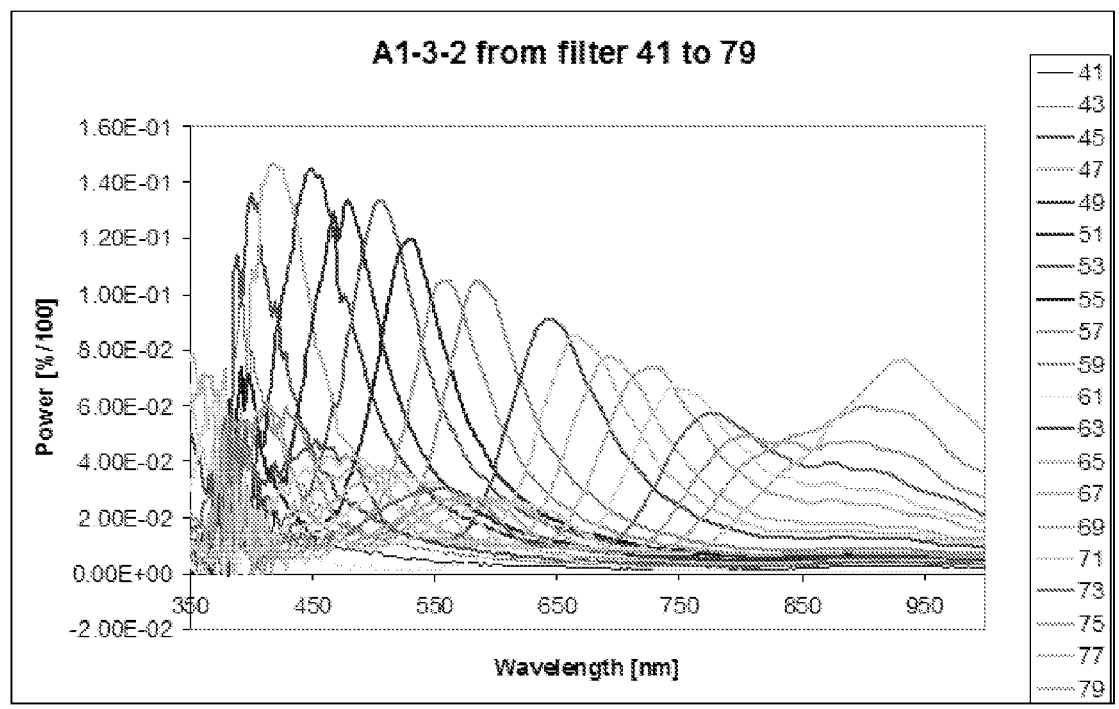
FIG. 24 shows measured spectra of various filters.

FIG. 24 shows measured spectra of various filters.

Figure 25:
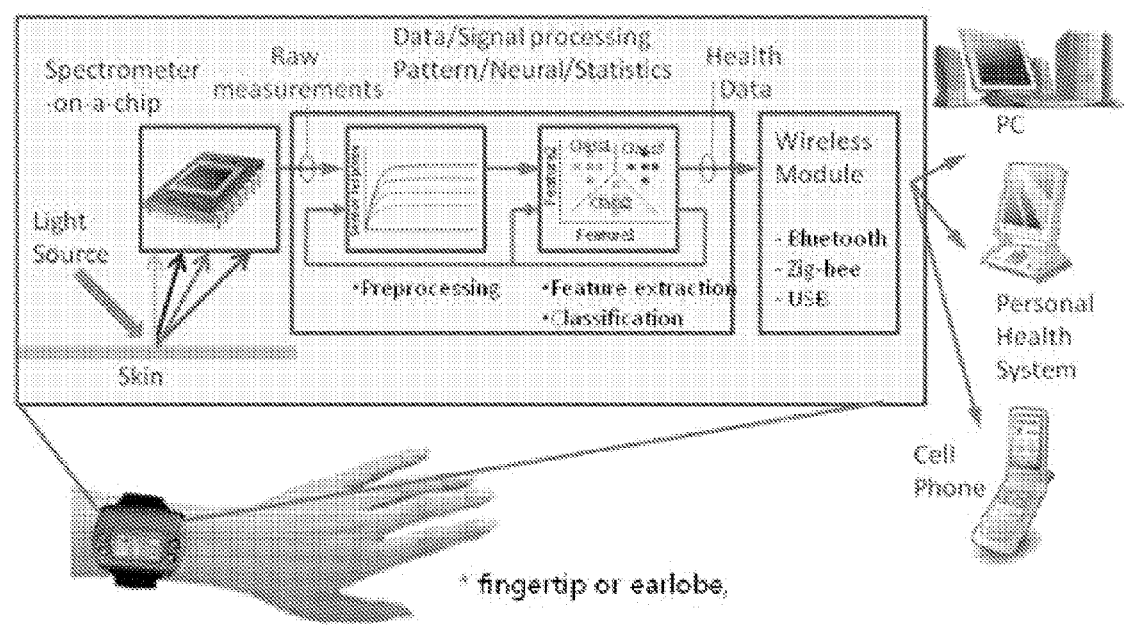
FIG. 25 illustrates a system employing the filters disclosed herein.

FIG. 25 illustrates a system employing the filters disclosed herein. The system is configured as a wearable personal health monitor, including a strap to attach the system to a wrist. Alternatively, with a different mechanical attachment device, the system can be attached to a fingertip or an earlobe of a body. The system can include a light source that emits light onto the skin. They reflected, scattered, or transmitted light can be analyzed by a spectrometer on a chip, where the spectrometer includes the optical filters disclosed herein. The measured raw data can be processed by a data/signal processing unit. The processing can include a preprocessing, and feature extraction and classification. These data can be interpreted as health data, which is transmitted to a wireless module, which in turn sends the health data through wireless (e.g., Bluetooth) or wired (e.g., USB) communication device to a PC, a personal health monitoring system, or to a cell phone.

FIGS. 26-1 through 26-56 show computer simulations of various device structures. Such simulations can be used to design optimized filter configurations. In particular, FIGS. 26-1 through 26-11 show simulated spectra of various multilayer structures. As illustrated in the cross-sectional views of the devices, the distances between the two layers, the shift between the two periodic patterns, the different pitches in the two layers, etc, can all affect the shape of the spectra significantly. FIGS. 26-12 through 26-24 show the effect of multiple periods in the pattern. FIGS. 26-25 through 26-32 show the spectra when the periodic pattern is configured as a 1D polarizer or long-pass filter. FIGS. 26-33 through 26-38 show the effect of variations in the aperture shapes.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety, including the following references:

Roman Z Morawski, REVIEW ARTICLE, Spectrophotometric applications of digital signal processing, Meas. Sci. Technol. 17 (2006) R117-R144;

Ben Slima M, Morawski R Z and Barwicz A 1992, Spline-based variational method with constraints for spectrophotometric data correction IEEE Trans. Instrum. Meas. 41 786-90;

Miekina A and Morawski R Z 1993 Incorporation of the positivity constraint into a Tikhonov-method-based algorithm of measurand reconstruction Proc. Int. IMEKO-TC1&TC7 Coll. (London, UK, 8-10 Sep. 1993) pp 299-04 R140 Review Article;

Szczecinski L, Morawski R Z and Barwicz A 1994 Original-domain Tikhonov regularisation and non-negativity constraint improve resolution of spectrometric analysis Proc. 13th IMEKO World Congress (Torino, 5-9 Sep. 1994) pp 441-6;

Massicotte D, Morawski R Z and Barwicz A 1995 Incorporation of a positivity constraint into a Kalman-filter-based algorithm for correction of spectrometric data IEEE Trans. Instrum. Meas. 44 2-7;

Ben Slima M, Morawski R Z and Barwicz A 1997 Kalman-filter-based algorithms of spectrophotometric data correction: Part II. Use of splines for approximation of spectra IEEE Trans. Instrum. Meas. 46 685-9;

Massicotte D, Morawski R Z and Barwicz A 1997 Kalman-filter-based algorithms of spectrophotometric data correction: Part I. An iterative algorithm of deconvolution IEEE Trans. Instrum. Meas. 46 685-9;

Szczecinski L, Morawski R Z and Barwicz A 1997 A cubic FIR-type filter for numerical correction of spectrometric data IEEE Trans. Instrum. Meas. 46 922-8;

Szczecinski L, Morawski R Z and Barwicz A 1997 Numerical correction of spectrometric data using a bilinear operator of measurand reconstruction Instrum. Sci. Technol. 25 197-205;

Szczecinski L, Morawski R Z and Barwicz A 1998 Variational algorithms for spectrogram correction based on entropy-like criteria J. Chemometr. 12/6 397-403;

Szczecinski L, Morawski R Z and Barwicz A 1998 Numerical correction of spectrometric data using a rational filter J. Chemometr. 12/6 379-95;

Wisniewski M P, Morawski R Z and Barwicz A 2003 An adaptive rational filter for interpretation of spectrometric data IEEE Trans. Instrum. Meas. 52 966-72;

Sprzeczak P and Morawski R Z 2000 Calibration of a spectrometer using a genetic algorithm IEEE Trans. Instrum. Meas. 49 449-54;

Sprzeczak P and Morawski R Z 2001 Cauchy-filter-based algorithms for reconstruction of absorption spectra IEEE Trans. Instrum. Meas. 50 1123-6;

Sprzeczak P and Morawski R Z 2002 Cauchy filters versus neural networks when applied for reconstruction of absorption spectra IEEE Trans. Instrum. Meas. 51 815-8;

Cheng-Chun Chang and Heung-No Lee, On the estimation of target spectrum for filter array based spectrometers, 21 Jan. 2008/Vol. 16, No. 2/OPTICS EXPRESS 1056;

B. Stuart, Modern IR Spectroscopy. New York: Wiley, 1996;

M. Born and E. Wolf, Principles of Optics, 5th ed. New York: Pergamon, 1975;

B. Saleh and M. C. Teich, Fundamentals of Photonics. New York: Wiley, 1991;

D. Rossberg, "Silicon micromachined infrared sensor with tunable wavelength selectivity for application in infrared spectroscopy," Sens. Actuators A, vol. 46-47, pp. 413-416, 1995;

G. Minas, J. S. Martins, C. Pereira, C. Lima, R. F. Wolffenbuttel, and J. H. Correia, "Lab-on-a-chip for measuring uric acid in biological fluids," in Proc. Eurosensors XVI, Prague, Czech Republic, Sep. 15-18, 2002, pp. 66-69;

R. F. Wolffenbuttel, "Silicon photodetectors with a selective spectral response," in Sensors Update, H. Baltes, J. Hesse, and J. Korvink, Eds. Berlin, Germany: Wiley-VCH, 2001, vol. 9, pp. 69-101;

R. F. Wolffenbuttel, "Silicon photodetectors with a selective spectral response," in Sensors Update, H. Baltes, J. Hesse, and J. Korvink, Eds. Berlin, Germany: Wiley-VCH, 2001, vol. 9, pp. 69-101;

J. W. Holm-Kennedy, K. W. Tsang, W. W. Sze, F. Jiang, and D. Yang, "A novel monolithic chip-integrated color spectrometer: The distributed wavelength filter component," Proc. SPIE, vol. 1527, pp. 322-331, 1991;

"High-selectivity single-chip spectrometer in silicon for operation in the visible part of the spectrum," IEEE Trans. Electron Devices, vol. 47, pp. 553-559, March 2000;

J. H. Correia, G. de Graaf, S.-H. Kong, M. Bartek, and R. F. Wolffenbuttel, "Single-chip CMOS optical micro-interferometer," Sens. Actuators A, vol. 82, pp. 191-197, 2000;

Reinoud F. Wolffenbuttel, "State-of-the-Art in Integrated Optical Microspectrometers," IEEE TRANSACTIONS ON INSTRUMENTATION AND MEASUREMENT, VOL. 53, NO. 1, FEBRUARY 2004;

Sameer Bhalotra, "Adaptive Optical Microspectrometers & Spectra-Selective Sensing," Dept. of Applied Physics, Stanford University, Apr. 30, 2004;

R. F. Wolffenbuttel, "MEMS-based optical mini- and microspectrometers for the visible and infrared spectral range," J. of Micromechanics and Microengineering, (2005) S145-S152;

S. H. Kong, D. D. L. Wijngaards, R. F. Wolffenbuttel, "Infrared micro-spectrometer based on a diffraction grating," Sens. Act. A 92, 88-95 (2001);

Wallrabe U, Mohr J and Solf C 2004 Mini-FT spectrometer for the near-infrared Proc Eurosensors XVIII (Rome, Italy, 12-15 Sep. 2004) pp 160-1;

Correia J H, de Graaf G, Kong S-H, Bartek M and Wolffenbuttel R F 2000 Single-chip CMOS optical micro-interferometer Sensors Actuators A 82 191-7;

Hank Hogan, "Low-Cost Spectrometer Incorporates Spherical Beam Volume Hologram Replacing grating offers economic benefits without sacrificing resolution," Photonics Spectra, Technology World|April 2006;

G. Minas et al., Sensors and Actuators A 115 (2004) 362-367;

Reinoud F. Wolffenbuttel et al/, Optics Express, Mar. 19, 2007, pp. 3581-3588;

Kalyani Chaganti et al/, 1 May 2006/Vol. 14, No. 9/OPTICS EXPRESS 4068;

Zhijun Sun, Yun Suk Jung, and Hong Koo Kim, "Dynamic evolution of surface plasmon resonances in metallic nanoslit arrays," APPLIED PHYSICS LETTERS 86, 023111 (2005);

Hong Koo Kim et al, Published PCT Patent Application, PCT/US2004/023499, (International filing date: Jul. 22, 2004, Priority date: Aug. 6, 2003) and its U.S. counterpart published application US 2006/0273245 A1;

Ben-Israel, Adi; Thomas N. E. Greville (2003) Generalized Inverses. Springer-Verlag. ISBN 0-387-00293-6;

Moore, E. H. (1920). "On the reciprocal of the general algebraic matrix." Bulletin of the American Mathematical Society 26: 394-395;

Penrose, Roger (1955). "A generalized inverse for matrices". Proceedings of the Cambridge Philosophical Society 51: 406-413;

Golub, Gene H.; Charles F. Van Loan (1996). Matrix computations, 3$^{rd}$ edition, Baltimore: Johns Hopkins. ISBN 0-8018-5414-8;

Penrose, Roger (1956). "On best approximate solution of linear matrix equations". Proceedings of the Cambridge Philosophical Society 52: 17-19;

Shahid U. H. Qureshi, "Adaptive Equalization" PROCEEDINGS OF THE IEEE, VOL. 73. NO. 9, SEPTEMBER 1985;

Monson H. Hayes *Statistical Digital Signal Processing and Modeling*, Wiley, 1996, ISBN 0-471-59431-8;

Simon Haykin *Adaptive Filter Theory*, Prentice Hall, 2002, ISBN 0-13-048434-2;

C. P. Bacon, Y. Mattley, and R. Defrece, "Miniature spectroscopic instrumentation: applications to biology and chemistry," Review of Scientific Instruments 75, 1-16 (2004).

D. C. Heinz, and C.-I Chang, "Fully constrained least-squares linear spectral mixture analysis method for material quantification in hyperspectral imagery," IEEE Trans. on Geoscience and Remote Sensing 39, 529-546 (2001);

J. H. Correia, G. Graaf, M. Bartek, and R. F. Wolffenbuttel, "A single-chip CMOS potical microspectrometer with light-to-frequency converter and bus interface," IEEE Journal of Solid-State Circuits 37, 1344-1347 (2002);

K. Chaganti, I. Salakhutdinov, I. Avrutsky, G. W. Auner, "A simple miniature optical spectrometer with a planar waveguide grating coupler in combination with a plano-convex leng," Optics Express 14, 4064-4072 (2006);

R. F. Wolffenbuttel, "State-of-the-art in integrated optical microspectrometers," IEEE Trans. on Instrumentation and Measurement 53, 197-202 (2004);

R. Shogenji, Y. Kitamura, K. Yamada, S. Miyatake, and J. Tanida, "Multispectral imaging using compact compound optics," Optics Express 12, 1643-1655 (2004);

S.-W. Wang, C. Xia, X. Cheng, W. Lu, L. Wang, Y. Wu, and Z. Wang, "Integrated optical filter arrays fabricated by using the combinatorial etching technique," Optics Letters 31, 332-334 (2006);

S.-W. Wang, C. Xia, X. Cheng, W. Lu, M. Li, H. Wang, W. Zheng, and T. Zhang, "Concept of a high-resolution miniature spectrometer using an integrated filter array," Optics Letters 32, 632-634 (2007);

C. L. Lawson and R. J. Hanson, *Solving Least Squares Problems*, Prentice-Hall, 1974;

J. G. Proakis, *Digital Communications*, McGraw Hill, 2000;

Yoshi Ohno, CIE Fundamentals for Color Measurements, IS&T NIP16 Conference, Vancouver, Canada, Oct. 16-20, 2000.

A. Mirzaaghazadeh, H. Motameni, "Using Neural Network in Pattern Recognition", Proceeding of Iran Computer Conference, 2002.

Kamarthi S. V., Pittner S., Accelerating neural network training using weight extrapolation, Neural networks, 9, 1999, pp. 1285-1299.

A. Burak Goktepe, "Role of Learning Algorithm in Neural Network-Based Back calculation of Flexible Pavements", Journal of Computing in Civil Engineering, Volume 20, Issue 5, pp. 370-373 (September/October 2006).

Manfred M Fisher, "Neural Networks: A General Framework for Non-Linear Function Approximation", Transactions in GIS, Volume 10 Page 521—July 2006, doi:10.1111/j.1467-9671.2006.01010.x, Volume 10 Issue 4.

V. Maiorov, "Approximation by neural networks and learning theory", Journal of Complexity, Volume 22, Issue 1, February 2006, Pages 102-117.

Salvatore Cavalieri, "A novel learning algorithm which improves the partial fault tolerance of multilayer neural networks", Neural Networks, Volume 12, Issue 1, January 1999, Pages 91-106.

Mohammad Teshnehlab and Keigo Watanabe (Eds.), "Intelligent control based on flexible neural networks", Kluwer Academic Publishers, Dordrecht, The Netherlands, 1999, ISBN 0-7923-5683-7, Automatica, Volume 38, Issue 3, March 2002, Pages 564-565.

Edgar Rinast, HansDieter Weiss, "Neural network approach computer=assisted interpretation of ultrasound images of the gallbladder", Europen Journal of Radiology, Volume 17, Issue 3, November 1993, Pages 175-178.

K. Economou and D. Lymberopoulos, "A new perspective in learning pattern generation for teaching neural networks", Neural Networks, Volume 12, Issue 4-5, June 1999, Pages 767-775.

Eiji Mizutani and James W. Demmel, "On structure-exploiting trustregion regularized nonlinear least squares algorithms for neural-network learning", Neural Networks, Volume 16, Issue 5-6, June-July 2003, pages 745-753.

R. Vicente Ruiz de angulo and Carme Torras, "Neural learning methods yielding functional invaiance", Theoretical Computer Science, Volume 320, Issue 1, 12 Jun. 2004, Pages 111-121.

Solanki Gautam, "Neural network and its application in pattern recognition", Seminar Report of Department of Computer Science and Engg. Indian Institue of Technology, Bombay, Nov. 5, 2004.

O. Lezray, D. Fournier and H. Cardot, "Neural network induction graph for pattern recognition", Neurocomputing 57 (2004) 257-274.

What is claimed is:

1. A method of characterizing an incident radiation employing filtering, the method comprising:
providing a spectrum sensor that includes a plurality of combinations of a filter device and a photodetector optically coupled to the filter device, wherein each filter device has a transmittance spectrum that is different from transmittance spectra of other filter devices, wherein at least one of the filter devices comprises a contiguous conductive layer in which the corresponding array of periodic patterns are embodied as apertures entirely laterally surrounded by the contiguous conductive layer, and wherein at least one of the filter devices comprises two dielectric layers, the contiguous conductive layer is disposed between the two dielectric layers, the continuous conductive layer includes a plurality of apertures and gaps, and the apertures and gaps are filled with a dielectric material that is the same as the two dielectric layers to thereby reduce numbers of dips and peaks in the spectrum and increase transmittance or reflectance;
providing an incident radiation to each filter device of the spectrum sensor;
detecting, at each photodetector, a transmitted radiation from a respective filter device;
generating measured outputs from the photodetector, wherein different transmittance spectra of the filter devices provide different weighting to a spectrum of the incident radiation; and generating an estimation of a spectral profile of the incident radiation from the measured outputs of the photodetector employing an estimation method that utilizes the different weighting corresponding to the filter devices.

2. The method of claim 1, further comprising analyzing a biochemical material by:

illuminating a portion of a biochemical material with an incident radiation, wherein the biological material is in a state that emits a spectrum that is different from the incident radiation;

sensing a color or spectral change in an emitted spectrum form the biochemical material with respect to the incident radiation using the spectrum sensor; and determining an amount of the biochemical material based on the color or spectral change.

3. The method of claim 2, further comprising exposing a color or spectral changing agent to the biochemical material prior to illumination of the biological material with the incident radiation, wherein the color or spectral changing agent provides the color or spectral change in the emitted spectrum.

4. The method of claim 1, wherein the filter devices are configured to be simultaneously exposed to the incident radiation.

5. The method of claim 1, wherein each filter device includes an array of periodic patterns having a plasmon mode resonant wavelength that differs from plasmon mode resonant wavelengths of other filter devices.

6. The method of claim 1, wherein the transmitted radiation has a transmittance spectrum that has a cutoff at a long-wavelength end of a spectrum, a dip at a plasmon mode resonant wavelength, and a peak between the dip and the cutoff.

7. The method of claim 6, wherein the different dips or peaks in the transmittance spectra provide different wavelengths of minimum or maximum weighting for the incident radiation to the measured outputs.

8. The method of claim 7, wherein the estimation method utilizes the different wavelengths of minimum or maximum weighting corresponding to the different dips or peaks.

9. The method of claim 1, further comprising:

generating an observed signal vector from the measured outputs; and multiplying a spectral response matrix and the observed signal vector to generate a vector representing the estimation of the spectral profile.

10. The method of claim 1, wherein the contiguous conductive layer comprises at least one of a conductive metal, an alloy of metals, a highly doped semiconductor, a carbon nanotube, a graphene, a material coated with highly conductive materials, and multiple layers thereof.

11. The method of claim 1, wherein the array of periodic patterns is a two dimensional array that is repeated along two different directions.

12. The method of claim 1, wherein shapes of the plurality of apertures include at least one of a rectangle, a ninety-degree zigzag shaped slit, and a cross.

13. The method of claim 1, wherein the spectrum sensor is configured to perform at least one of the following:

monitoring an ambient light;

monitoring proximity; and color or spectral detection.

14. The method of claim 1, wherein the spectrum sensor further comprises a processing unit configured to generate a vector of measured outputs from the array of photodetectors and to perform at least one of:

analyzing properties of a target object;

monitoring a change of the target object; and estimating a spectral profile of light from a target object through at least one of the following methods:

linear, multi-linear, or nonlinear estimation, trained mapping; and pattern recognition.

15. The method of claim 14, wherein the processing unit is configured to estimate a spectral profile of the light from the target object by sampling and digitizing a spectral response of the filters or combined spectral responses of each filter, and a spectral response of the photodetectors coupled to the filters, to thereby analyze properties of the target object.

* * * * *